(12) United States Patent
Hirose et al.

(10) Patent No.: US 10,153,437 B2
(45) Date of Patent: Dec. 11, 2018

(54) COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Tomoya Hirose, Kanagawa (JP); Harue Osaka, Kanagawa (JP); Takeyoshi Watabe, Kanagawa (JP); Satomi Mitsumori, Kanagawa (JP); Yuko Kubota, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 77 days.

(21) Appl. No.: 15/152,232

(22) Filed: May 11, 2016

(65) Prior Publication Data

US 2016/0336517 A1 Nov. 17, 2016

(30) Foreign Application Priority Data

May 12, 2015 (JP) .................. 2015-097649

(51) Int. Cl.
| | | |
|---|---|---|
| H01L 51/54 | (2006.01) | |
| H01L 51/00 | (2006.01) | |
| C07D 491/048 | (2006.01) | |
| C09K 11/06 | (2006.01) | |
| H01L 27/12 | (2006.01) | |
| H01L 51/50 | (2006.01) | |

(52) U.S. Cl.
CPC ...... *H01L 51/0071* (2013.01); *C07D 491/048* (2013.01); *C09K 11/06* (2013.01); *H01L 51/0072* (2013.01); *C09K 2211/1007* (2013.01); *C09K 2211/1059* (2013.01); *C09K 2211/185* (2013.01); *H01L 27/1248* (2013.01); *H01L 51/0085* (2013.01); *H01L 51/5016* (2013.01)

(58) Field of Classification Search
CPC ............ H01L 51/0071; H01L 51/0072; H01L 51/0085; H01L 27/1248; H01L 51/5016; H01L 51/5012; H01L 51/00; H01L 51/54; C07D 491/048; C09K 11/06; C09K 2211/185; C09K 2211/1007; C09K 2211/1059
USPC ......... 428/690, 411.1, 688; 252/301.16, 514, 252/500, 519.2
See application file for complete search history.

(56) References Cited

U.S. PATENT DOCUMENTS

| | | | |
|---|---|---|---|
| 6,097,147 A | 8/2000 | Baldo et al. | |
| 6,830,828 B2 | 12/2004 | Thompson et al. | |
| 6,902,830 B2 | 6/2005 | Thompson et al. | |
| 6,974,639 B2 | 12/2005 | Tsuboyama et al. | |
| 7,001,536 B2 | 2/2006 | Thompson et al. | |
| 7,220,495 B2 | 5/2007 | Tsuboyama et al. | |
| 7,291,406 B2 | 11/2007 | Thompson et al. | |
| 7,354,662 B2 | 4/2008 | Tsuboyama et al. | |
| 7,537,844 B2 | 5/2009 | Thompson et al. | |
| 7,883,787 B2 | 2/2011 | Thompson et al. | |
| 8,227,975 B2 | 7/2012 | Inoue et al. | |
| 8,247,086 B2 | 8/2012 | Inoue et al. | |
| 8,598,785 B2 | 12/2013 | Inoue et al. | |
| 8,790,794 B2 | 7/2014 | Osaka et al. | |
| 8,889,266 B2 | 11/2014 | Inoue et al. | |
| 8,889,858 B2 | 11/2014 | Inoue et al. | |
| 8,921,548 B2 | 12/2014 | Inoue et al. | |
| 8,946,697 B1 | 2/2015 | Ma et al. | |
| 8,968,888 B2 | 3/2015 | Kawata et al. | |
| 8,999,520 B2 | 4/2015 | Inoue et al. | |
| 9,012,036 B2 | 4/2015 | Inoue et al. | |
| 9,059,414 B2 | 6/2015 | Inoue et al. | |
| 2005/0221123 A1 | 10/2005 | Inoue et al. | |
| 2007/0129545 A1 | 6/2007 | Inoue et al. | |
| 2007/0244320 A1 | 10/2007 | Inoue et al. | |
| 2008/0305361 A1 | 12/2008 | Inoue et al. | |
| 2008/0318525 A1 | 12/2008 | Tanabe | |

(Continued)

FOREIGN PATENT DOCUMENTS

| | | |
|---|---|---|
| JP | 2009-035524 A | 2/2009 |
| JP | 2013-033958 A | 2/2013 |

(Continued)

OTHER PUBLICATIONS

CAS reg. No. 2043362-40-7 (Year: 2016).*
Niu, Y-H et al., "Highly Efficient Red Electrophosphorescent Devices Based on an Iridium Complex with Trifluoromethyl-Substituted Pyrimidine Ligand," Applied Physics Letters, Aug. 30, 2004, vol. 85, No. 9, pp. 1619-1621.
Caygill, G.B. et al., "Cyclometallated Compounds IV. Cyclopalladation of Phenylpyrimidines and X-ray Structure of a Doubly Cyclopalladated Derivative of 4,6-diphenylpyrimidine," Journal of Organometallic Chemistry, Feb. 13, 1990, vol. 382, No. 3, pp. 455-469.

(Continued)

*Primary Examiner* — Douglas J McGinty
(74) *Attorney, Agent, or Firm* — Husch Blackwell LLP

(57) ABSTRACT

Provided is a novel substance that can be used in an element capable of emitting phosphorescence, a novel substance that contributes to high emission efficiency, or a novel substance that contributes to light emission with high color purity. A light-emitting element includes a pair of electrodes and an EL layer between the pair of electrodes. The EL layer includes a substance including a carbazole skeleton. The substance is bonded to a substituted or unsubstituted first arylene group through a nitrogen atom included in the carbazole skeleton. The first arylene group is bonded to a substituted or unsubstituted benzofuropyridyl group or a substituted or unsubstituted benzothienopyridyl group. The first arylene group includes 1 to 5 substituted or unsubstituted second arylene groups which are bonded to one another. The EL layer may further include a layer including an emission center substance, specifically an iridium compound.

19 Claims, 26 Drawing Sheets

(56) References Cited

U.S. PATENT DOCUMENTS

| | | |
|---|---|---|
| 2009/0015143 A1 | 1/2009 | Inoue et al. |
| 2009/0039776 A1 | 2/2009 | Yamada et al. |
| 2009/0236973 A1 | 9/2009 | Yabe et al. |
| 2010/0105902 A1 | 4/2010 | Inoue et al. |
| 2010/0145044 A1 | 6/2010 | Inoue et al. |
| 2010/0187984 A1 | 7/2010 | Lin et al. |
| 2011/0082296 A1 | 4/2011 | Inoue et al. |
| 2011/0112296 A1 | 5/2011 | Thompson et al. |
| 2011/0248246 A1 | 10/2011 | Ogita et al. |
| 2012/0061707 A1 | 3/2012 | Seo et al. |
| 2012/0098417 A1 | 4/2012 | Inoue et al. |
| 2012/0138906 A1* | 6/2012 | Thompson ............ C09K 11/06 257/40 |
| 2012/0208999 A1 | 8/2012 | Konno |
| 2012/0264936 A1 | 10/2012 | Inoue et al. |
| 2013/0088144 A1 | 4/2013 | Inoue et al. |
| 2013/0165653 A1 | 6/2013 | Inoue et al. |
| 2013/0204003 A1 | 8/2013 | Osaka et al. |
| 2013/0270540 A1 | 10/2013 | Numata |
| 2013/0324721 A1 | 12/2013 | Inoue et al. |
| 2014/0131663 A1 | 5/2014 | Beers et al. |
| 2014/0131676 A1 | 5/2014 | Beers et al. |
| 2014/0291645 A1 | 10/2014 | Inoue et al. |
| 2014/0339526 A1 | 11/2014 | Inoue et al. |
| 2014/0367667 A1 | 12/2014 | Iwakuma et al. |
| 2015/0073142 A1 | 3/2015 | Ohsawa et al. |
| 2015/0108462 A1 | 4/2015 | Inoue et al. |
| 2016/0013421 A1 | 1/2016 | Inoue et al. |
| 2016/0093818 A1 | 3/2016 | Inoue et al. |
| 2016/0141524 A1* | 5/2016 | Thompson ............ C09K 11/06 257/40 |
| 2016/0308139 A1 | 10/2016 | Seo et al. |
| 2016/0336519 A1* | 11/2016 | Seo ...................... H01L 51/0072 |
| 2017/0338436 A1* | 11/2017 | Mitsumori .......... H01L 51/5016 |
| 2018/0182972 A1* | 6/2018 | So ........................ C07D 333/76 |

FOREIGN PATENT DOCUMENTS

| | | | | |
|---|---|---|---|---|
| JP | 2013-053158 A | | 3/2013 | |
| KR | 2014-0138393 A | | 12/2014 | |
| KR | 2015130651 A | * | 11/2015 | ............ C09K 11/06 |
| WO | WO 2000/070655 A2 | | 11/2000 | |
| WO | WO 2013/105206 A1 | | 7/2013 | |

OTHER PUBLICATIONS

Kawanishi, Y. et al., "Dependence of Spectroscopic, Electrochemical, and Excited-State Properties of tris chelate ruthenium(II) Complexes on Ligand Structure," Inorganic Chemistry, 1989, vol. 28, No. 15, pp. 2968-2975.

Kozhevnikov, V.N. et al., "Highly Luminescent Mixed-Metal Pt(II)/Ir(III) Complexes: Bis-Cyclometalation of 4,6-Diphenylpyrimidine As a Versatile Route to Rigid Multimetallic Assemblies," Inorganic Chemistry, 2011, vol. 50, No. 13, pp. 6304-6313.

Thapa, P. et al., "2,4-Diaryl Benzofuro[3,2-b]pyridine Derivatives: Design, Synthesis, and Evaluation of Topoisomerase Inhibitory Activity and Cytotoxicity," Bulletin of the Korean Chemical Society, Oct. 7, 2013, vol. 34, No. 10, pp. 3073-3082.

Su, S-J. et al., "RGB Phosphorescent Organic Light-Emitting Diodes by Using Host Materials with Heterocylic Cores:Effect of Nitrogen Atom Orientations," Chemistry of Materials, 2011, vol. 23, No. 2, pp. 274-284.

* cited by examiner

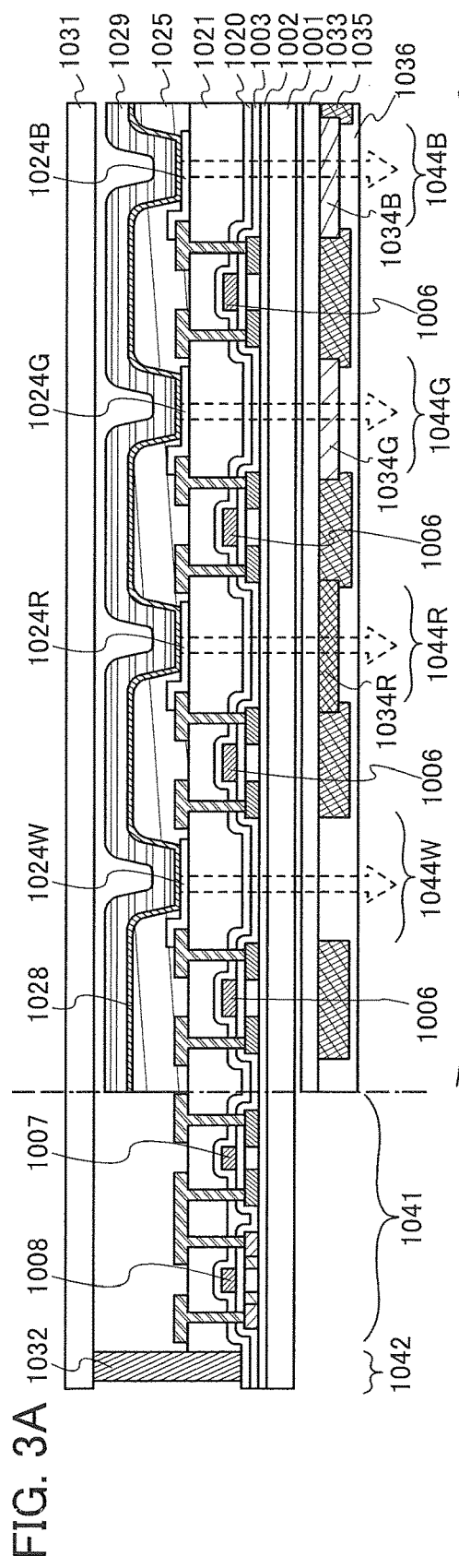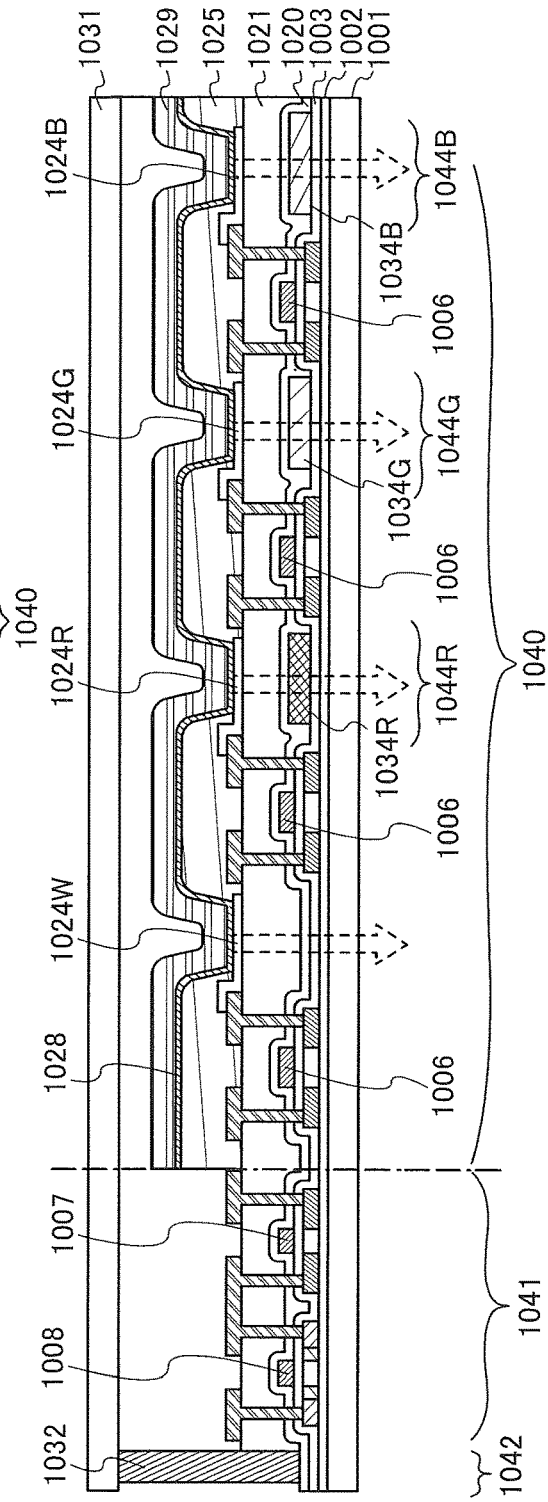

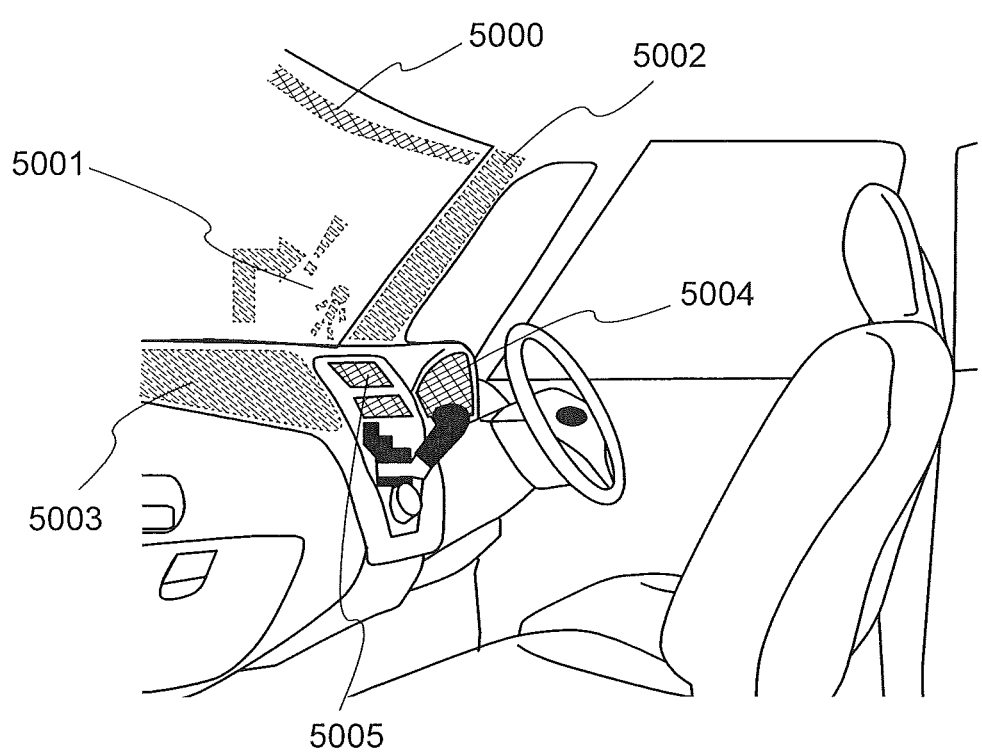

COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to a benzofuropyridine compound or a benzothienopyridine compound. One embodiment of the present invention relates to a light-emitting element in which a light-emitting layer capable of emitting light by application of an electric field is provided between a pair of electrodes, and also relates to a display device, an electronic device, a semiconductor device, and a lighting device each including the light-emitting element.

Note that one embodiment of the present invention is not limited to the above technical field. One embodiment of the present invention relates to an object, a method, and a manufacturing method. In addition, one embodiment of the present invention relates to a process, a machine, manufacture, and a composition of matter. In particular, one embodiment of the present invention relates to a semiconductor device, a display device, a light-emitting device, a lighting device, driving methods thereof, and manufacturing methods thereof. In particular, one embodiment of the present invention may further include an organometallic complex.

2. Description of the Related Art

In recent years, a light-emitting element using a light-emitting organic compound or inorganic compound as a light-emitting material has been actively developed. In particular, a light-emitting element called an electroluminescence (EL) element has attracted attention as a next-generation flat panel display element because it has a simple structure in which a light-emitting layer containing a light-emitting material is provided between electrodes, and characteristics such as feasibility of being thinner and more lightweight and responsive to input signals and capability of driving with direct current at a low voltage. In addition, a display using such a light-emitting element has a feature that it is excellent in contrast and image quality, and has a wide viewing angle. Further, since such a light-emitting element is a plane light source, the light-emitting element is considered applicable to a light source such as a backlight of a liquid crystal display and an illumination device.

In the case where the light-emitting substance is an organic compound having a light-emitting property, the emission mechanism of the light-emitting element is a carrier-injection type. Specifically, by applying a voltage with a light-emitting layer provided between electrodes, electrons and holes injected from the electrodes recombine to raise the light-emitting substance to an excited state, and light is emitted when the substance in the excited state returns to the ground state. There are two types of the excited states: a singlet excited state ($S^*$) and a triplet excited state ($T^*$). In addition, the statistical generation ratio thereof in a carrier-injection type light-emitting element is considered to be $S^*:T^*=1:3$.

In general, the ground state of a light-emitting organic compound is a singlet state. Light emission from a singlet excited state ($S^*$) is referred to as fluorescence where electron transition occurs between the same multiplicities. In contrast, light emission from a triplet excited state ($T^*$) is referred to as phosphorescence where electron transition occurs between different multiplicities. Here, in a compound emitting fluorescence (hereinafter referred to as a fluorescent compound), in general, phosphorescence cannot be observed at room temperature, and only fluorescence can be observed. Accordingly, the internal quantum efficiency (the ratio of generated photons to injected carriers) in a light-emitting element using a fluorescent compound is assumed to have a theoretical limit of 25% based on $S^*:T^*=1:3$.

In contrast, the use of a phosphorescent compound can increase the internal quantum efficiency to 100% in theory. In other words, emission efficiency can be 4 times as much as that of the fluorescent compound. For these reasons, in order to obtain a highly efficient light-emitting element, a light-emitting element using a phosphorescent compound has been developed actively recently. As the phosphorescent compound, an organometallic complex that has iridium or the like as a central metal have particularly attracted attention because of their high phosphorescence quantum yield. For example, an organometallic complex that has iridium as a central metal is disclosed as a phosphorescent material in Patent Documents 1 and 2.

An advantage of the use of the highly efficient light-emitting element is that power consumption of an electronic device using the light-emitting element can be reduced, for example. Energy issues have been discussed recently, and power consumption is becoming a major factor which affects consumer buying patterns; thus, power consumption is a very important element.

However, an energy level at which phosphorescence is emitted, a triplet excitation level, is located lower than a singlet excitation level with which fluorescence is emitted in terms of energy. Therefore, for a phosphorescent light-emitting element to obtain light having the same wavelength as a fluorescent light-emitting element, the phosphorescent light-emitting element needs a host material and a carrier-transport material which have a wider energy gap. However, such materials have not been well developed as compared with other materials.

Moreover, even with such a material having a wide energy gap, inherent emission efficiency of a phosphorescent element cannot be always achieved, and driving voltage increases in some cases depending on a combination of materials used in the layers.

In view of the above, in recent years, carbazole compounds, for example, have attracted attention as compounds having a wide energy gap. Patent Document 3 discloses a light-emitting element in which a carbazole compound is used for a host material in a light-emitting layer and a hole-transport layer. Patent Document 4 discloses a material having two carbazole skeletons.

REFERENCE

Patent Document

[Patent Document 1] PCT International Publication No. WO 00/70655
[Patent Document 2] Japanese Published Patent Application No. 2013-53158
[Patent Document 3] Japanese Published Patent Application No. 2013-33958
[Patent Document 4] PCT International Publication No. WO 13/105206

SUMMARY OF THE INVENTION

Although use of light-emitting elements capable of emitting phosphorescence can save power consumption, a further reduction in power consumption and a reduction in driving voltage are required. Not only a reduction in power consumption but also high reliability and a long lifetime which enable long-term use of a light-emitting element, high color purity for producing great color, and the like are required for the light-emitting element. Thus, a phosphorescent material is also needed to have such performances.

In view of the above, an object of one embodiment of the present invention is to provide a novel substance that can be used in an element capable of emitting phosphorescence. Another object is to provide a novel substance that contributes to high emission efficiency. Another object is to provide a novel substance that contributes to light emission with high color purity. Another object is to provide a novel substance that is used in an element capable of emitting blue phosphorescence. Another object is to provide a novel substance. Another object is to provide a light-emitting element, a light-emitting device, an electronic device, or a lighting device including the novel substance.

Another object is to provide a source material (precursor) for synthesizing the novel substance.

Another object is to provide a light-emitting element, a light-emitting device, an electronic device, or a lighting device with high emission efficiency. Another object is to provide a highly reliable light-emitting element, light-emitting device, electronic device, or lighting device. Another object is to provide a light-emitting element, a light-emitting device, an electronic device, or a lighting device with low power consumption. Another object is to provide a novel light-emitting element, light-emitting device, electronic device, or lighting device.

Note that the descriptions of these objects do not disturb the existence of other objects. In one embodiment of the present invention, there is no need to achieve all the objects. Other objects will be apparent from and can be derived from the description of the specification, the drawings, the claims, and the like.

One embodiment of the present invention is a light-emitting element including a pair of electrodes and an EL layer between the pair of electrodes. The EL layer includes a substance having a carbazole skeleton. The substance having a carbazole skeleton is bonded to a substituted or unsubstituted first arylene group through a nitrogen atom included in the carbazole skeleton. The first arylene group is bonded to a substituted or unsubstituted benzofuropyridyl group or a substituted or unsubstituted benzothienopyridyl group. The first arylene group includes 1 to 5 substituted or unsubstituted second arylene groups which are bonded to one another. The carbazole skeleton is bonded to the benzofuropyridyl group or the benzothienopyridyl group through the first arylene group.

In the light-emitting element of one embodiment of the present invention, the EL layer may include a layer containing an emission center substance. The EL layer may include a layer containing an iridium compound.

Another embodiment of the present invention is a compound represented by General Formula (G1).

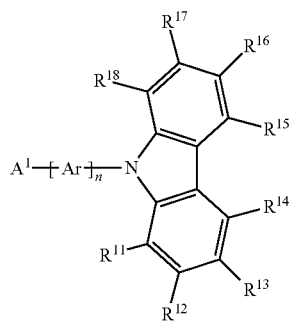

(G1)

In General Formula (G1), $A^1$ represents a substituted or unsubstituted benzofuropyridyl group or a substituted or unsubstituted benzothienopyridyl group; Ar represents a substituted or unsubstituted arylene group having 6 to 13 carbon atoms; each of $R^{11}$ to $R^{18}$ independently represents hydrogen, a substituted or unsubstituted alkyl group having 1 to 6 carbon atoms, or a substituted or unsubstituted aryl group having 6 to 13 carbon atoms; and n represents a natural number of 1 to 5.

Another embodiment of the present invention is a compound represented by General Formula (G2-1).

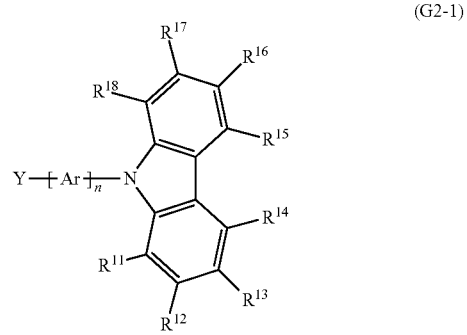

(G2-1)

In General Formula (G2-1), Ar represents a substituted or unsubstituted arylene group having 6 to 13 carbon atoms; each of $R^{11}$ to $R^{18}$ independently represents hydrogen, a substituted or unsubstituted alkyl group having 1 to 6 carbon atoms, or a substituted or unsubstituted aryl group having 6 to 13 carbon atoms; and n represents a natural number of 1 to 5. In addition, Y in General Formula (G2-1) is represented by General Formula (G2-2).

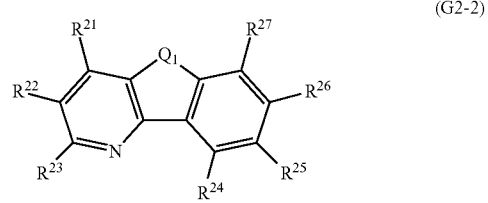

(G2-2)

In General Formula (G2-2), one of $R^{21}$ to $R^{27}$ represents a single bond between Ar and Y in General Formula (G2-1); each of the others of $R^{21}$ to $R^{27}$ independently represents hydrogen, a substituted or unsubstituted alkyl group having 1 to 6 carbon atoms, or a substituted or unsubstituted aryl group having 6 to 13 carbon atoms; and $Q^1$ represents an oxygen atom or a sulfur atom.

Another embodiment of the present invention is a compound represented by General Formula (G3-1).

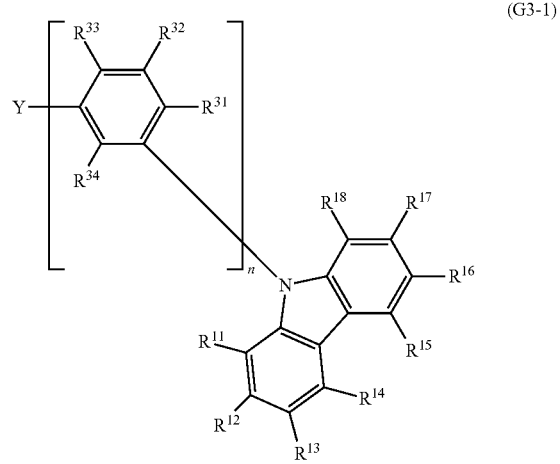

(G3-1)

In General Formula (G3-1), each of $R^{11}$ to $R^{18}$ and $R^{31}$ to $R^{34}$ independently represents hydrogen, a substituted or unsubstituted alkyl group having 1 to 6 carbon atoms, or a substituted or unsubstituted aryl group having 6 to 13 carbon atoms; and n represents a natural number of 1 to 5. In addition, Y in General Formula (G3-1) is represented by General Formula (G3-2).

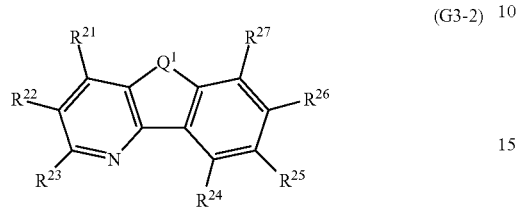

(G3-2)

In General Formula (G3-2), one of $R^{21}$ to $R^{27}$ represents a single bond between a phenylene skeleton and Y in General Formula (G3-1); each of the others of $R^{21}$ to $R^{27}$ independently represents hydrogen, a substituted or unsubstituted alkyl group having 1 to 6 carbon atoms, or a substituted or unsubstituted aryl group having 6 to 13 carbon atoms; and $Q^1$ represents an oxygen atom or a sulfur atom.

Another embodiment of the present invention is a compound represented by General Formula (G4-1).

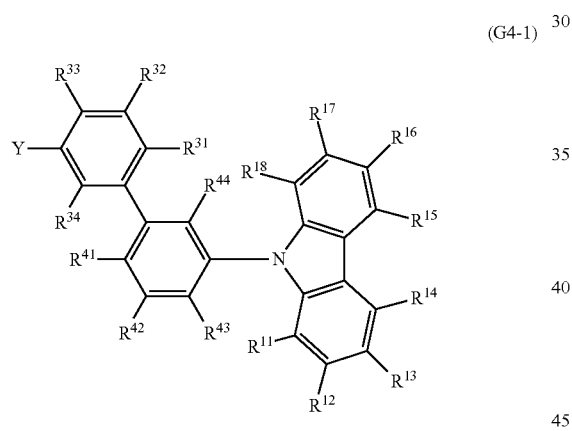

(G4-1)

In General Formula (G4-1), each of $R^{11}$ to $R^{18}$, $R^{31}$ to $R^{34}$, and $R^{41}$ to $R^{44}$ independently represents hydrogen, a substituted or unsubstituted alkyl group having 1 to 6 carbon atoms, or a substituted or unsubstituted aryl group having 6 to 13 carbon atoms. In addition, Y in General Formula (G4-1) is represented by General Formula (G4-2).

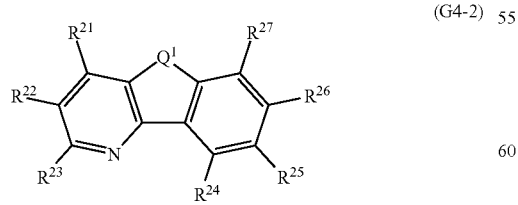

(G4-2)

In General Formula (G4-2), one of $R^{21}$ to $R^{27}$ represents a single bond between a phenylene skeleton and Y in General Formula (G4-1); each of the others of $R^{21}$ to $R^{27}$ independently represents hydrogen, a substituted or unsubstituted alkyl group having 1 to 6 carbon atoms, or a substituted or unsubstituted aryl group having 6 to 13 carbon atoms; and $Q^1$ represents an oxygen atom or a sulfur atom.

In the compound of one embodiment of the present invention, any one of $R^{25}$, $R^{27}$, and $R^{21}$ may represent a single bond between Y and the phenylene skeleton.

Another embodiment of the present invention is a compound represented by Chemical Formula (112).

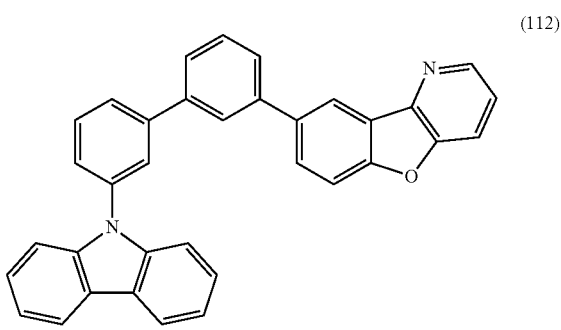 [SMILES: c1cc(-c2cccc(-n3c4ccccc4c4ccccc43)c2)cc(-c2ccc3oc4cccnc4c3c2)c1]

(112)

Another embodiment of the present invention is a compound represented by Chemical Formula (122).

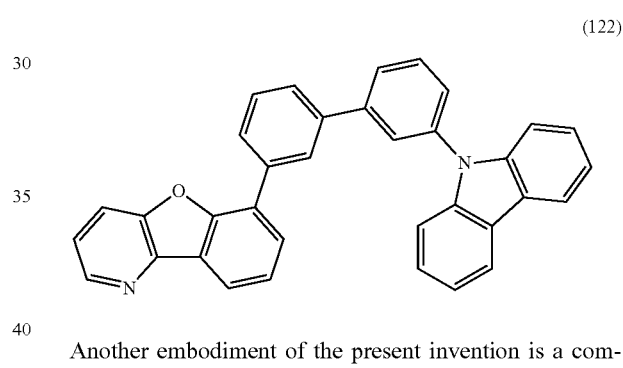

(122)

Another embodiment of the present invention is a compound represented by Chemical Formula (134).

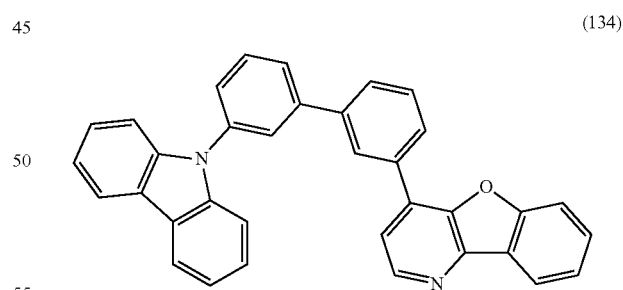

(134)

Another embodiment of the present invention is an electronic device including a pair of electrodes and an organic layer between the pair of electrodes. The organic layer contains the compound of one embodiment of the present invention. Another embodiment of the present invention is a light-emitting element including a pair of electrodes and an EL layer between the pair of electrodes. The EL layer contains the compound of one embodiment of the present invention.

In the light-emitting element of one embodiment of the present invention, the EL layer may further include an emission center substance. The EL layer may further include an iridium complex. Another embodiment of the present invention is a display module including the light-emitting element of one embodiment of the present invention, a driver, and an FPC. Another embodiment of the present invention is a lighting module including the light-emitting element of one embodiment of the present invention and a container for the light-emitting element. Another embodiment of the present invention is a light-emitting device including the light-emitting element of one embodiment of the present invention and a unit configured to control the light-emitting element. Another embodiment of the present invention is a display device including the light-emitting element of one embodiment of the present invention in a display portion and a unit configured to control the light-emitting element. Another embodiment of the present invention is a lighting device including the light-emitting element of one embodiment of the present invention in a lighting portion and a unit configured to control the light-emitting element. Another embodiment of the present invention is an electronic device including the light-emitting element of one embodiment of the present invention and an operation switch.

Another embodiment of the present invention is a compound represented by General Formula (G5).

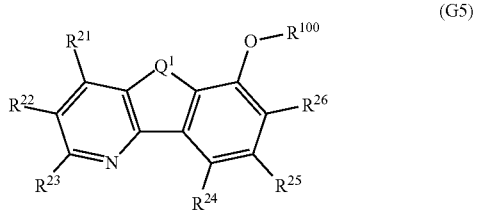
(G5)

In General Formula (G5), each of $R^{21}$ to $R^{26}$ independently represents hydrogen, a substituted or unsubstituted alkyl group having 1 to 6 carbon atoms, or a substituted or unsubstituted aryl group having 6 to 13 carbon atoms; $Q^1$ represents an oxygen atom or a sulfur atom; and $R^{100}$ represents a triflate group, a mesylate group, or a monochlate group.

Another embodiment of the present invention is a compound represented by Chemical Formula (400).

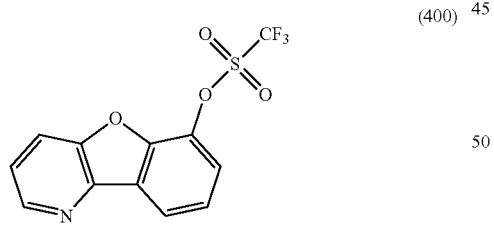
(400)

Another embodiment of the present invention is a compound represented by General Formula (G6).

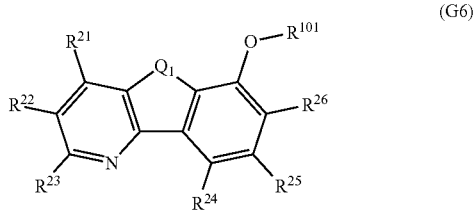
(G6)

In General Formula (G6), each of $R^{21}$ to $R^{26}$ independently represents hydrogen, a substituted or unsubstituted alkyl group having 1 to 6 carbon atoms, or a substituted or unsubstituted aryl group having 6 to 13 carbon atoms; $Q^1$ represents an oxygen atom; and $R^{101}$ represents a substituted or unsubstituted alkyl group having 1 to 6 carbon atoms.

Another embodiment of the present invention is a compound represented by Chemical Formula (410).

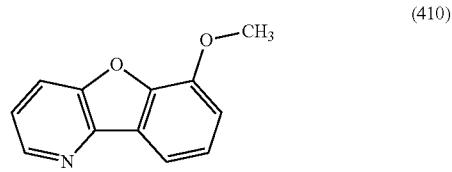
(410)

Another embodiment of the present invention is a compound represented by General Formula (G7).

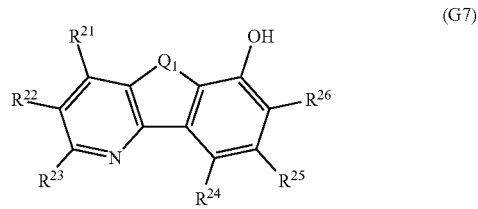
(G7)

In General Formula (G7), each of $R^{21}$ to $R^{26}$ independently represents hydrogen, a substituted or unsubstituted alkyl group having 1 to 6 carbon atoms, or a substituted or unsubstituted aryl group having 6 to 13 carbon atoms; and $Q^1$ represents an oxygen atom or a sulfur atom.

Another embodiment of the present invention is a compound represented by Chemical Formula (420).

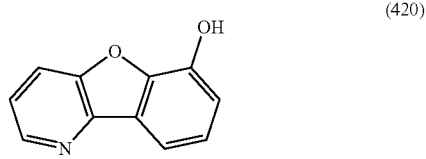 [SMILES: Oc1cccc2c1oc1cccnc12]
(420)

Another embodiment of the present invention is a compound represented by General Formula (G7).

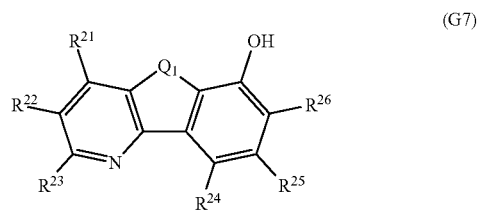
(G7)

In General Formula (G7), each of $R^{22}$ to $R^{27}$ independently represents hydrogen, a substituted or unsubstituted alkyl group having 1 to 6 carbon atoms, or a substituted or unsubstituted aryl group having 6 to 13 carbon atoms; $Q^1$ represents an oxygen atom or a sulfur atom; and X represents a halogen.

Another embodiment of the present invention is a compound represented by Chemical Formula (430).

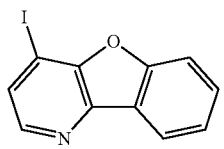

(430)

With one embodiment of the present invention, a novel substance that can be used in an element capable of emitting phosphorescence can be provided. A novel substance that contributes to high emission efficiency can be provided. A novel substance that contributes to light emission with high color purity can be provided. A novel substance that is used in an element capable of emitting blue phosphorescence can be provided. A novel substance can be provided. A light-emitting element, a light-emitting device, an electronic device, or a lighting device including the novel substance can be provided.

In addition, a source material (precursor) for synthesizing the novel substance can be provided.

Alternatively, a light-emitting element, a light-emitting device, an electronic device, or a lighting device with high emission efficiency can be provided. Alternatively, a light-emitting element, a light-emitting device, an electronic device, or a lighting device with high reliability can be provided. Alternatively, a light-emitting element, a light-emitting device, an electronic device, or a lighting device with low power consumption can be provided. Alternatively, a novel light-emitting element, a novel light-emitting device, a novel electronic device, or a novel lighting device can be provided.

Note that the description of these effects does not disturb the existence of other effects. One embodiment of the present invention does not necessarily achieve all the effects listed above. Other effects will be apparent from and can be derived from the description of the specification, the drawings, the claims, and the like.

BRIEF DESCRIPTION OF THE DRAWINGS

FIGS. 3A and 3B are conceptual diagrams of active matrix light-emitting devices.

FIG. 10 illustrates in-vehicle display devices and lighting devices.

DETAILED DESCRIPTION OF THE INVENTION

Figure 1A:
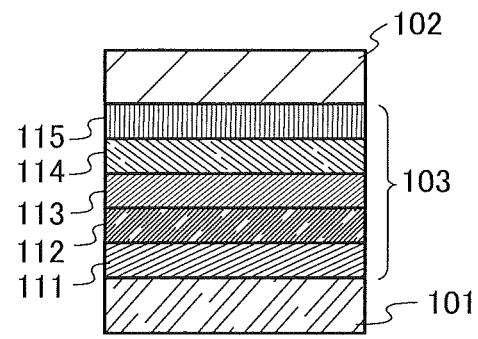
FIGS. 1A and 1B are conceptual diagrams of light-emitting elements.

Embodiments of the present invention will be described below. Note that it is easily understood by those skilled in the art that modes and details disclosed herein can be modified in various ways without departing from the spirit and scope of the present invention. Therefore, the present invention is not construed as being limited to the description of the following embodiments.

Note that in each drawing described in this specification, the size, the thickness, and the like of components such as an anode, an EL layer, an intermediate layer, and a cathode are exaggerated for clarity in some cases. Therefore, the sizes of the components are not limited to the sizes in the drawings and relative sizes between the components.

In this specification and the like, ordinal numbers such as "first", "second", and "third" are used for convenience and do not denote the order of steps or the stacking order of layers. Therefore, for example, description can be made even when "first" is replaced with "second" or "third", as appropriate. In addition, the ordinal numbers in this specification and the like are not necessarily the same as those which specify one embodiment of the present invention.

The structures of the present invention described in this specification and the like, the same portions or portions having similar functions in different drawings are denoted by the same reference numerals, and description of such portions is not repeated. Furthermore, the same hatching pattern is applied to portions having similar functions, and the portions are not especially denoted by reference numerals in some cases.

In this specification, color is defined by three aspects of hue (corresponding to the wavelength of light of a single color), chroma (saturation, i.e., the degree to which it differs from white), and value (brightness, i.e., the intensity of light). In this specification, color may be defined by only one of the above three aspects or two of the aspects which are selected arbitrarily. In this specification, a difference between two colors of light means a difference in at least one of the above three aspects and includes a difference in the shapes of two spectra of light or in the distributions of the relative intensity of the peaks in the spectra.

Note that the terms "film" and "layer" can be interchanged with each other depending on the case or circumstances. For example, the term "conductive layer" can be changed into the term "conductive film" in some cases, and the term "insulating film" can be changed into the term "insulating layer" in some cases.

Embodiment 1

A compound of one embodiment of the present invention described in this embodiment has a structure in which a carbazole skeleton is bonded to a benzofuropyridyl group or a benzothienopyridyl group through an arylene group. The compound with such a structure excels at transporting carriers (particularly electrons). Owing to this, a light-emitting element driven at low voltage can be provided.

The compound can have a high T1 level, and thus can be suitably used for a light-emitting element including an emission center substance that emits phosphorescence. Specifically, the high T1 level of the compound can inhibit transfer of excitation energy of the phosphorescent substance to the compound, which leads to efficient conversion of excitation energy into light emission. A typical example of the phosphorescent substance is an iridium complex.

A preferable example of the compound with the above structure is represented by General Formula (G1).

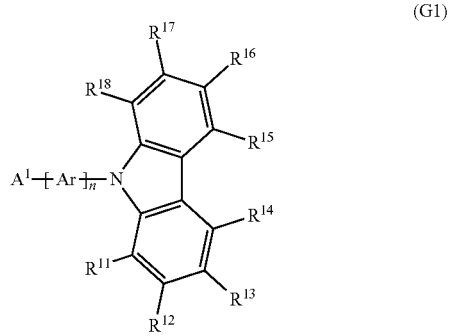

(G1)

In General Formula (G1), $A^1$ represents a substituted or unsubstituted benzofuropyridyl group or a substituted or unsubstituted benzothienopyridyl group; Ar represents a substituted or unsubstituted arylene group having 6 to 13 carbon atoms; each of $R^{11}$ to $R^{18}$ independently represents hydrogen, a substituted or unsubstituted alkyl group having 1 to 6 carbon atoms, or a substituted or unsubstituted aryl group having 6 to 13 carbon atoms; and n represents a natural number of 1 to 5.

The benzofuropyridyl group and the benzothienopyridyl group have a favorable electron-transport property, and can be used for an electron-transport layer or a light-emitting layer.

A more preferred specific example of the compound described in this embodiment is represented by General Formula (G2-1).

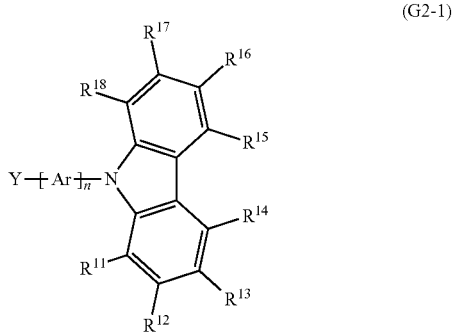

(G2-1)

In General Formula (G2-1), Ar represents a substituted or unsubstituted arylene group having 6 to 13 carbon atoms; each of $R^{11}$ to $R^{18}$ independently represents hydrogen, a substituted or unsubstituted alkyl group having 1 to 6 carbon atoms, or a substituted or unsubstituted aryl group having 6 to 13 carbon atoms; and n represents a natural number of 1 to 5. In addition, Y in General Formula (G2-1) is represented by General Formula (G2-2).

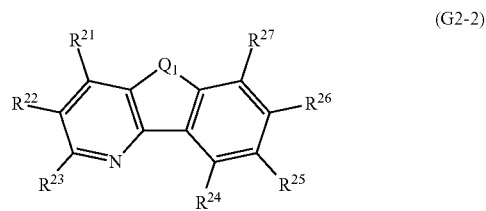

(G2-2)

In General Formula (G2-2), one of $R^{21}$ to $R^{27}$ represents a single bond between Y and Ar in General Formula (G2-1); each of the others of $R^{21}$ to $R^{27}$ independently represents hydrogen, a substituted or unsubstituted alkyl group having 1 to 6 carbon atoms, or a substituted or unsubstituted aryl group having 6 to 13 carbon atoms; and $Q^1$ represents an oxygen atom or a sulfur atom.

A more preferred specific example of the compound described in this embodiment is represented by General Formula (G3-1).

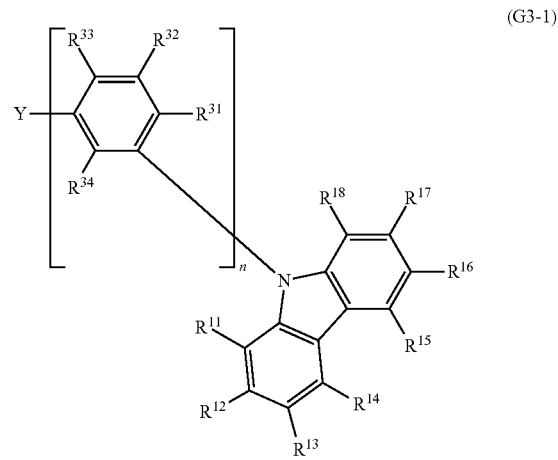

(G3-1)

In General Formula (G3-1), each of $R^{11}$ to $R^{18}$ and $R^{31}$ to $R^{34}$ independently represents hydrogen, a substituted or unsubstituted alkyl group having 1 to 6 carbon atoms, or a substituted or unsubstituted aryl group having 6 to 13 carbon atoms; and n represents a natural number of 1 to 5. In addition, Y in General Formula (G3-1) is represented by General Formula (G3-2).

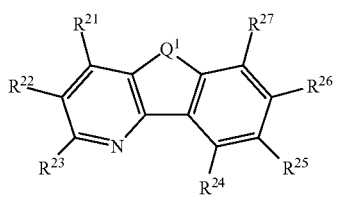

(G3-2)

In General Formula (G3-2), one of $R^{21}$ to $R^{27}$ represents a single bond between a phenylene skeleton and Y in General Formula (G3-1); each of the others of $R^{21}$ to $R^{27}$ independently represents hydrogen, a substituted or unsubstituted alkyl group having 1 to 6 carbon atoms, or a substituted or unsubstituted aryl group having 6 to 13 carbon atoms; and $Q^1$ represents an oxygen atom or a sulfur atom.

A more preferred specific example of the compound described in this embodiment is represented by General Formula (G4-1).

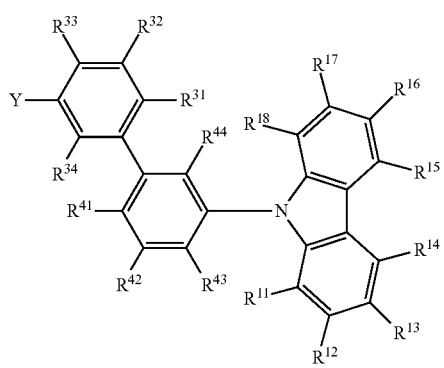

(G4-1)

In General Formula (G4-1), each of $R^{11}$ to $R^{18}$, $R^{31}$ to $R^{34}$, and $R^{41}$ to $R^{44}$ independently represents hydrogen, a substituted or unsubstituted alkyl group having 1 to 6 carbon atoms, or a substituted or unsubstituted aryl group having 6 to 13 carbon atoms. In addition, Y in General Formula (G4-1) is represented by General Formula (G4-2).

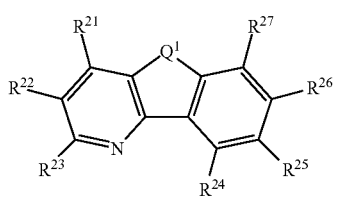

(G4-2)

In General Formula (G4-2), one of $R^{21}$ to $R^{27}$ represents a single bond between a phenylene skeleton and Y in General Formula (G4-1); each of the others of $R^{21}$ to $R^{27}$ independently represents hydrogen, a substituted or unsubstituted alkyl group having 1 to 6 carbon atoms, or a substituted or unsubstituted aryl group having 6 to 13 carbon atoms; and $Q^1$ represents an oxygen atom or a sulfur atom.

Note that one of $R^{25}$ and $R^{27}$ may represent a single bond between Y and the phenylene skeleton.

Note that in General Formula (G1), General Formula (G2-1), and General Formula (G3-1), when n is 2 or more, a plurality of arylene groups may be different arylene groups.

Specific examples of the alkyl group having 1 to 6 carbon atoms include a methyl group, an ethyl group, a propyl group, an isopropyl group, an n-butyl group, a sec-butyl group, an isobutyl group, a tert-butyl group, an n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, and a branched or non-branched hexyl group. Specific examples of the aryl group having 6 to 13 carbon atoms include a phenyl group, an o-toluyl group, an in-toluyl group, a p-toluyl group, a mesityl group, an o-biphenyl group, an in-biphenyl group, a p-biphenyl group, a fluorenyl group, and a 9,9-dimethylfluorenyl group. Specific examples of the arylene group having 6 to 13 carbon atoms include an o-phenylene group, an in-phenylene group, a p-phenylene group, a naphthylene group, and a biphenylene group. Each of $R^{11}$ to $R^{18}$, $R^{21}$ to $R^{27}$, $R^{31}$ to $R^{34}$, and $R^{41}$ to $R^{44}$ (hereinafter collectively referred to as R) may be any of the above-mentioned groups to which a substituent is bonded, for example, may be a toluylene group, a mesitylene group, a tert-butylphenylene group, a fluorenylene group, or a silafluorenylene group.

The case where R further includes a substituent is also assumed. As an example of a substituent, an alkyl group having 1 to 6 carbon atoms is given. Specific examples are a methyl group, an ethyl group, a propyl group, an isopropyl group, an n-butyl group, a sec-butyl group, an isobutyl group, a tert-butyl group, an n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, and a branched or non-branched hexyl group, but the substituent is not limited to these. As another example of the substituent, an aryl group having 6 to 13 carbon atoms is given. Specific examples are an o-toluyl group, an m-toluyl group, a p-toluyl group, a mesityl group, a 4-tert-butylphenyl group, a fluorenyl group, and a silafluorenyl group, but the substituent is not limited to these. A plurality of substituents may be bonded, and the kinds of the substituents may be the same or different.

Specific examples of R include hydrogen, a methyl group, an ethyl group, a propyl group, an isopropyl group, a butyl group, a sec-butyl group, an isobutyl group, a tert-butyl group, a phenyl group, an o-biphenyl group, an in-biphenyl group, and a p-biphenyl group. Examples of these groups to which a substituent is bonded include an o-toluyl group, an in-toluyl group, a p-toluyl group, a mesityl group, a 4-tert-butylphenyl group, a fluorenyl group, a 9,9-dimethylfluorenyl group, a 9,9'-spirobifluorenyl group, a silafluorenyl group, a 9,9-dimethylsilafluorenyl group, and a 9,9'-spirobisilafluorenyl group.

Specific structures of R are shown below. However, the structure of R is not limited to these.

(R-1)

-continued
 (R-2)
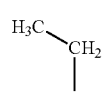 (R-3)
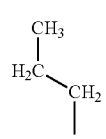 (R-4)
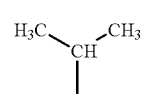 (R-5)
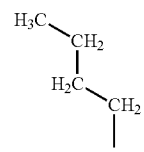 (R-6)
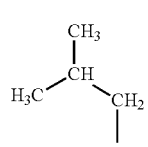 (R-7)
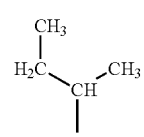 (R-8)
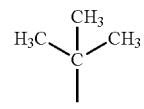 (R-9)
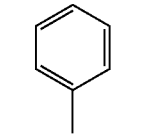 (R-10)
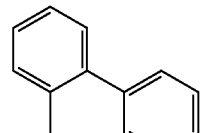 (R-11)
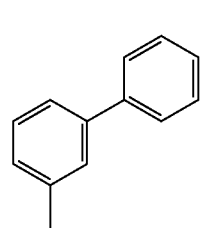 (R-12)
-continued
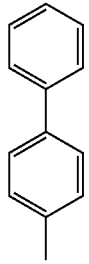 (R-13)
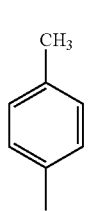 (R-14)
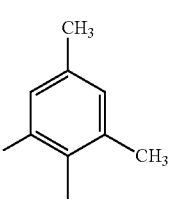 (R-15)
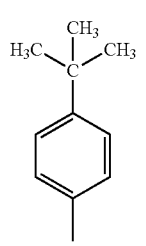 (R-16)
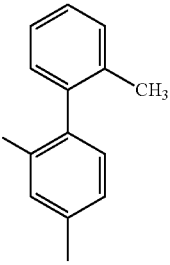 (R-17)
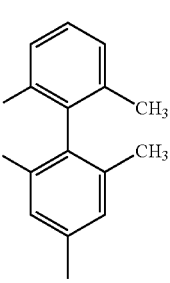 (R-18)

(R-19) 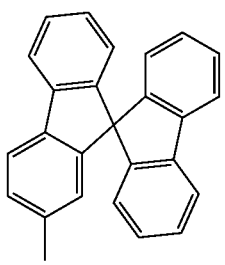
(R-20) 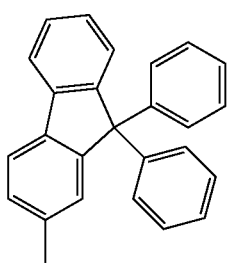
(R-21) 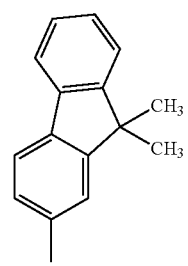
(R-22) 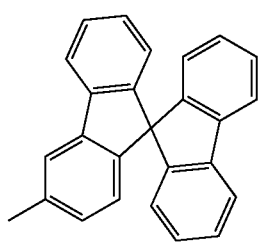
(R-23) 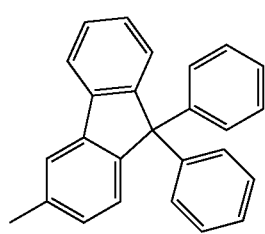
(R-24) 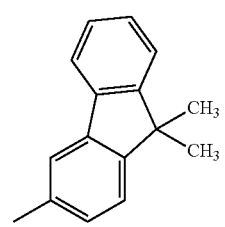
(R-25) 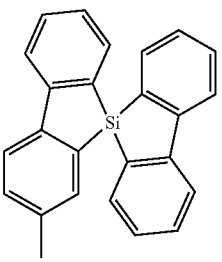
(R-26) 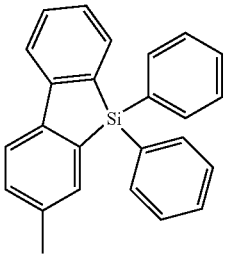
(R-27) 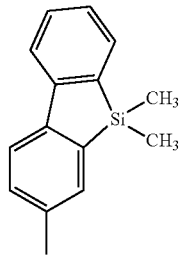
(R-28) 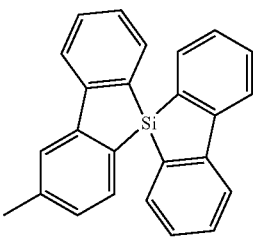
(R-29) 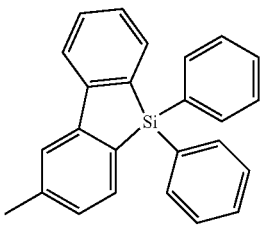
(R-30) 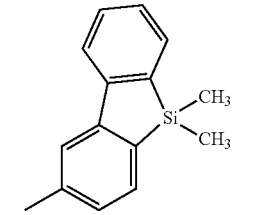
In order that the compound of one embodiment of the present invention has a high T1 level, a structure in which aliphatic hydrocarbon groups are single-bonded or a structure in which six-membered rings are single-bonded are preferable as R to a condensed ring. Alternatively, R may be a structure in which two six-membered rings are bonded to a carbon atom or a silicon atom. Further alternatively, R may be a Spiro ring in which a carbon atom or a silicon atom is centered.

In the case where R is a compound in which two six-membered rings are coupled, ortho substitution or meta substitution like (R-11) or (R-12) is more favorable than para substitution because the T1 level is high. In particular, meta substitution is preferred because it causes smaller influence of steric hindrance and makes synthesis easier than ortho substitution does. In the case where six-membered rings form a condensed ring not directly but through a five-membered ring as in (R-19) to (R-30), (R-22) to (R-24) and (R-28) to (R-30) in each of which a substituent is bonded at the meta position with respect to the coupled portion between two six-membered rings are more favorable than (R-19) to (R-21) and (R-25) to (R-27) in each of which a substituent is bonded at the para position because the meta-substituted compounds have a higher T1 level than the para-substituted compounds.

Next, examples of Ar are described.

Specific examples of Ar include an o-phenylene group, an m-phenylene group, a p-phenylene group, a naphthylene group, and a biphenylene group. Examples of these groups to which a substituent is bonded include a toluylene group, a mesitylene group, a tert-butylphenylene group, a fluorenylene group, a 9,9-dimethylfluorenylene group, a 9,9'-spirobifluorenylene group, a silafluorenylene group, a 9,9-dimethylsilafluorenylene group, and a 9,9'-spirobisilafluorenylene group.

Next, specific examples of Ar are shown below, but Ar is not limited thereto.

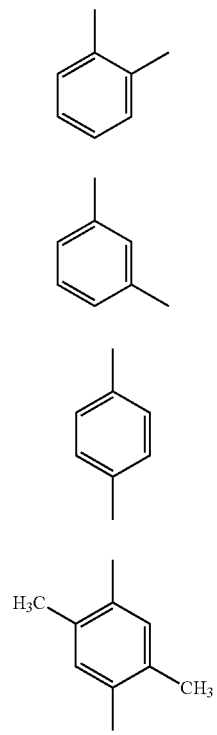

(Ar-1)

(Ar-2)

(Ar-3)

(Ar-4)

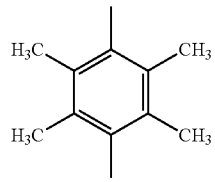

(Ar-5)

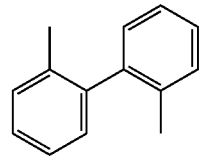

(Ar-6)

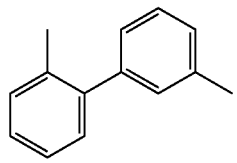

(Ar-7)

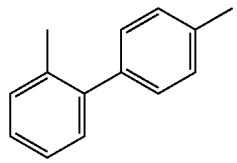

(Ar-8)

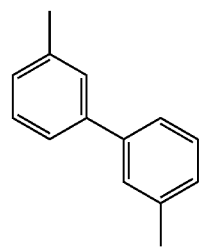

(Ar-9)

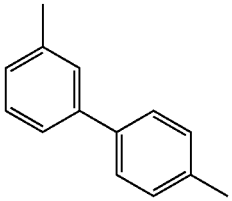

(Ar-10)

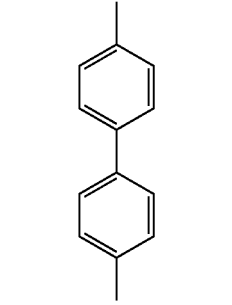

(Ar-11)

(Ar-12) 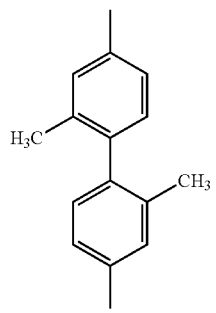
(Ar-13) 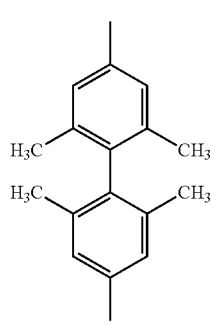
(Ar-14) 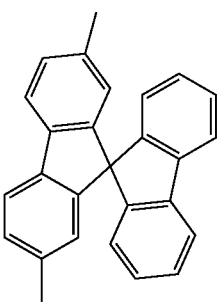
(Ar-15) 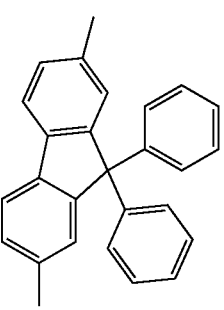
(Ar-16) 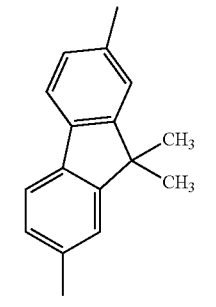
(Ar-17) 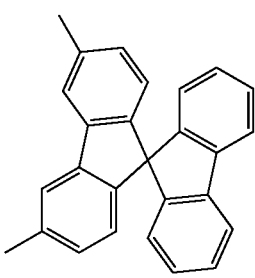
(Ar-18) 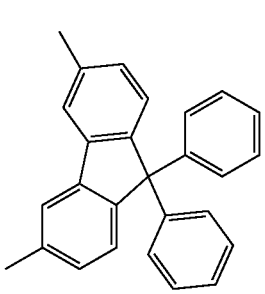
(Ar-19) 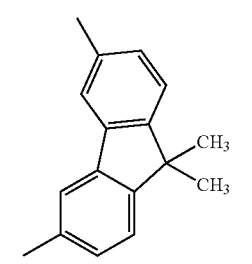
(Ar-20) 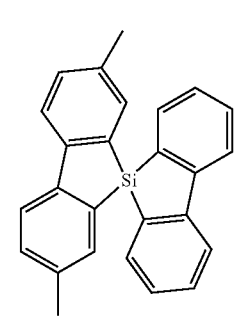
(Ar-21) 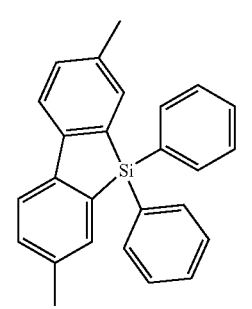

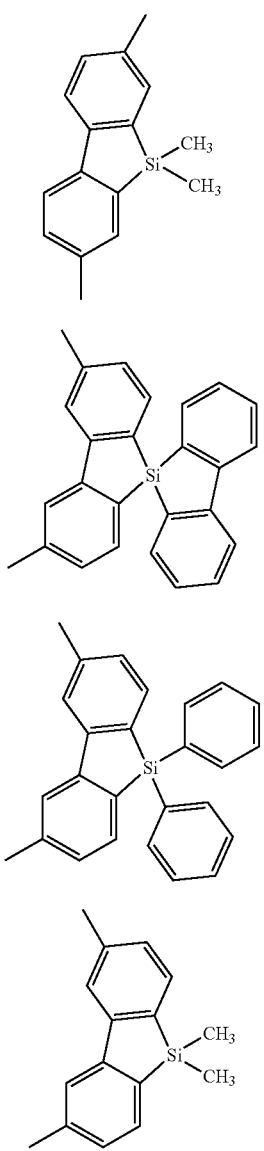

(Ar-22)

(Ar-23)

(Ar-24)

(Ar-25)

In order to increase the T1 level of the compound of one embodiment of the present invention, a structure in which aliphatic hydrocarbon groups are single-bonded or a structure in which six-membered rings are single-bonded is more preferable as Ar than a condensed ring. As shown in (Ar-14) to (Ar-25), Ar may be a structure in which two six-membered rings are bonded through a quaternary carbon atom or a quaternary silicon atom. As shown in (Ar-14), (Ar-17), (Ar-20), and (Ar-23), Ar may be a spiro compound including the carbon atom or the silicon atom as its center. In a compound in which two six-membered rings form a ring through a quaternary carbon atom or a quaternary silicon atom, the six-membered rings position more planar than in a compound in which phenylene groups are just bonded, which makes the structural change between the grounded state and the excited state difficult and thus the T1 level can be kept high.

In the case where Ar is a compound in which two six-membered rings are coupled, ortho substitution or meta substitution like (Ar-11) or (Ar-12) is more favorable than para substitution because the T1 level is high. In particular, meta substitution is preferred because it causes smaller influence of steric hindrance and makes synthesis easier than ortho substitution does. In the case where six-membered rings form a ring as in (Ar-19) to (Ar-30), (Ar-22) to (Ar-24) and (Ar-28) to (Ar-30) in each of which a substituent is bonded at the meta position with respect to the coupled portion between six-membered rings are more favorable than (Ar-19) to (Ar-21) and (Ar-25) to (Ar-27) in each of which a substituent is bonded at the para position because the meta-substituted compounds have a higher T1 level than the para-substituted compounds.

Typical examples of the above-described compounds are shown below. Note that the compounds described in this embodiment are not limited to the examples shown below.

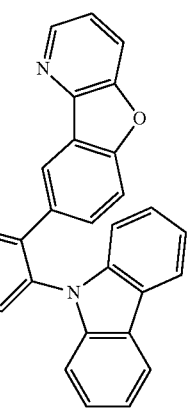

(100)

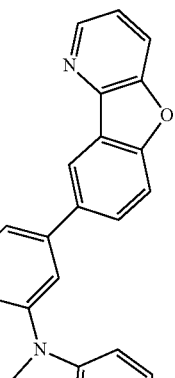

(101)

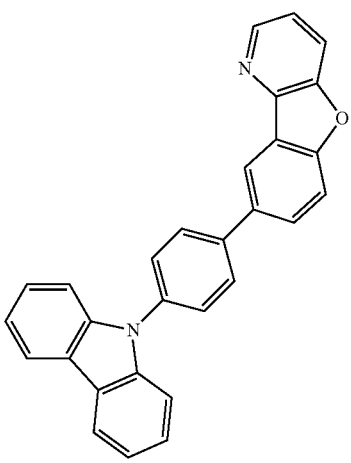

(102)

(103)
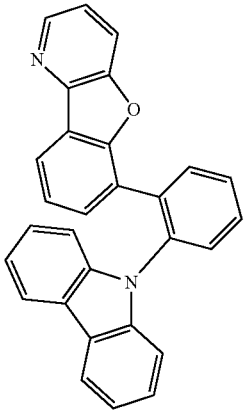
(104)
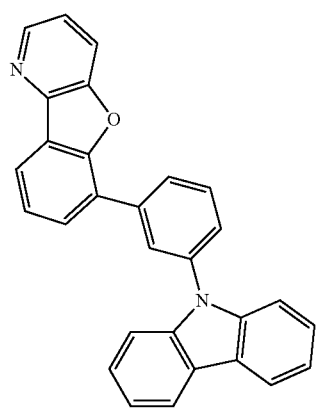
(105)
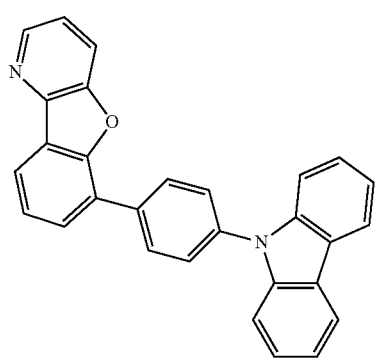
(106)
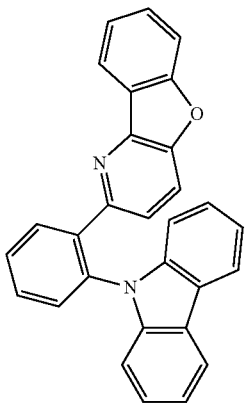
(107)
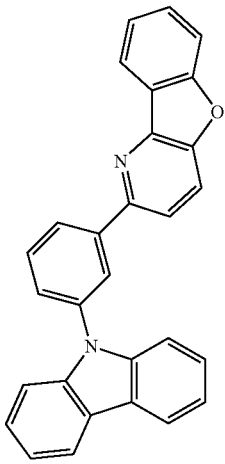
(108)
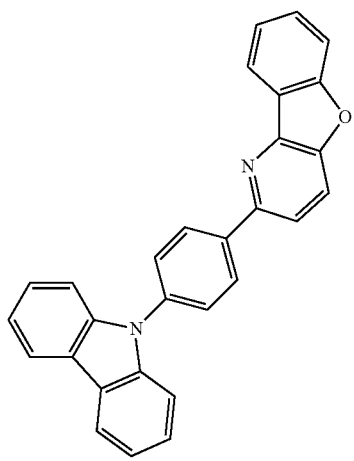
(109)
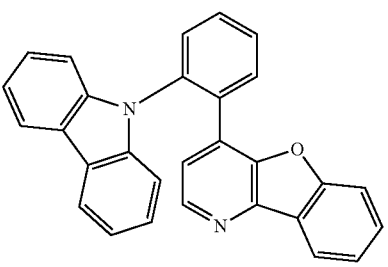
(110)
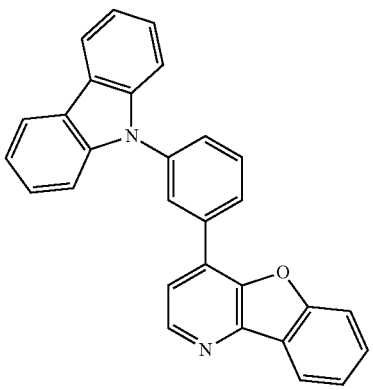

(111)
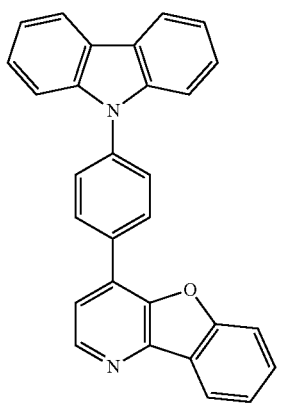
(112)
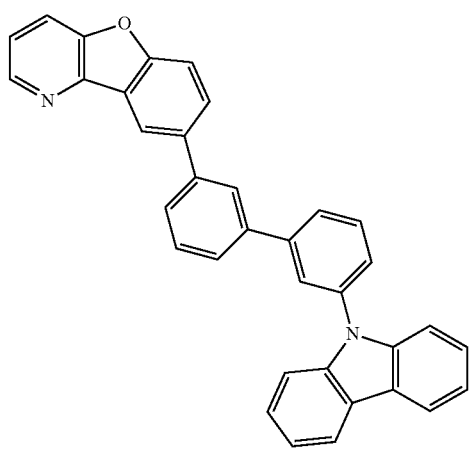
(113)
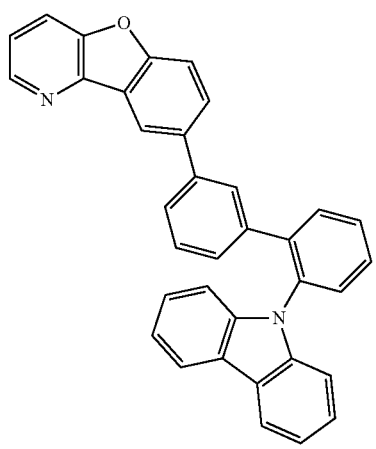
(114)
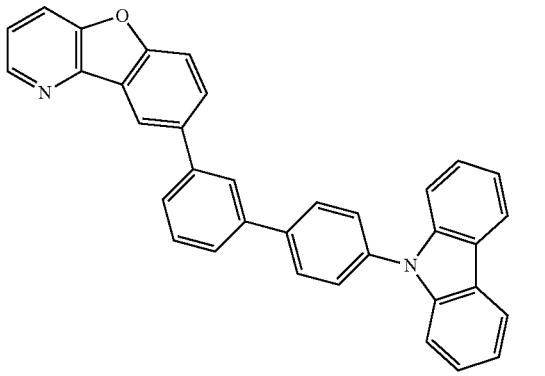
(115)
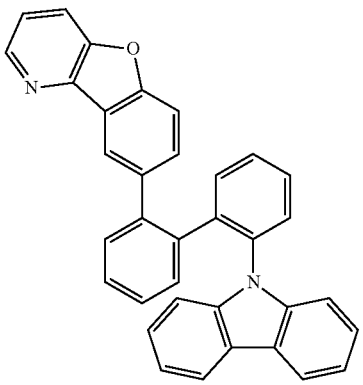
(116)
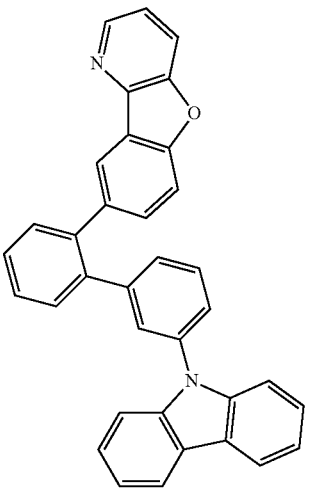

(117) 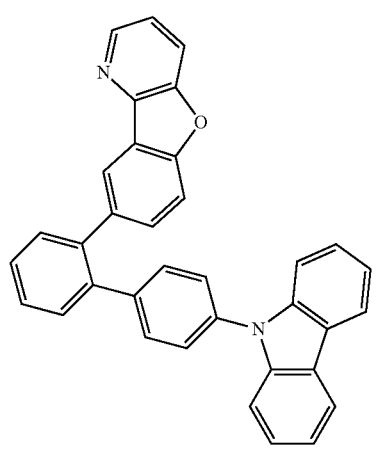
(118) 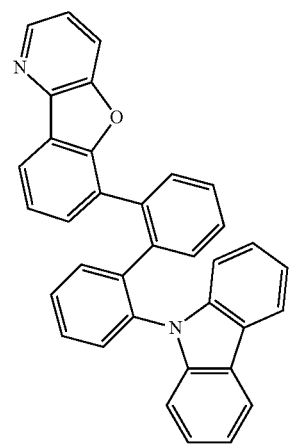
(119) 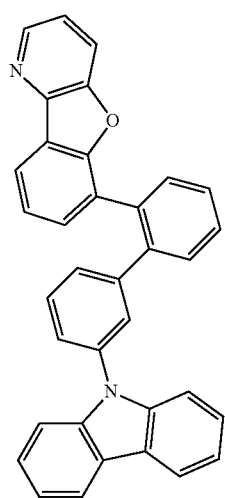
(120) 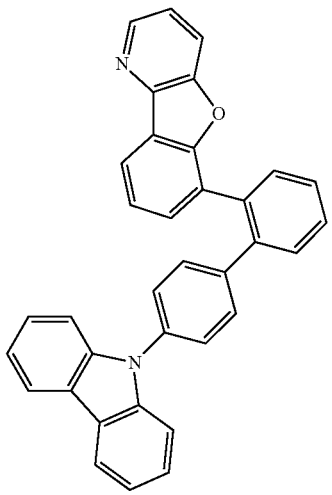
(121)
(122) 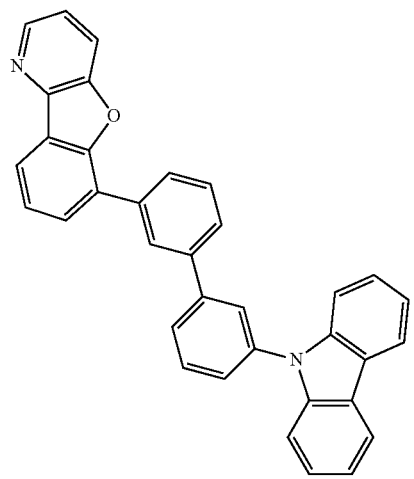

(123)
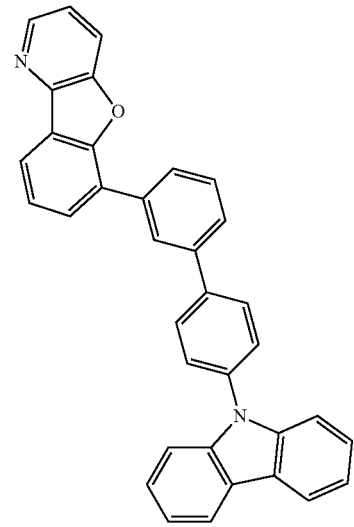
(124)
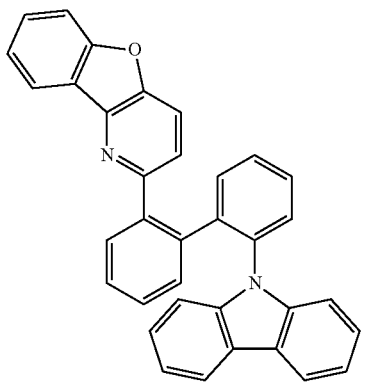
(125)
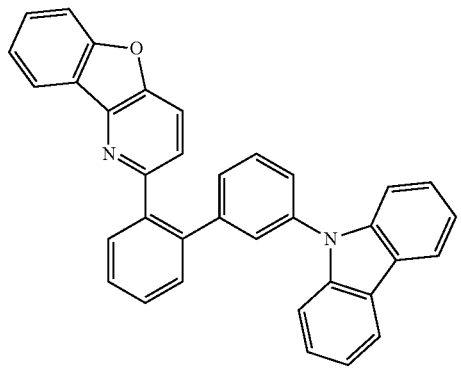
(126)
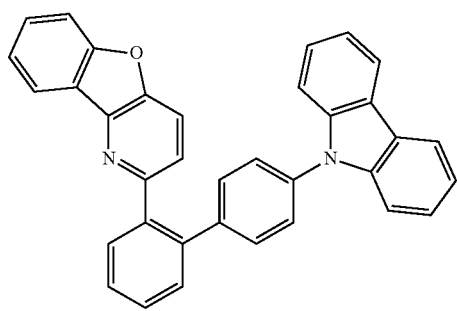
(127)
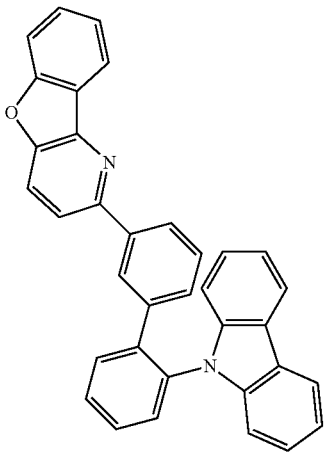
(128)
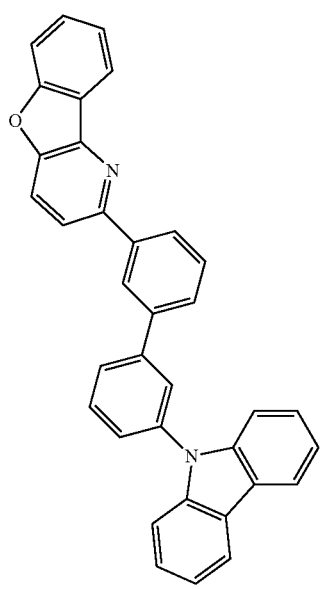
(129)
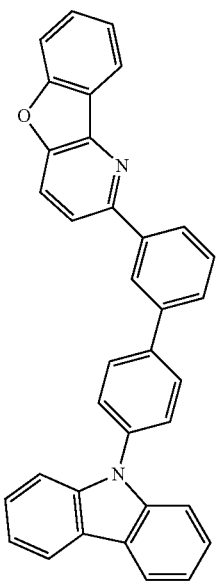

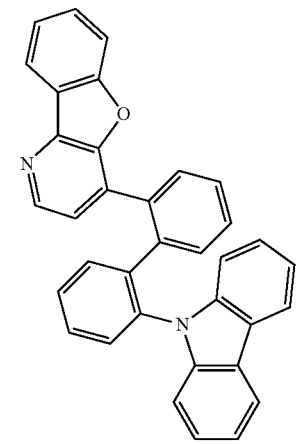
(130)
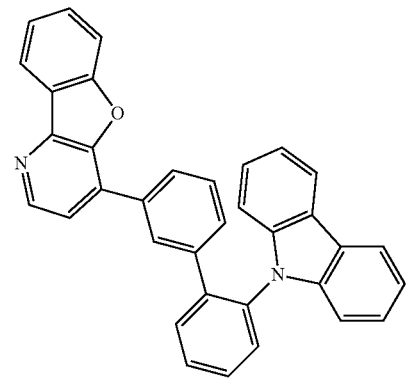
(133)
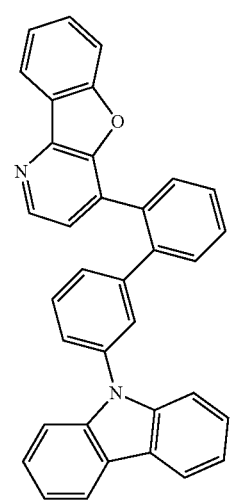
(131)
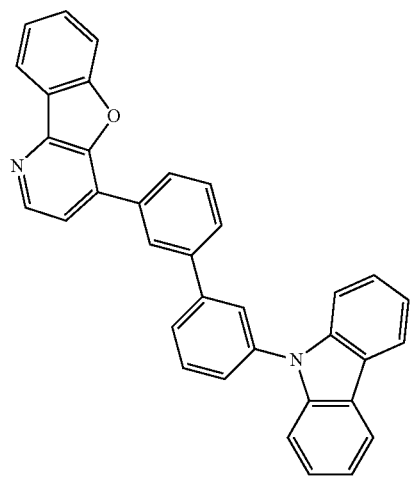
(134)
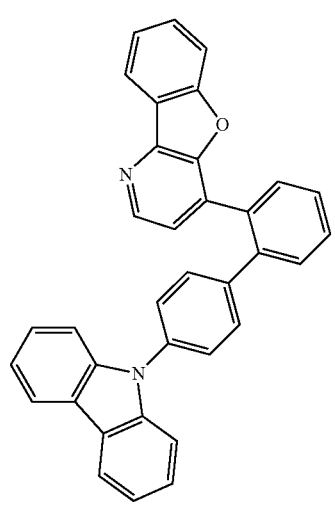
(132)
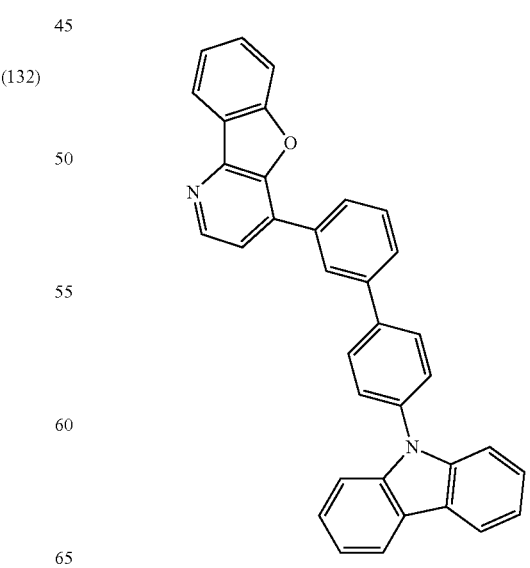
(135)

(136)
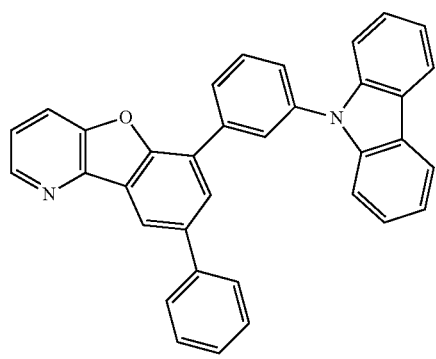
(137)
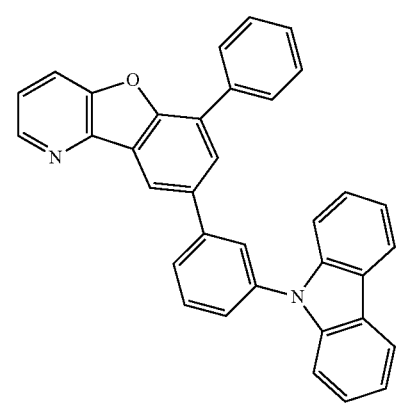
(138)
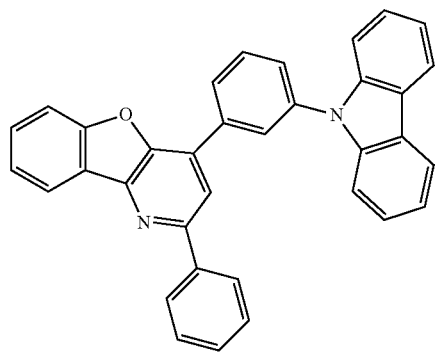
(139)
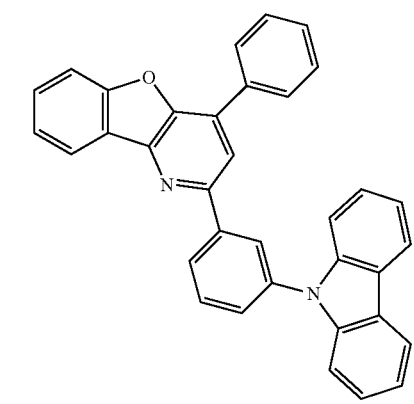
(140)
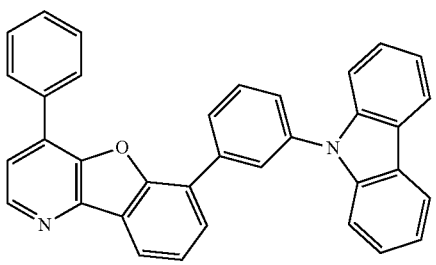
(141)
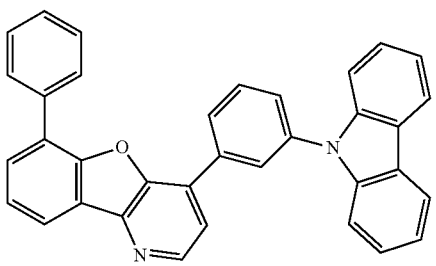
(142)
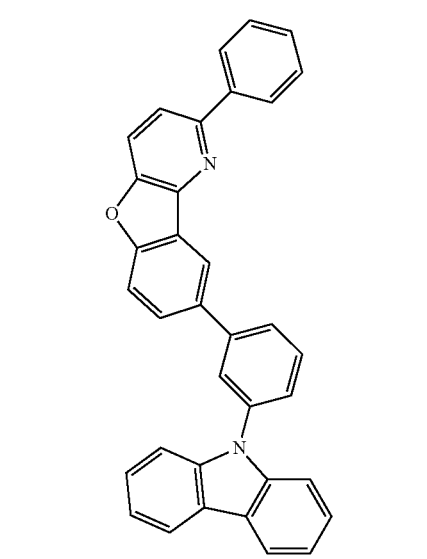
(143)
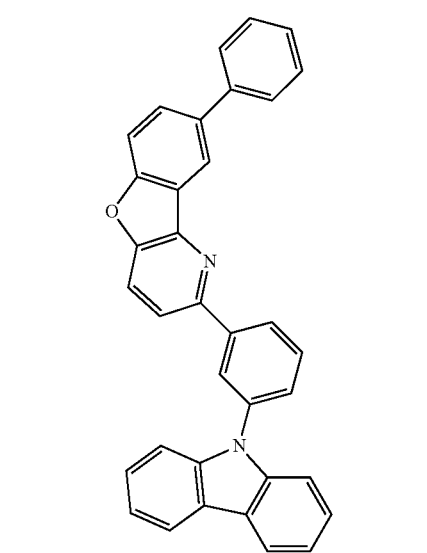

(144)
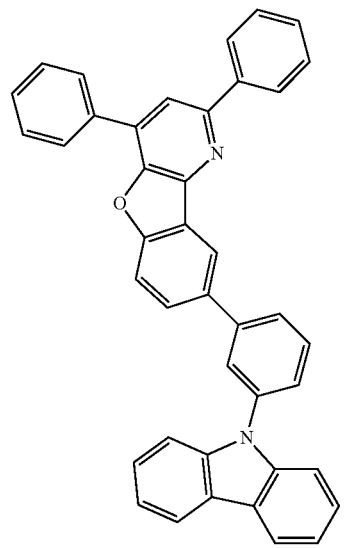
(145)
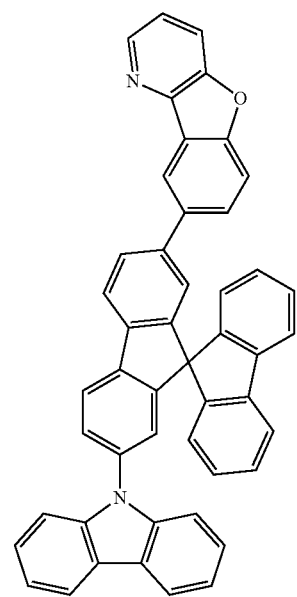
(146)
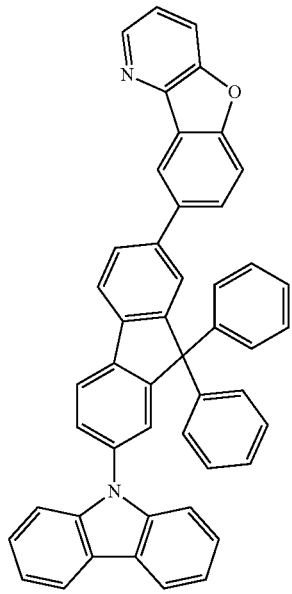
(147)

(148)
(149)
(150)
(151)
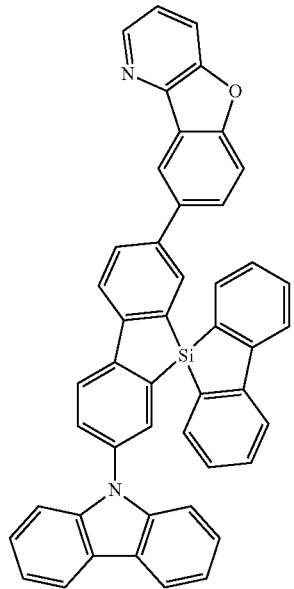
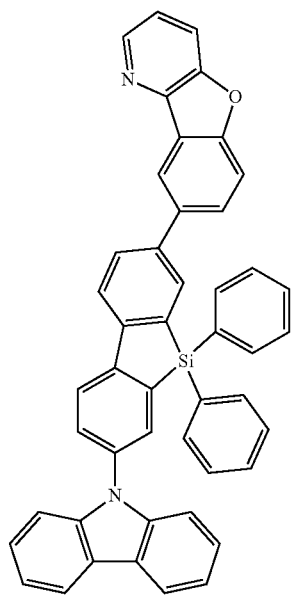
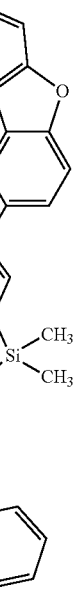
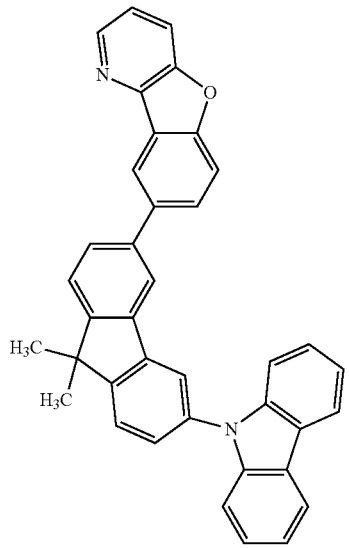

(152)
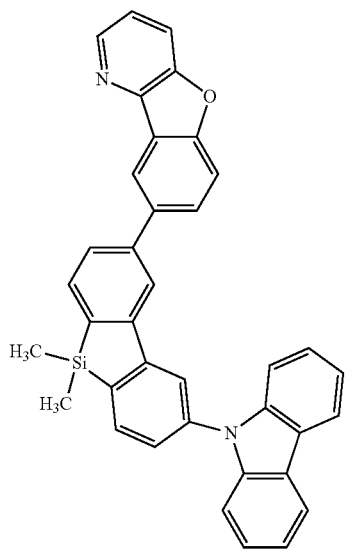
(153)
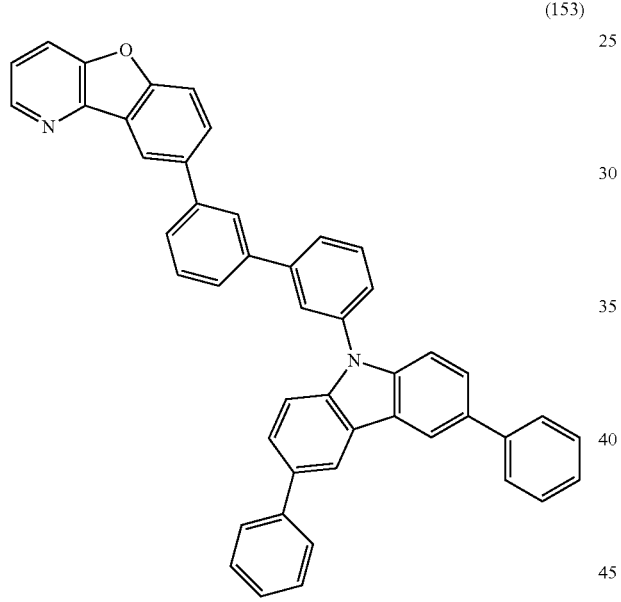
(154)
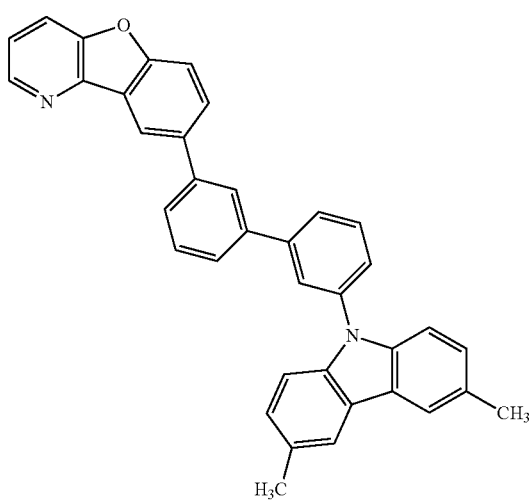
(155)
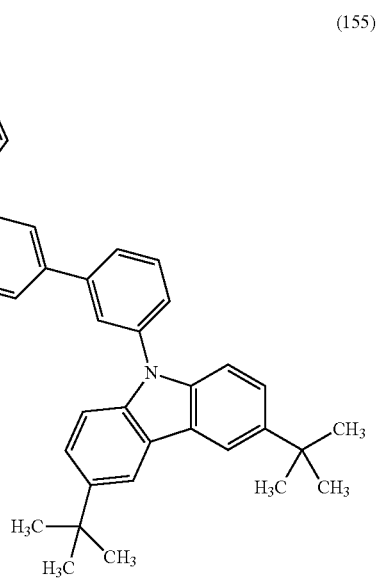
(156)
(157)
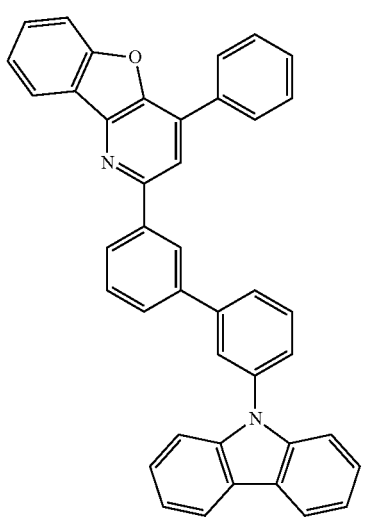

(158) 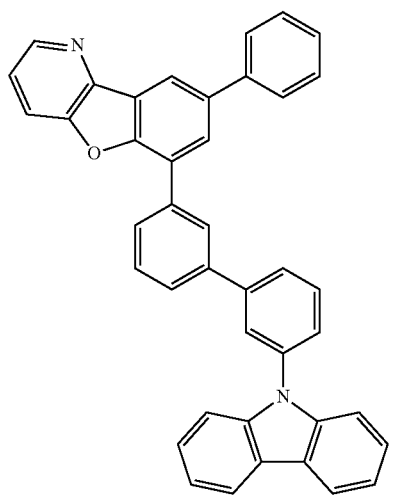
(159) 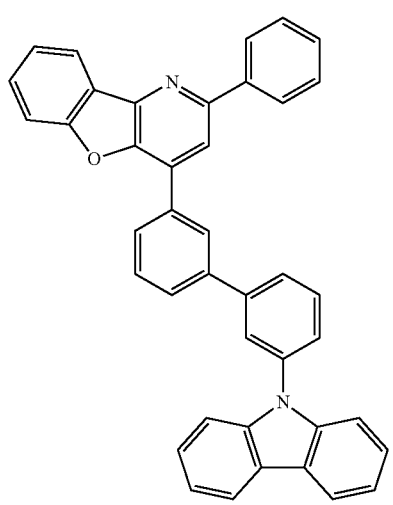
(160) 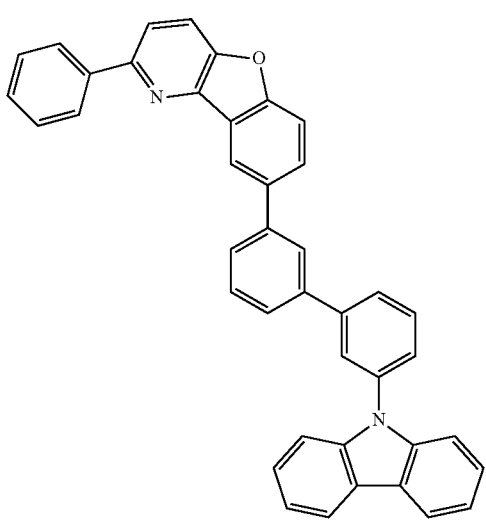
(161) 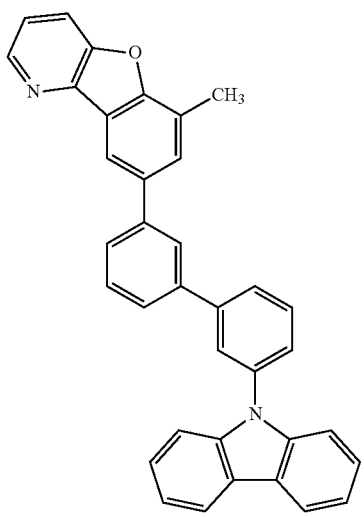
(162) 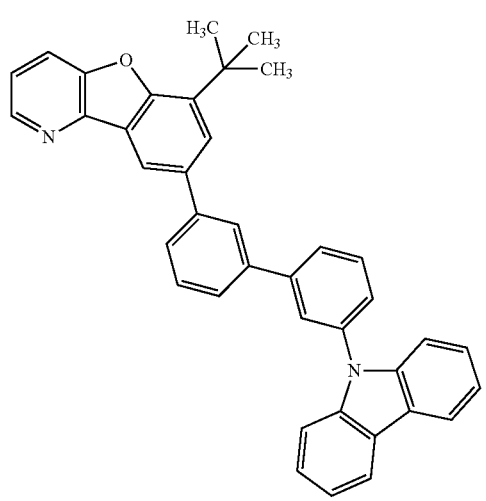
(163) 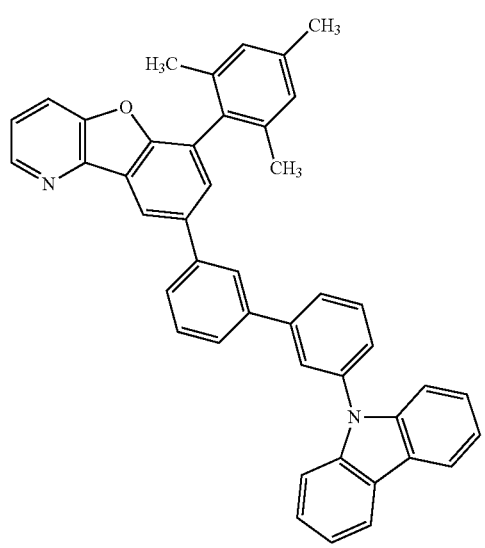

-continued
(164)
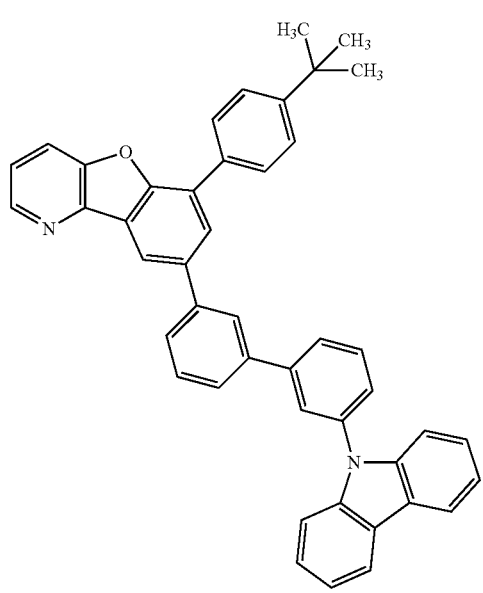
(165)
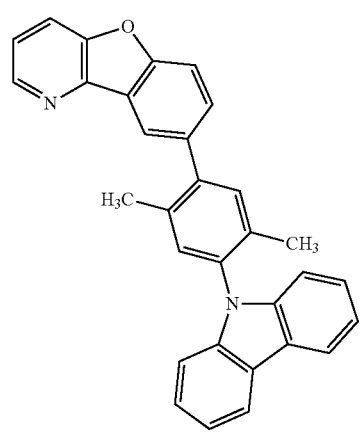
(166)
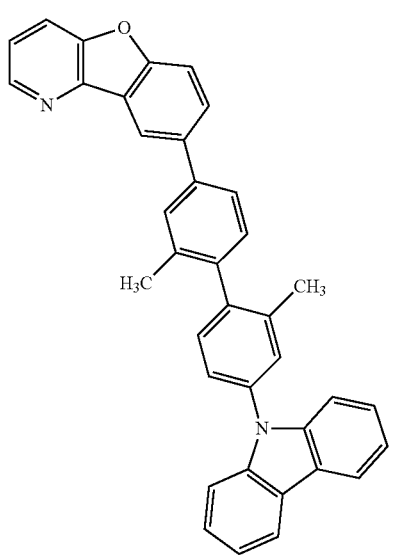
-continued
(167)
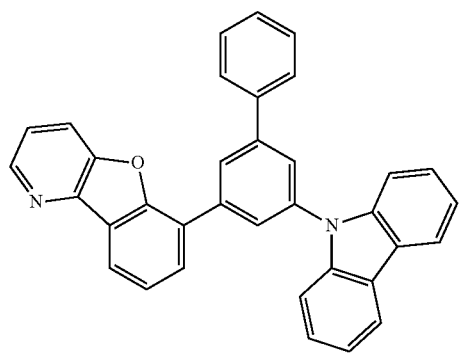
(168)
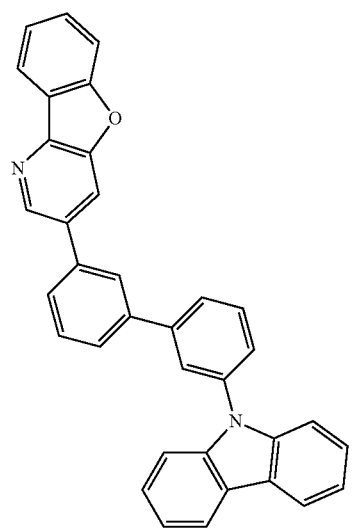
(169)
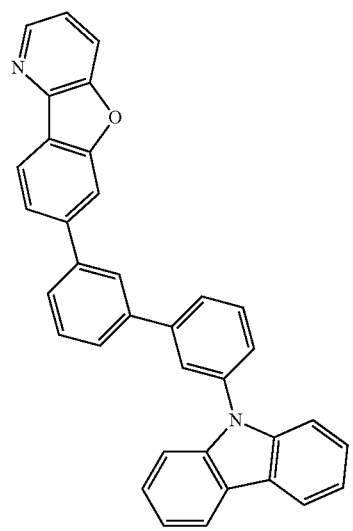

(170)
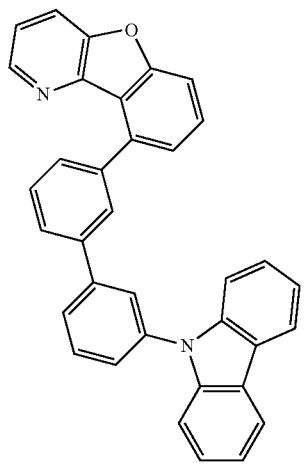
(171)
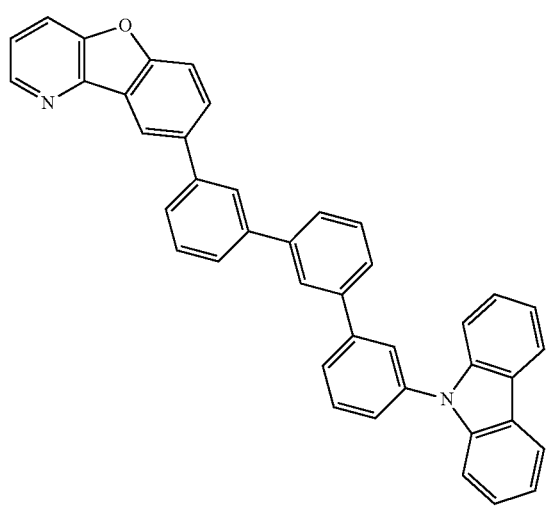
(172)
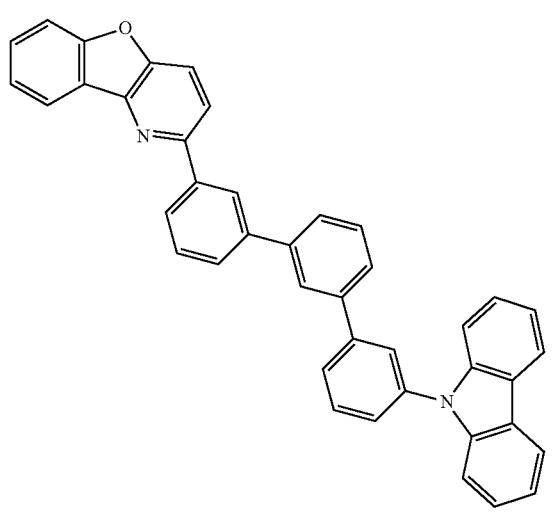
(173)
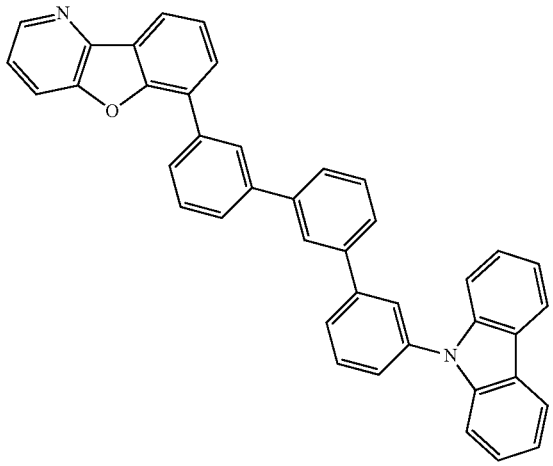
(174)
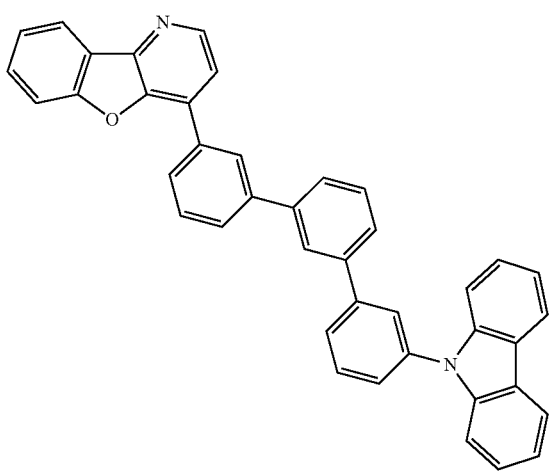
(175)
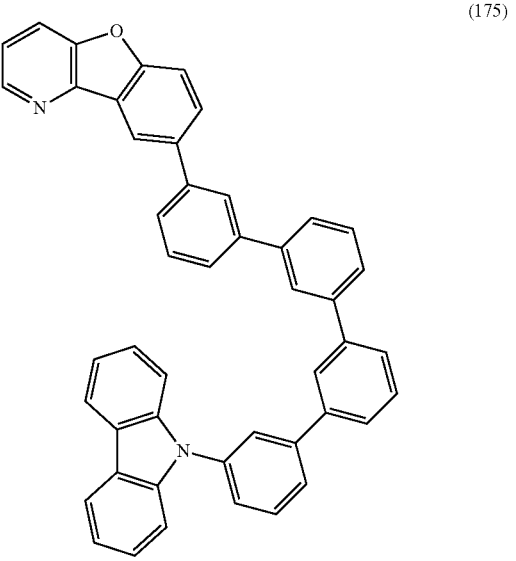

(176)
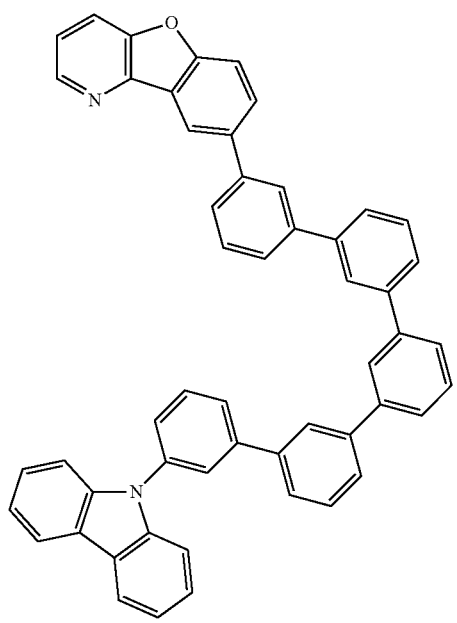
(200)
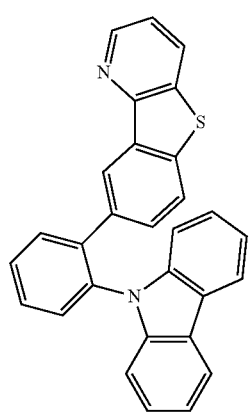
(201)
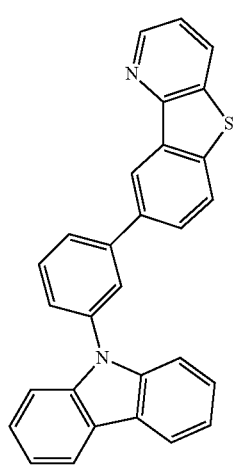
(202)
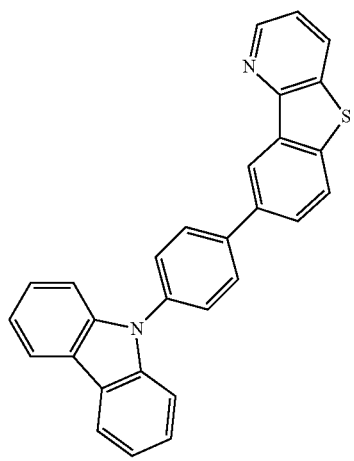
(203)
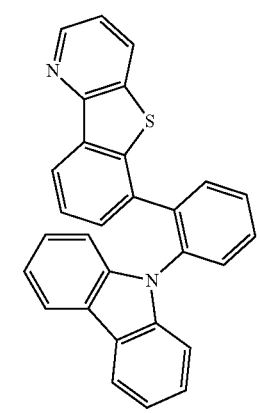
(204)
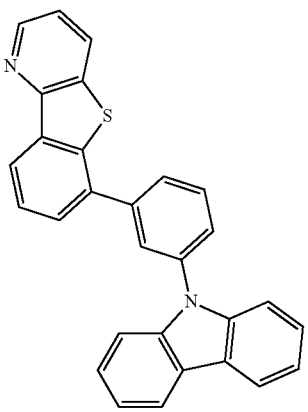
(205)
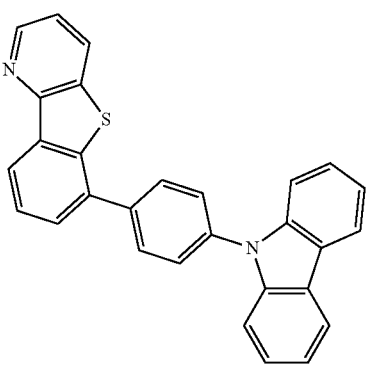

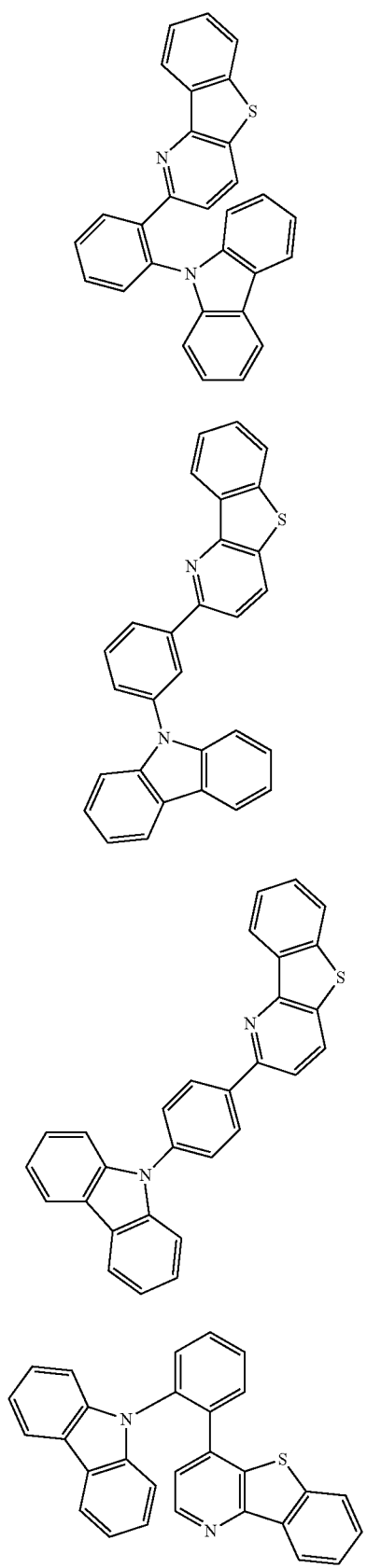
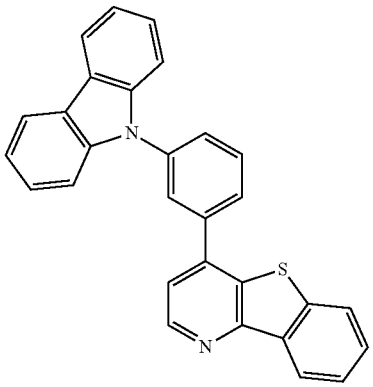

-continued
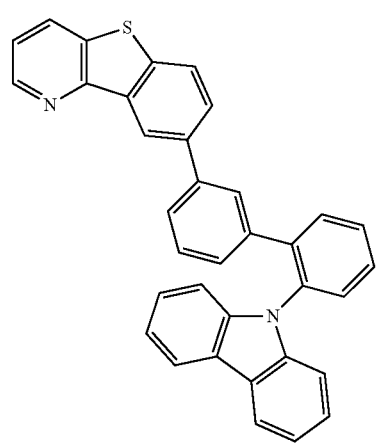
(213)
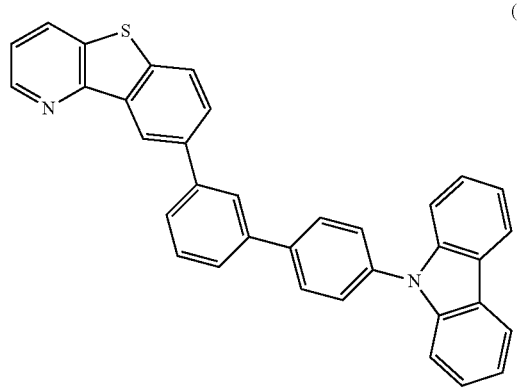
(214)
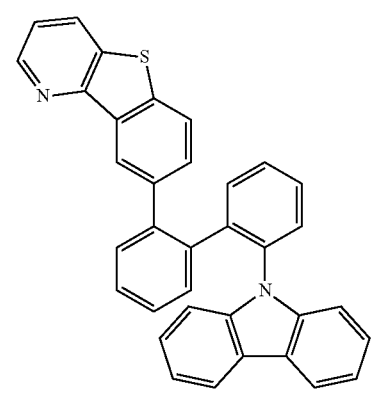
(215)
-continued
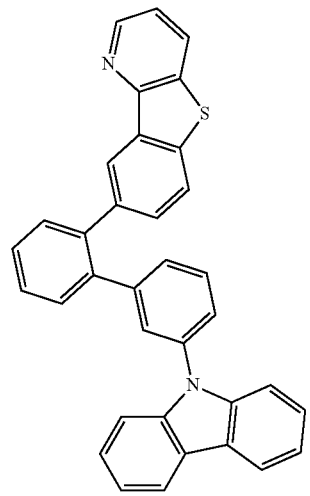
(216)
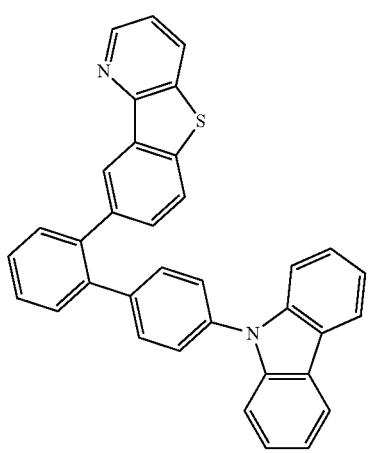
(217)
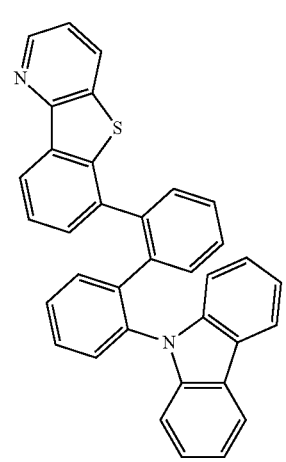
(218)

(219) 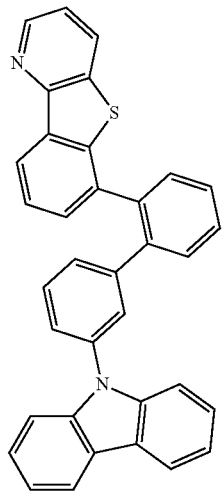
(220) 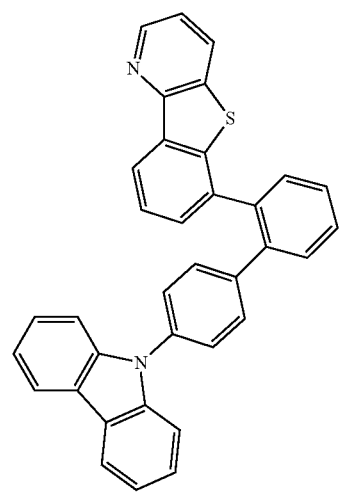
(221) 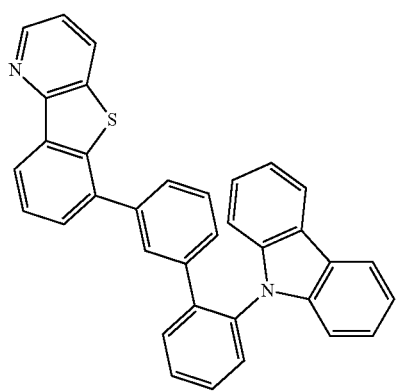
(222) 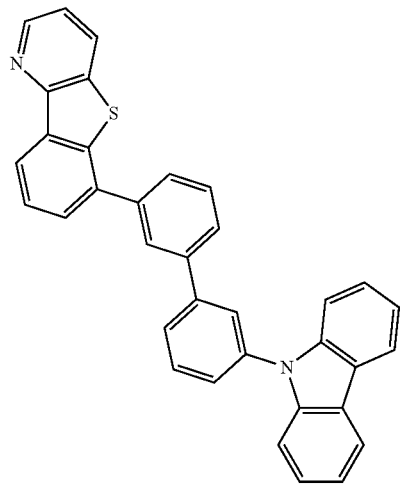
(223) 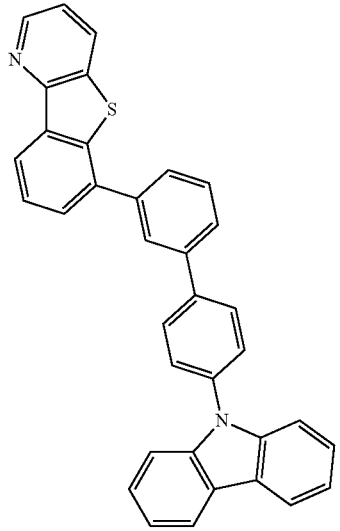
(224) 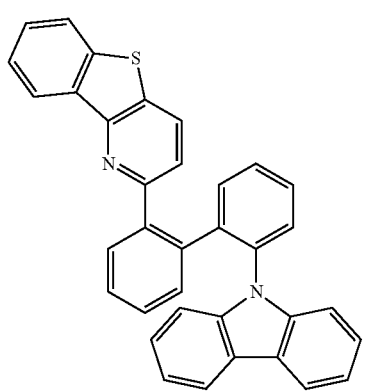

(225) 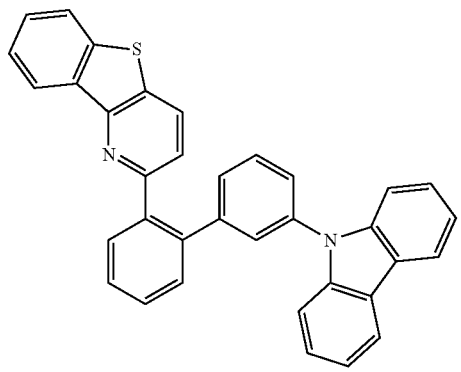
(226) 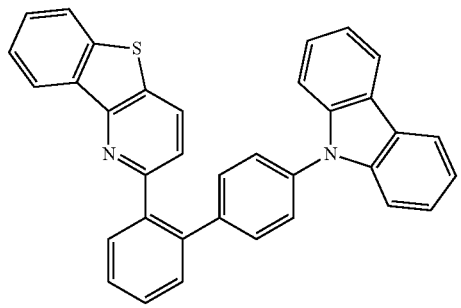
(227) 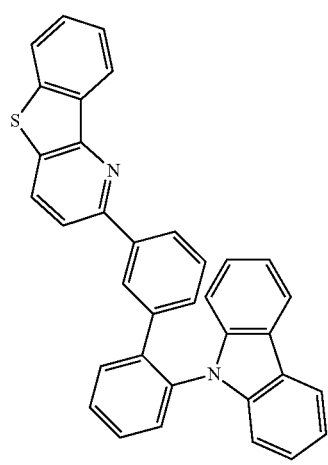
(228) 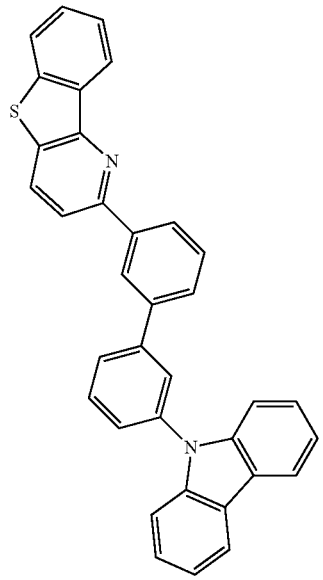
(229) 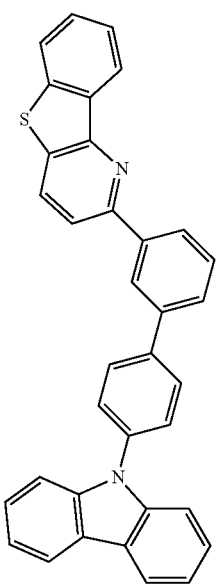
(230) 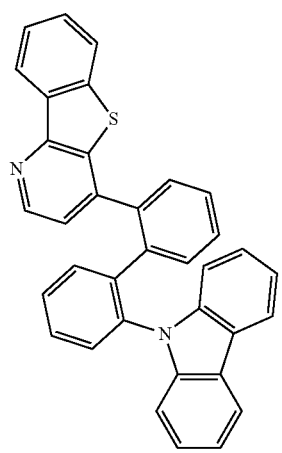

(231) 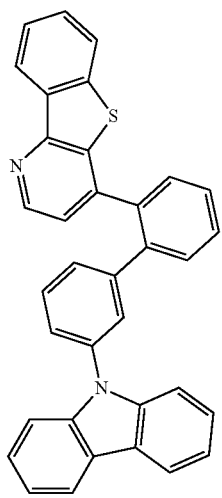
(232) 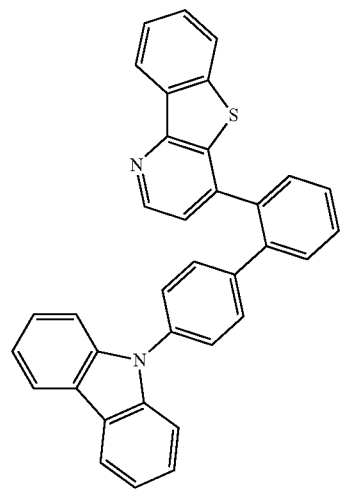
(233) 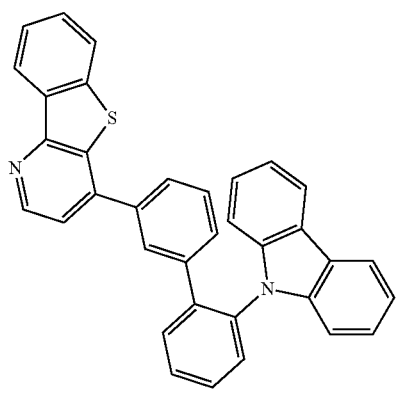
(234) 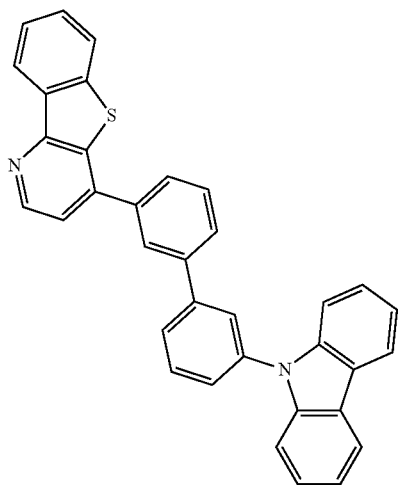
(235) 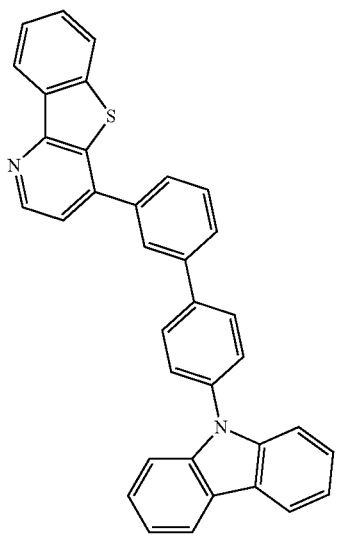
(236) 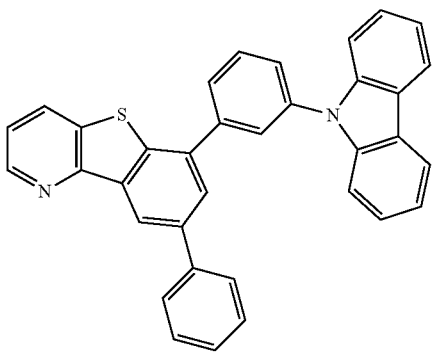

(237)
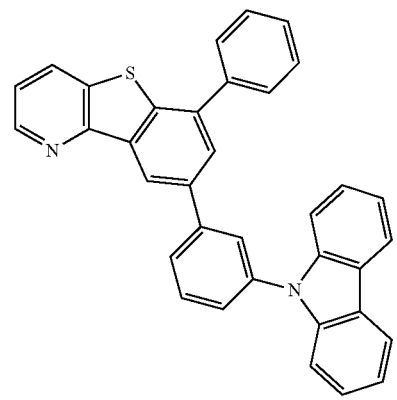
(238)
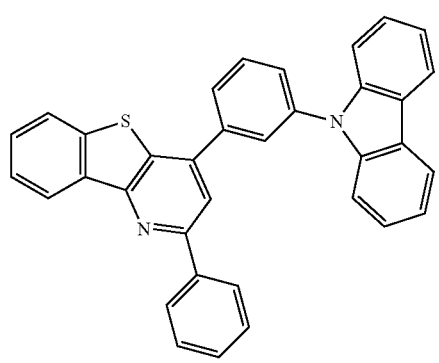
(239)
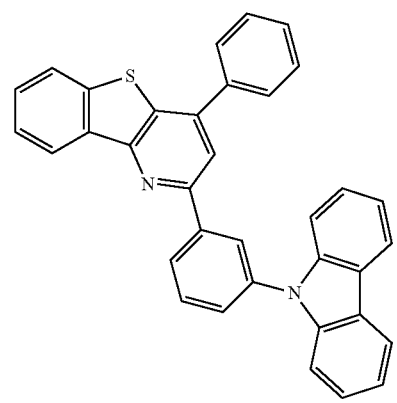
(240)
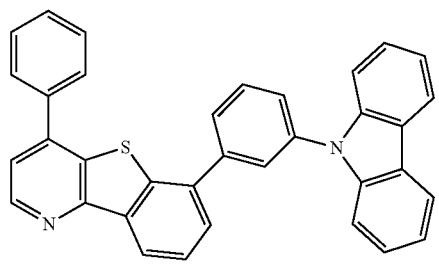
(241)
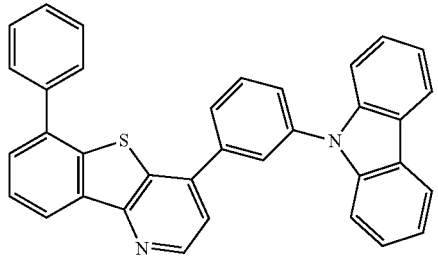
(242)
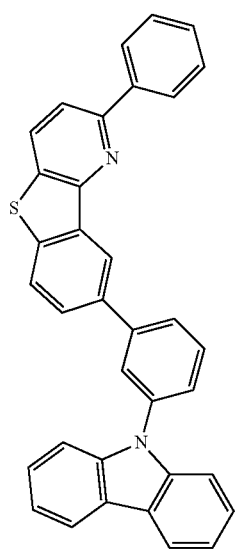
(243)
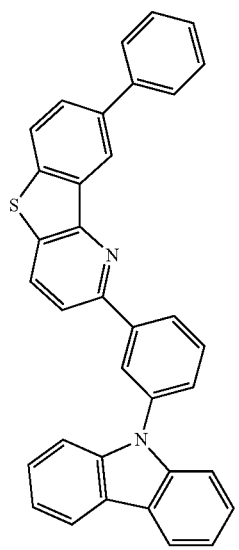

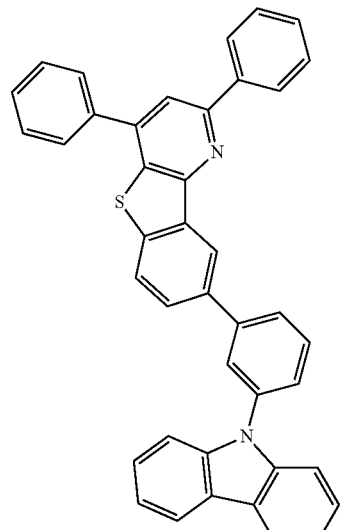
(244)
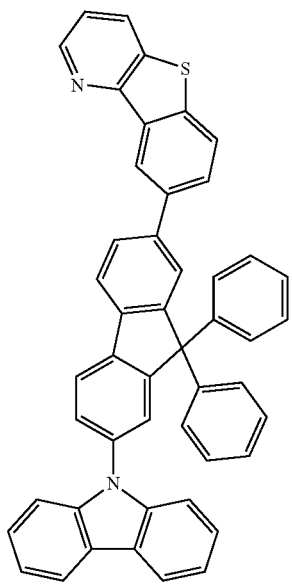
(246)
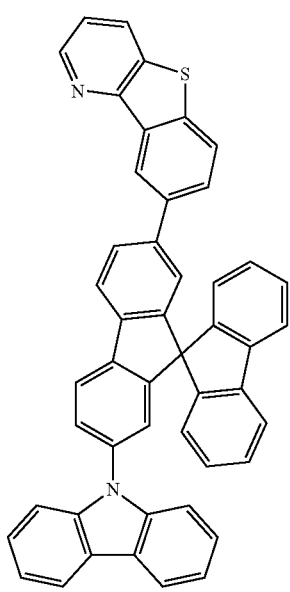
(245)
(247)

(248)
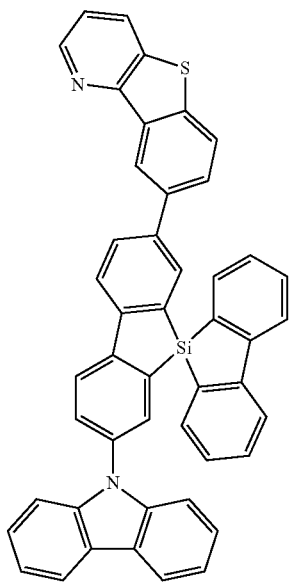
(249)
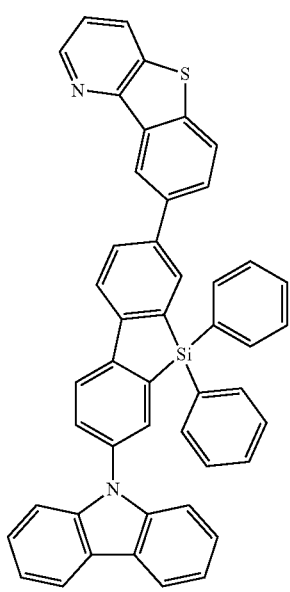
(250)
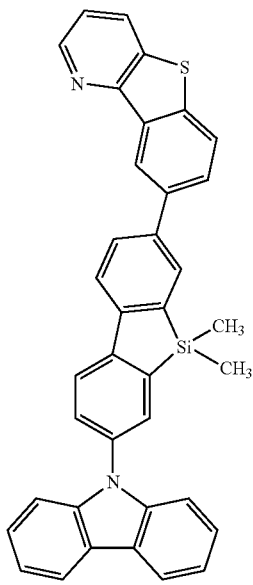
(251)
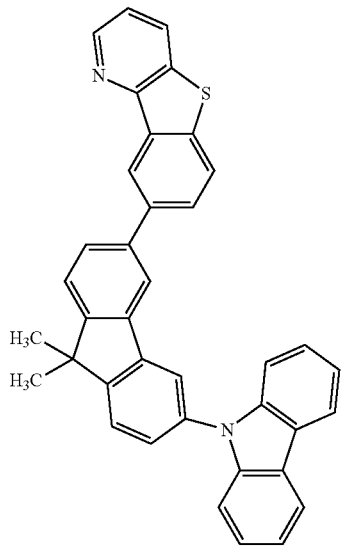

(252)
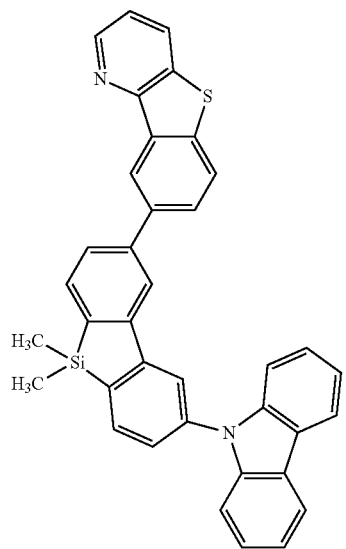
(253)
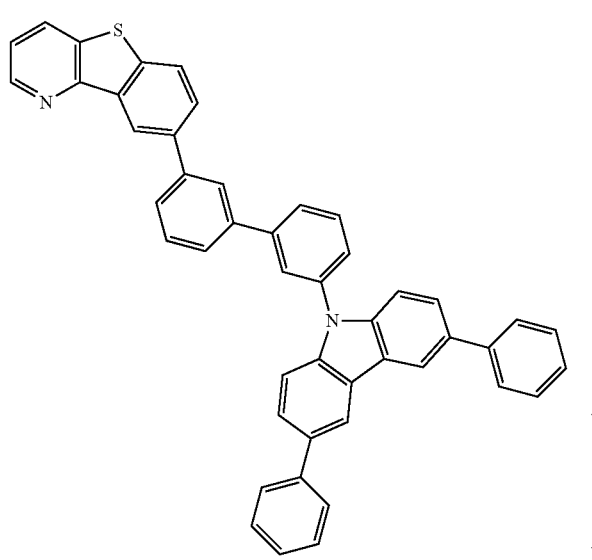
(254)
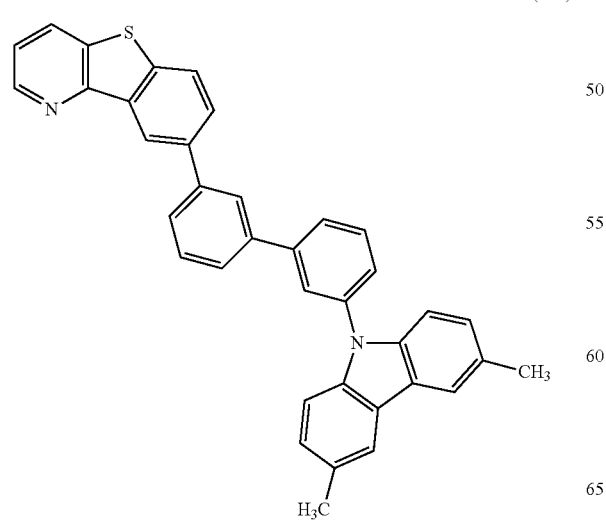
(255)
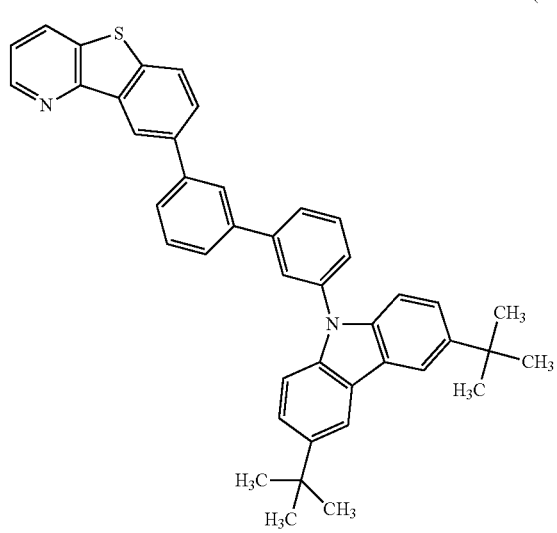
(256)
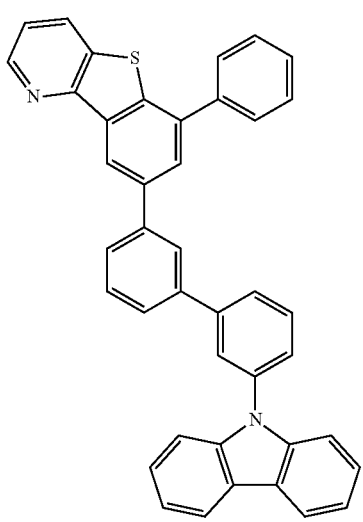
(257)
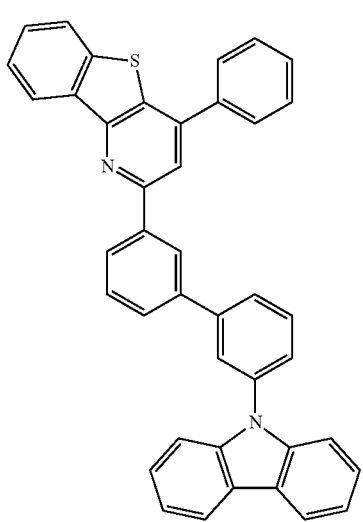

(258)
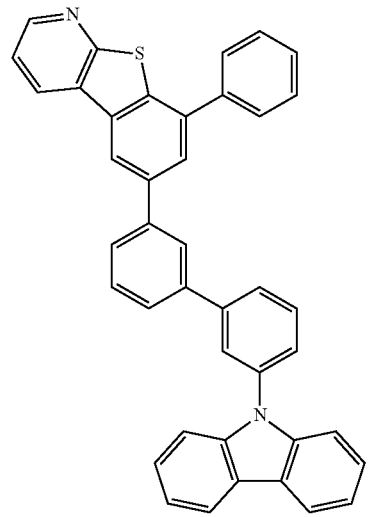
(259)
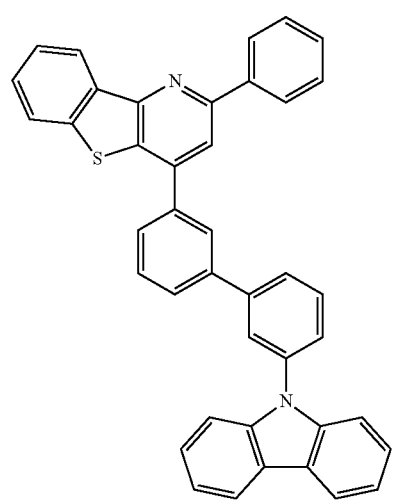
(260)
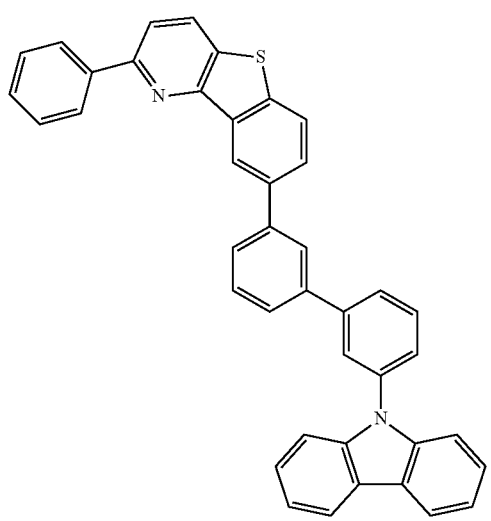
(261)
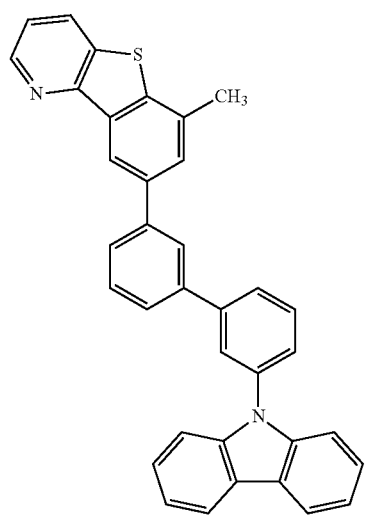
(262)
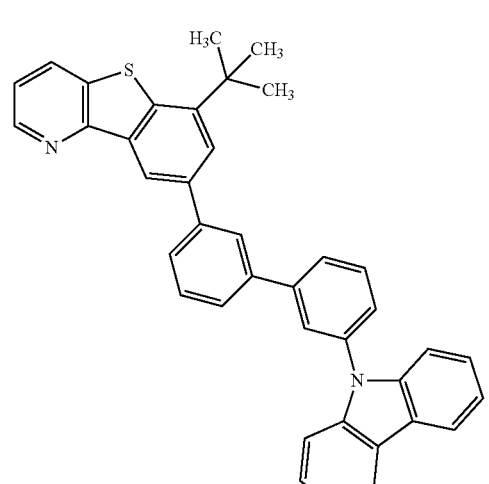
(263)
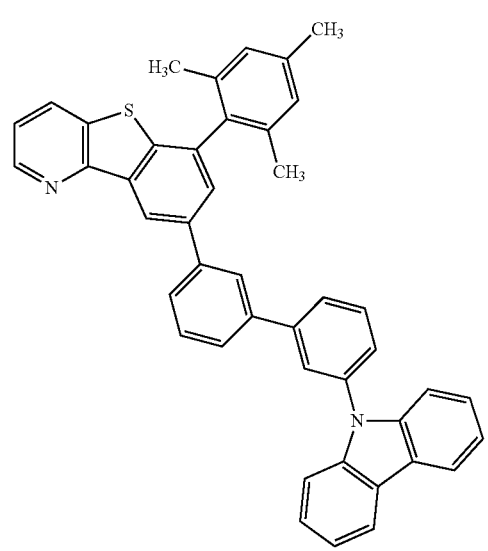

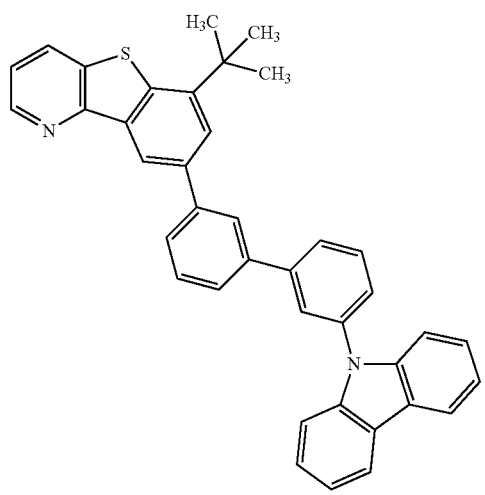
(264)
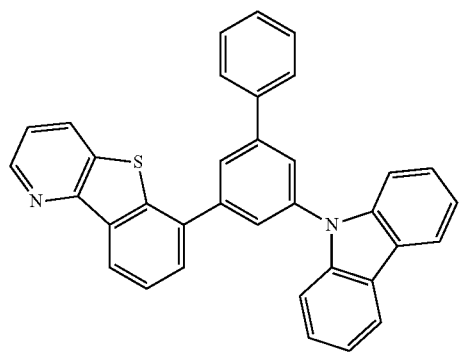
(267)
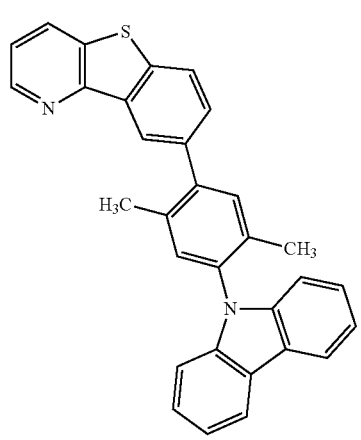
(265)
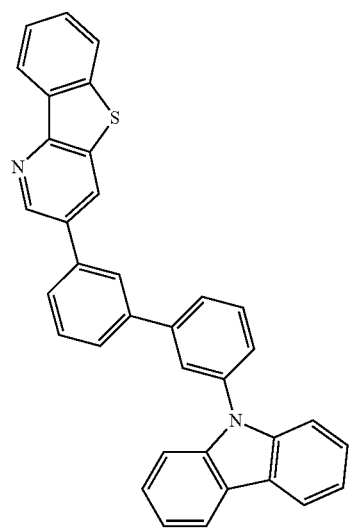
(268)
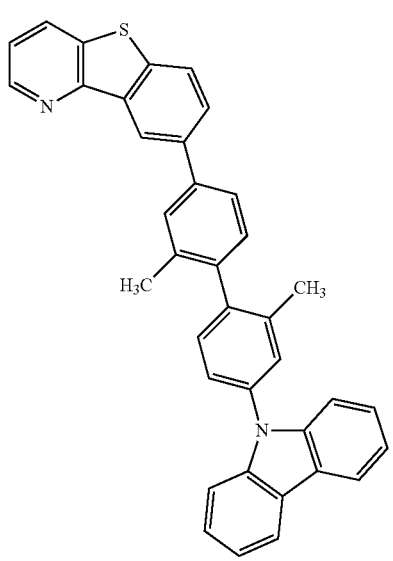
(266)
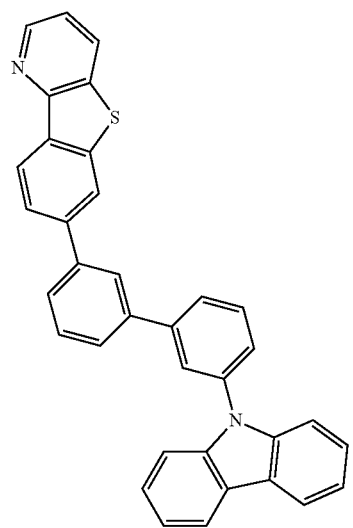
(269)

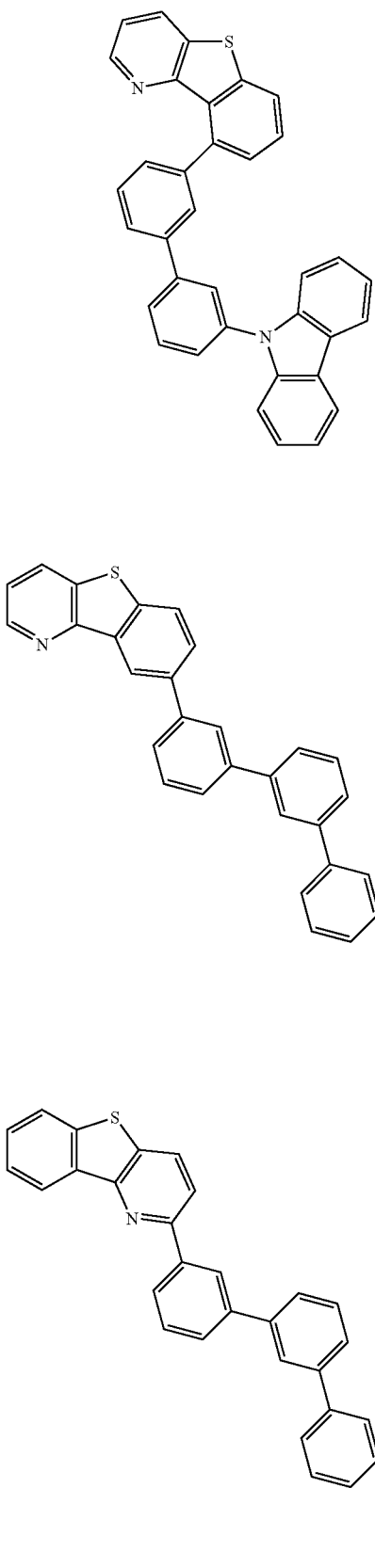
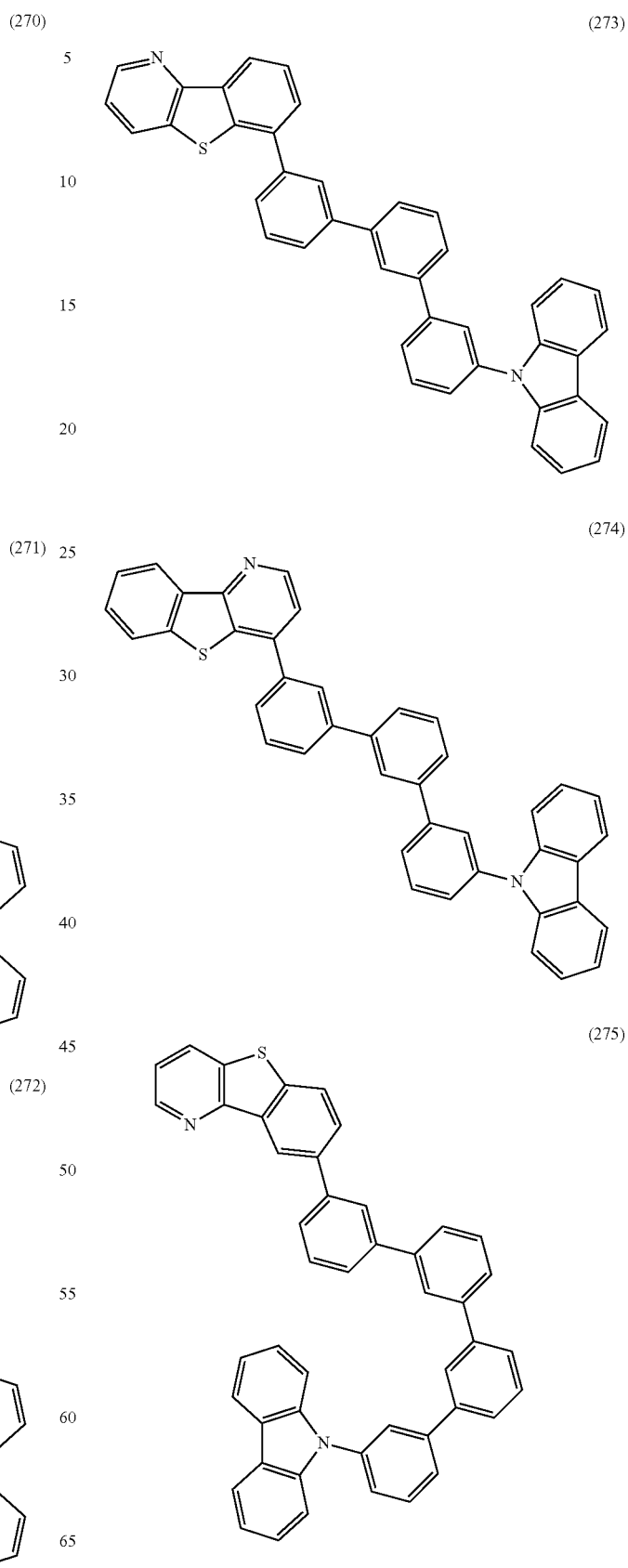

(276)

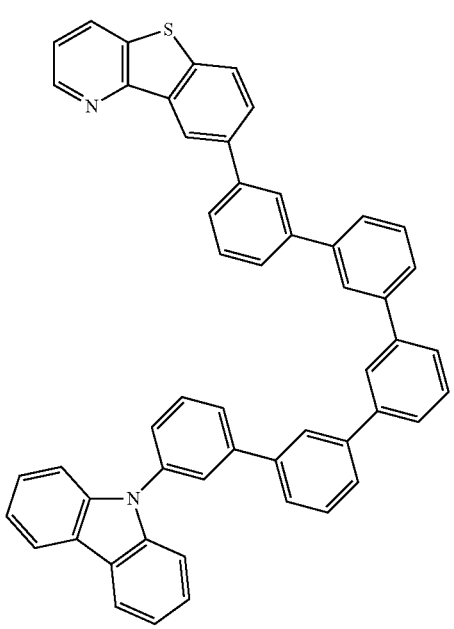

The above-described compounds each have an excellent carrier-transport property and thus are suitable for a carrier-transport material or a host material. Owing to this, a light-emitting element with low driving voltage can also be provided. In addition, the compound can have a high triplet excitation level (T1 level), which makes it possible to provide a phosphorescent light-emitting element with high emission efficiency. Specifically, the compound can provide high emission efficiency even to a phosphorescent light-emitting element that has an emission peak on a shorter wavelength side than green. Moreover, the high triplet excitation level (T1 level) also means the compound having a wide band gap, which allows a blue-emissive fluorescent light-emitting element to efficiently emit light.

Next, a method for synthesizing the compound represented by General Formula (G1) is described.

The compound represented by General Formula (G1) can be synthesized through a simple synthesis scheme as follows. For example, as shown in Synthesis Scheme (A-1), a halide of a benzofuropyridine compound or a halide a benzothienopyridine compound (Structural Formula (A1)) and an organoboron compound or a boron acid of a 9H-carbazole compound (Structural Formula (A2)) are coupled by the Suzuki-Miyaura reaction, whereby the compound represented by General Formula (G1) can be obtained.

Scheme (A-1)

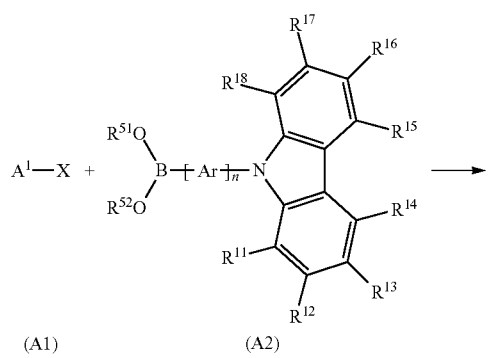

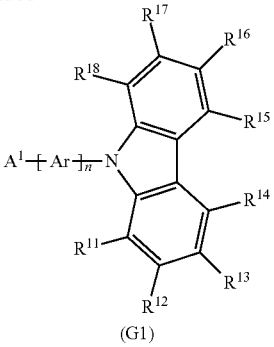

In Synthesis Scheme (A-1), each of $R^{11}$ to $R^{18}$ independently represents hydrogen, a substituted or unsubstituted alkyl group having 1 to 6 carbon atoms, or a substituted or unsubstituted aryl group having 6 to 13 carbon atoms; Ar represents a substituted or unsubstituted arylene group having 6 to 13 carbon atoms; n represents a natural number of 1 to 5; and each of $R^{51}$ and $R^{52}$ independently represents hydrogen or an alkyl group having 1 to 6 carbon atoms. In Synthesis Scheme (A-1), $R^{51}$ and $R^{52}$ may be bonded to each other to form a ring. In addition, X represents a halogen, a trifluoromethanesulfonic acid ester (another name: triflate) group, a mesylate group, or a monochlate group. Among them, iodine, bromine, or a triflate group is preferred.

Examples of a palladium catalyst that can be used in Synthesis Scheme (A-1) include, but are not limited to, palladium(II) acetate, tetrakis(triphenylphosphine)palladium(0), and bis(triphenylphosphine)palladium(II) dichloride. Examples of a ligand of the palladium catalyst that can be used in Synthesis Scheme (A-1) include, but are not limited to, tri(ortho-tolyl)phosphine, triphenylphosphine, and tricyclohexylphosphine.

Examples of a base that can be used in Synthesis Scheme (A-1) include, but not limited to, an organic base such as sodium tert-butoxide and an inorganic base such as potassium carbonate or sodium carbonate.

Examples of the solvent that can be used in Synthesis Scheme (A-1) include, but are not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and the like. In particular, a mixed solvent of toluene and water, a mixed solvent of toluene, ethanol, and water, or a mixed solvent of water and an ether such as ethylene glycol dimethyl ether is preferred.

The Suzuki-Miyaura reaction shown in Synthesis Scheme (A-1) may be replaced with a cross coupling reaction using an organoaluminum compound, an organozirconium compound, an organozinc compound, an organotin compound, or the like as well as the organoboron compound or boronic acid represented by Structural Formula (A2). However, the present invention is not limited thereto.

In the Suzuki-Miyaura reaction shown in Synthesis Scheme (A-1), an organoboron compound of the benzofuropyridine compound, a boronic acid of the benzofuropyridine compound, an organoboron compound of the benzothienopyridine compound, or a boronic acid of the benzothienopyridine compound may be coupled with the 9H-carbazole compound that has a halide or a triflate group as a substituent, by the Suzuki-Miyaura reaction.

Various kinds of the compounds represented by Structural Formulae (A1) and (A2) are commercially available or can be obtained by synthesis, which means that a great variety of the compounds represented by General Formula (G1) can be synthesized. Thus, a feature of the compound of one embodiment of the present invention is the abundance of variations.

The compound represented by Structural Formula (A1) may be a compound represented by General Formula (G5).

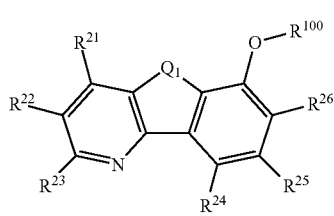

(G5)

In General Formula (G5), each of $R^{21}$ to $R^{26}$ independently represents hydrogen, a substituted or unsubstituted alkyl group having 1 to 6 carbon atoms, or a substituted or unsubstituted aryl group having 6 to 13 carbon atoms; $Q^1$ represents an oxygen atom or a sulfur atom; and $R^{100}$ represents a triflate group, a mesylate group, or a monochlate group, and preferably represents a triflate group.

The compound represented by General Formula (G5) is useful in synthesizing a compound of one embodiment of the present invention represented by General Formula (G1).

For example, compounds (400) to (405) can be used as the compound represented by General Formula (G5).

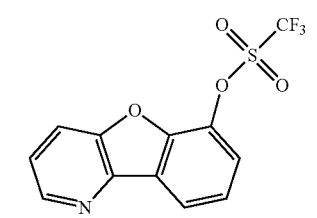

(400)

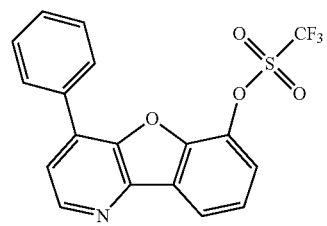

(401)

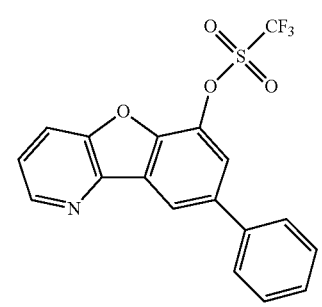

(402)

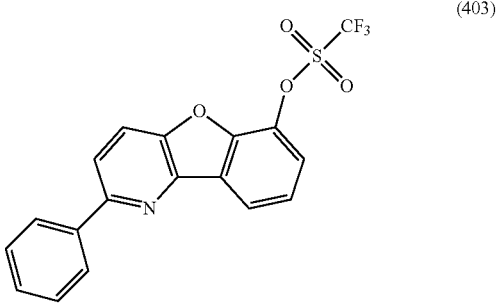

(403)

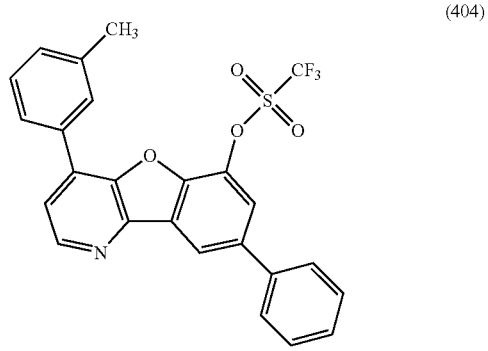

(404)

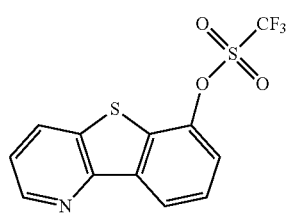

(405)

The compound represented by General Formula (G5) can be synthesized through a simple synthesis scheme as follows. As shown in Scheme (A-2), for example, an alkylether compound of a benzofuropyridine compound or an alkylether compound of a benzothienopyridine compound (General Formula (G6)) can become an alcohol compound of the benzofuropyridine compound or an alcohol compound of the benzothienopyridine compound (General Formula (G7)). From this compound, an ester compound of the benzofuropyridine compound or an ester compound of the benzothienopyridine compound (General Formula (G5)) can be synthesized as shown in Scheme (A-3).

Scheme (A-2)

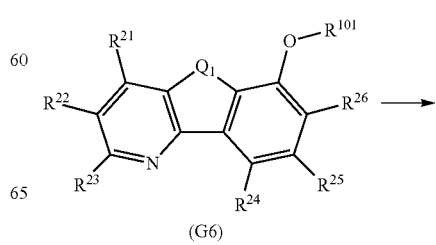

(G6)

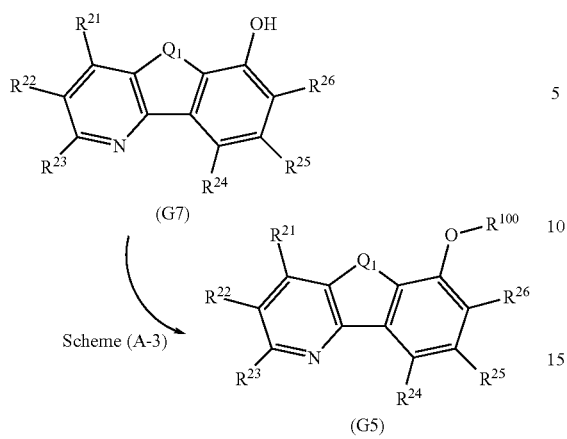

In General Formulae (G5), (G6), and (G7), each of $R^{21}$ to $R^{26}$ independently represents hydrogen, a substituted or unsubstituted alkyl group having 1 to 6 carbon atoms, or a substituted or unsubstituted aryl group having 6 to 13 carbon atoms; $Q^1$ represents an oxygen atom or a sulfur atom; $R^{100}$ represents a triflate group, a mesylate group, or a monochlate group, and preferably represents a triflate group; and $R^{101}$ represents a substituted or unsubstituted alkyl group having 1 to 6 carbon atoms.

In Scheme (A-2), dealkylation reaction can be used. Specifically, the alkylether compound of the benzofuropyridine compound or the alkylether compound of the benzothienopyridine compound (General Formula (G6)) is reacted with boron tribromide in a halogen-based solvent such as dichloromethane or chloroform at low temperature.

In Scheme (A-3), a nucleophilic substitution reaction can be used. Specifically, the alcohol compound of the benzofuropyridine compound or the alcohol compound of the benzothienopyridine compound (General Formula (G7)) is reacted with trifluoromethanesulfonic anhydride, trifluoromethanesulfonyl chloride, methanesulfonyl chloride, chloromethylsulfonyl chloride, or the like in a halogen-based solvent such as dichloromethane or chloroform at low temperature in the presence of a base such as pyridine.

For example, compounds (410) to (415) can be used as the compound represented by General Formula (G6).

(410)
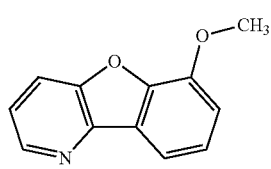

(411)
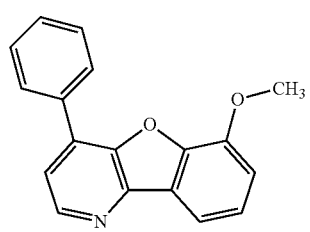

(412)
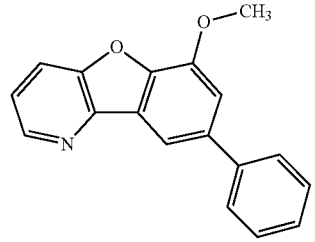

(413)
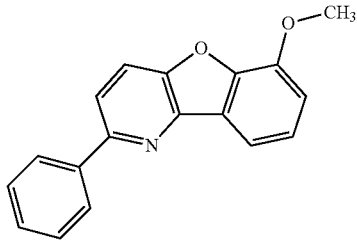

(414)
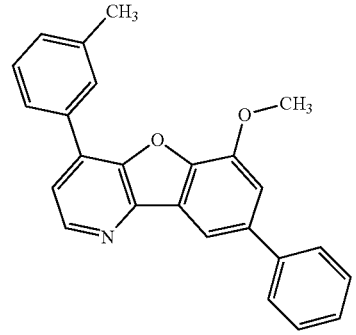

(415)
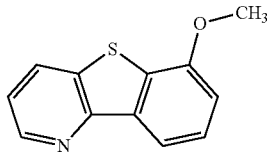

For example, compounds (420) to (425) can be used as the compound represented by General Formula (G7).

(420)
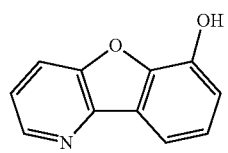

(421)
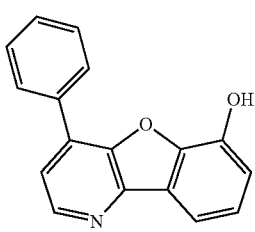

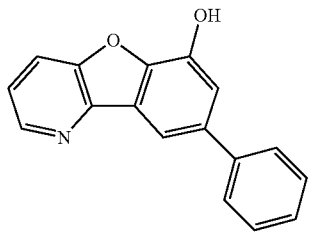
(422)

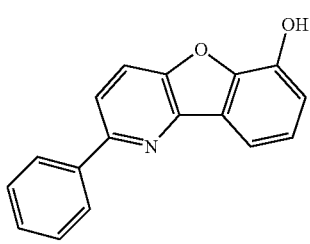
(423)

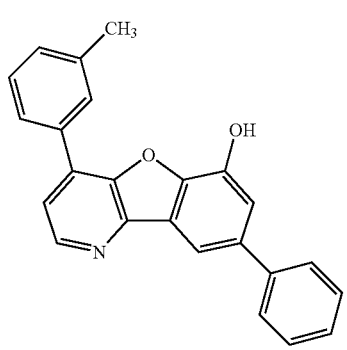
(424)

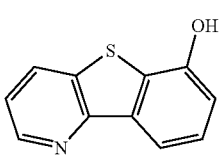
(425)

The compound represented by General Formula (G6) can be synthesized through a simple synthesis scheme as follows. As shown in Scheme (A-4), for example, a pyridine compound (General Formula (A3)) is cross-coupled with a phenyl ether compound (General Formula (A4)) to give the compound represented by General Formula (G6).

Scheme (A-4)

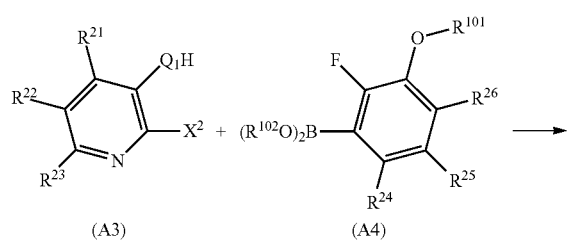

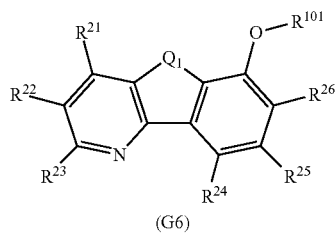
(G6)

In General Formula (G6), each of $R^{21}$ to $R^{26}$ independently represents hydrogen, a substituted or unsubstituted alkyl group having 1 to 6 carbon atoms, or a substituted or unsubstituted aryl group having 6 to 13 carbon atoms; $Q^1$ represents an oxygen atom; $R^{101}$ represents a substituted or unsubstituted alkyl group having 1 to 6 carbon atoms; $R^{102}$ represents an alkyl group having 1 to 6 carbon atoms; and $X^2$ represents a halogen, iodine, bromine, or chlorine.

In Scheme (A-4), a cross coupling reaction can be used. Specifically, in the presence of a base such as potassium carbonate, the pyridine compound (General Formula (A3)) and the phenyl ether compound (General Formula (A4)) are reacted by adding a palladium catalyst such as tetrakis(triphenylphosphine)palladium(0) or the like and heating, whereby the compound represented by General Formula (G1) can be obtained.

The compound represented by Structural Formula (A1) may be a compound represented by General Formula (G8).

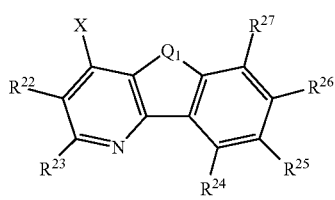
(G8)

In General Formula (G8), each of $R^{22}$ to $R^{27}$ independently represents hydrogen, a substituted or unsubstituted alkyl group having 1 to 6 carbon atoms, or a substituted or unsubstituted aryl group having 6 to 13 carbon atoms; $Q^1$ represents an oxygen atom or a sulfur atom; and X represents a halogen, a triflate group, a mesylate group, or a monochlate group, and preferably represents iodine or bromine.

The compound represented by General Formula (G8) is useful in synthesizing a compound of one embodiment of the present invention represented by General Formula (G1).

For example, compounds (430) to (437) can be used as the compound represented by General Formula (G8).

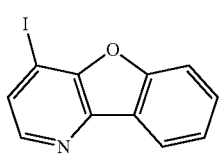
(430)

(431)

(432)

(433)

(434)

(435)

(436)

(437)

The compound represented by General Formula (G8) can be synthesized through a simple synthesis scheme as follows. As shown in Scheme (A-5), for example, a halide of a benzofuropyridine compound or a halide of a benzothienopyridine compound (General Formula (G8)) can be synthesized from a benzofuropyridine compound or a benzothienopyridine compound (General Formula (A5)).

Scheme (A-5)

(A5)

(G8)

In General Formula (G8), each of $R^{22}$ to $R^{27}$ independently represents hydrogen, a substituted or unsubstituted alkyl group having 1 to 6 carbon atoms, or a substituted or unsubstituted aryl group having 6 to 13 carbon atoms; $Q^1$ represents an oxygen atom or a sulfur atom; and X represents a halogen, and preferably represents iodine or bromine.

In Scheme A-5, a substitution reaction can be used. Specifically, synthesis can be performed in such a manner that in the presence of a base such as lithium diisopropylamide (abbreviation: LDA), a halogen such as iodine, bromine, or chlorine is added in a solvent such as THF at low temperature, and then the temperature is returned to room temperature.

The above is the description of the example of a method for synthesizing the compound of one embodiment of the present invention; however, the present invention is not limited thereto and any other synthesis method may be employed.

Embodiment 2

In this embodiment, one mode of a light-emitting element including a compound having a structure in which a carbazole skeleton is bonded to a benzofuropyridyl group or a benzothienopyridyl group through an arylene group is described below with reference to FIG. 1A.

A light-emitting element of this embodiment includes a plurality of layers between a pair of electrodes. In this embodiment, the light-emitting element includes a first electrode 101, a second electrode 102, and an EL layer 103 provided between the first electrode 101 and the second electrode 102. Note that in FIG. 1A, the first electrode 101 functions as an anode and the second electrode 102 functions as a cathode. That is, when voltage is applied between the first electrode 101 and the second electrode 102 such that the potential of the first electrode 101 is higher than that of the second electrode 102, light emission can be obtained. Of course, a structure in which the first electrode functions as a cathode and the second electrode functions as an anode can be employed. In that case, the stacking order of layers in the EL layer is reversed from the stacking order described below. Note that in the light-emitting element of this embodiment, at least one of layers in the EL layer 103 contains the compound having a structure in which a carbazole skeleton is bonded to a benzofuropyridyl group or a benzothienopyridyl group through an arylene group. A layer that contains the compound is preferably used as a light-emitting layer or an electron-transport layer because the characteristics of the compound can be utilized and the light-emitting element can have favorable characteristics.

For the electrode functioning as an anode, any of metals, alloys, electrically conductive compounds, and mixtures thereof which have a high work function (specifically, a work function of 4.0 eV or more) or the like is preferably used. Specific examples are indium tin oxide (ITO), indium tin oxide containing silicon or silicon oxide, indium oxide-zinc oxide, indium oxide containing tungsten oxide and zinc oxide (IWZO), and the like. Films of these electrically conductive metal oxides are usually formed by a sputtering method but may be formed by a sol-gel method or the like. For example, indium oxide-zinc oxide can be formed by a sputtering method using a target in which zinc oxide is added to indium oxide at higher than or equal to 1 wt % and lower than or equal to 20 wt %. Moreover, indium oxide containing tungsten oxide and zinc oxide (IWZO) can be formed by a sputtering method using a target in which tungsten oxide is added to indium oxide at higher than or equal to 0.5 wt % and lower than or equal to 5 wt % and zinc oxide is added to indium oxide at higher than or equal to 0.1 wt % and lower than or equal to 1 wt %. Other examples are gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), and the like. Graphene may also be used.

There is no particular limitation on the stacked structure of the EL layer 103. The EL layer 103 can be formed by combining a layer containing a substance having a high electron-transport property, a layer containing a substance having a high hole-transport property, a layer containing a substance having a high electron-injection property, a layer containing a substance having a high hole-injection property, a layer containing a bipolar substance (a substance having a high electron-transport and hole-transport property), a layer having a carrier-blocking property, and the like as appropriate. In this embodiment, the EL layer 103 has a structure in which a hole-injection layer 111, a hole-transport layer 112, a light-emitting layer 113, an electron-transport layer 114, and an electron-injection layer 115 are stacked in this order over the electrode functioning as an anode. Materials contained in the layers are specifically given below.

The hole-injection layer 111 is a layer containing a substance having a hole-injection property. As the substance having a high hole-injection property, for example, a molybdenum oxide, a vanadium oxide, a ruthenium oxide, a tungsten oxide, or a manganese oxide can be used. The hole-injection layer 111 can also be formed using a phthalocyanine-based compound such as phthalocyanine (abbreviation: $H_2Pc$) or copper phthalocyanine (abbreviation: CuPc); an aromatic amine compound such as 4,4'-bis[N-(4-diphenylaminophenyl)-N-phenylamino]biphenyl (abbreviation: DPAB) or N,N'-bis {4-[bis(3-methylphenyl)amino]phenyl}-N,N'-diphenyl-(1,1'-biphenyl)-4,4'-diamine (abbreviation: DNTPD); a high molecule compound such as poly(ethylenedioxythiophene)/poly(styrenesulfonic acid) (PEDOT/PSS), or the like.

The hole-injection layer 111 can be formed using a composite material in which a substance exhibiting an electron-accepting property (hereinafter, simply referred to as "electron-accepting substance") with respect to a substance having a hole-transport property is contained in the substance having a hole-transport property. In this specification, the composite material refers to not a material in which two materials are simply mixed but a material in the state where charge transfer between the materials can be caused by a mixture of a plurality of materials. This charge transfer includes the charge transfer that occurs only when an electric field exists.

Note that by using the composite material in which the electron-accepting substance is contained in the substance having a hole-transport property, a material used for forming the electrode can be selected regardless of the work function of the material. In other words, besides a material having a high work function, a material having a low work function can be used for the electrode functioning as an anode. Examples of the electron-accepting substance are 7,7,8,8-tetracyano-2,3,5,6-tetrafluoroquinodimethane (abbreviation: $F_4$-TCNQ), chloranil, and the like. A transition metal oxide can also be used. In particular, an oxide of a metal belonging to any of Groups 4 to 8 of the periodic table can be suitably used. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable as the electron-accepting substance because it is stable in the air, has a low hygroscopic property, and is easily handled.

As the substance with a hole-transport property used for the composite material, any of a variety of organic compounds such as an aromatic amine compound, a carbazole compound, an aromatic hydrocarbon, and a high molecular compound (such as an oligomer, a dendrimer, or a polymer) can be used. The organic compound used for the composite material is preferably an organic compound having a high hole-transport property. Specifically, a substance having a hole mobility of $1 \times 10^{-6}$ cm$^2$/Vs or higher is preferably used. Note that any other substance may be used as long as the substance has a hole-transport property higher than an electron-transport property. Specific examples of the organic compound that can be used as a substance having a hole-transport property in the composite material are given below.

Examples of the aromatic amine compound are N,N-di (p-tolyl)-N,N-diphenyl-p-phenylenediamine (abbreviation: DTDPPA), 4,4'-bis[N-(4-diphenylaminophenyl)-N-phenylamino]biphenyl (abbreviation: DPAB), N,N'-bis {4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and the like.

Specific examples of the carbazole compound that can be used for the composite material are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Other examples of the carbazole compound that can be used for the composite material are 4,4'-di(N-carbazolyl) biphenyl (abbreviation: CBP), 1,3,5-tris[4-(N-carbazolyl) phenyl]benzene (abbreviation: TCPB), 9-[4-(10-phenyl-9- anthryl)phenyl]-9H-carbazole (abbreviation: CzPA), 1,4-bis [4-(N-carbazolyl)phenyl]-2,3,5,6-tetraphenylbenzene, and the like.

Examples of the aromatic hydrocarbon that can be used for the composite material are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tort-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Other examples are pentacene, coronene, and the like. The aromatic hydrocarbon having a hole mobility of $1\times10^{-6}$ cm$^2$/Vs or more and having 14 to 42 carbon atoms is particularly preferable.

The aromatic hydrocarbon that can be used for the composite material may have a vinyl skeleton. Examples of the aromatic hydrocarbon having a vinyl group are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Other examples are high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), and poly[N,N'-bis(4-butylphenyl)-N,N'-bis(phenyl)benzidine] (abbreviation: poly-TPD).

The hole-transport layer 112 is a layer containing a substance having a hole-transport property. As the substance having a hole-transport property, those given above as the substances having hole-transport properties, which can be used for the above composite material, can be used. Note that detailed description is omitted to avoid repetition. Refer to the description of the composite material. Note that the hole-transport layer may contain the compound described in Embodiment 1 having a structure in which a carbazole skeleton is bonded to a benzofuropyridyl group or a benzothienopyridyl group through an arylene group.

The light-emitting layer 113 is a layer containing a light-emitting substance. The light-emitting layer 113 may be formed using a film containing only a light-emitting substance or a film in which an emission center substance is dispersed in a host material.

There is no particular limitation on a material that can be used as the light-emitting substance or the emission center substance in the light-emitting layer 113, and light emitted from the material may be either fluorescence or phosphorescence. Examples of the above light-emitting substance and emission center substance are fluorescent substances and phosphorescent substances. Examples of the fluorescent substance are N,N'-bis[4-(9-phenyl-9H-fluoren-9-yl)phenyl]-N,N'-diphenylpyrene-1,6-diamine (abbreviation: 1,6FLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N''',N'''',N''''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl) tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis {2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and the like. Examples of blue-emissive phosphorescent substances include an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), or tris[4-(3-biphenyl)-5-isopropyl-3-phenyl-4H-1,2,4-triazolato]iridium(III) (abbreviation: [Ir(iPrptz-3b)$_3$]); an organometallic iridium complex having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) or tris(1-methyl-5-phenyl-3-propyl-1H-1,2,4-triazolato)iridium(III) (abbreviation: [Ir(Prptz1-Me)$_3$]); an organometallic iridium complex having an imidazole skeleton, such as fac-tris[1-(2,6-diisopropylphenyl)-2-phenyl-1H-imidazole]iridium(III) (abbreviation: [Ir(iPrpmi)$_3$]), or tris[3-(2,6-dimethylphenyl)-7-methylimidazo[1,2-f]phenanthridinato]iridium(III) (abbreviation: [Ir(dmpimpt-Me)$_3$]); and an organometallic iridium complex in which a phenylpyridine compound having an electron-withdrawing group is a ligand, such as bis[2-(4',6'-difluorophenyl)pyridinato-N,C$^{2'}$]iridium(III) tetrakis(1-pyrazolyl)

borate (abbreviation: FIr6), bis[2-(4',6'-difluorophenyl)pyridinato-N,C$^{2'}$]iridium(III) picolinate (abbreviation: FIrpic), bis[2-(3,5-bistrifluoromethyl-phenyl)-pyridinato-N,C$^{2'}$]iridium(III) picolinate (abbreviation: [Ir(CF$_3$ppy)$_2$(pic)]), or bis[2-(4',6'-difluorophenyl)pyridinato-N,C$^{2'}$]iridium(III) acetylacetonate (abbreviation: FIr(acac)). Note that an organometallic iridium complex having a 4H-triazole skeleton has excellent reliability and emission efficiency and thus is especially preferable. Examples of green-emissive phosphorescent substances include an organometallic iridium complex having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$)), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), or (acetylacetonato)bis(4,6-diphenylpyrimidinato)iridium(III) (abbreviation: [Ir(dppm)$_2$(acac)]); an organometallic iridium complex having a pyrazine skeleton, such as (acetylacetonato)bis(3,5-dimethyl-2-phenylpyrazinato)iridium(III) (abbreviation: [Ir(mppr-Me)$_2$(acac)]) or (acetylacetonato)bis(5-isopropyl-3-methyl-2-phenylpyrazinato)iridium(III) (abbreviation: [Ir(mppr-iPr)$_2$(acac)]); an organometallic iridium complex having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), or bis(2-phenylquinolinato-N,C$^{2'}$)iridium(III) acetylacetonate (abbreviation: [Ir(pq)$_2$(acac)]); and a rare earth metal complex such as tris(acetylacetonato)(monophenanthroline)terbium(III) (abbreviation: [Tb(acac)$_3$(Phen)]). Note that an organometallic iridium complex having a pyrimidine skeleton has distinctively high reliability and emission efficiency and thus is especially preferable. Examples of red-emissive phosphorescent substances include an organometallic iridium complex having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), or bis[4,6-di(naphthalen-1-yl)pyrimidinato](dipivaloylmethanato)iridium(III) (abbreviation: [Ir(d1npm)$_2$(dpm)]); an organometallic iridium complex having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), or (acetylacetonato)bis[2,3-bis(4-fluorophenyl)quinoxalinato]iridium(III) (abbreviation: [Ir(Fdpq)$_2$(acac)]); an organometallic iridium complex having a pyridine skeleton, such as tris(1-phenylisoquinolinato-N,C$^{2'}$)iridium(III) (abbreviation: [Ir(piq)$_3$]) or bis(1-phenylisoquinolinato-N,C$^{2'}$)iridium(III)acetylacetonate (abbreviation: [Ir(piq)$_2$(acac)]); a platinum complex such as 2,3,7,8,12,13,17,18-octaethyl-21H,23H-porphyrin platinum(II) (abbreviation: PtOEP); and a rare earth metal complex such as tris(1,3-diphenyl-1,3-propanedionato)(monophenanthroline)europium(III) (abbreviation: [Eu(DBM)$_3$(Phen)]) or tris[1-(2-thenoyl)-3,3,3-trifluoroacetonato](monophenanthroline)europium(III) (abbreviation: [Eu(TTA)$_3$(Phen)]). Note that an organometallic iridium complex having a pyrimidine skeleton has distinctively high reliability and emission efficiency and thus is especially preferable. Further, because an organometallic iridium complex having a pyrazine skeleton can provide red light emission with favorable chromaticity, the use of the organometallic iridium complex in a white light-emitting element improves a color rendering property of the white light-emitting element. Note that the compound of one embodiment of the present invention having a structure in which a carbazole skeleton is bonded to a benzofuropyridyl group or a benzothienopyridyl group through an arylene group exhibits light, and thus can be used as an emission center material.

The material that can be used as the light-emitting substance may be selected from various substances as well as from the substances given above.

As a host material in which the emission center substance is dispersed, the compound of one embodiment of the present invention having a structure in which a carbazole skeleton is bonded to a benzofuropyridyl group or a benzothienopyridyl group through an arylene group is preferably used.

Since the compound having a structure in which a carbazole skeleton is bonded to a benzofuropyridyl group or a benzothienopyridyl group through an arylene group has a wide band gap and a high triplet excitation level, the compound can be suitably used as not only a host material in which an emission center substance emitting fluorescence in the visible region is dispersed but also a host material in which an emission center substance emitting high-energy light (such as an emission center substance emitting phosphorescence in the visible region) is dispersed. In particular, the compound can be suitably used as a host material in which an emission center substance emitting blue phosphorescence is dispersed. Needless to say, the compound can also be used as a host material in which an emission center substance emitting fluorescence having a longer wavelength than the blue light wavelength or an emission center substance emitting phosphorescence having a longer wavelength than the green light wavelength is dispersed. The carrier-transport property (specifically, the electron-transport property) of the compound is high; accordingly, a light-emitting element driven at low voltage can be provided.

In addition, it is effective to use the compound as a material of a carrier-transport layer (preferably an electron-transport layer) adjacent to a light-emitting layer. Since the compound has a wide band gap or a high triplet excitation level (T1 level), even when the emission center material is a material emitting high-energy light, such as a material emitting blue fluorescence or a material emitting green to blue phosphorescence, the energy of carriers that have recombined in a host material can be effectively transferred to the emission center substance. Thus, a light-emitting element having high emission efficiency can be fabricated. Note that in the case where the compound is used as a host material or a material of a carrier-transport layer, the emission center material is preferably, but not limited to, a substance having a narrower band gap between the HOMO level and the LUMO level than the compound or a substance having a lower singlet excitation level (S1 level) or a lower triplet excitation level (T1 level) than the compound.

Examples of materials that can be used as the host material in the case where the compound having a structure in which a carbazole skeleton is bonded to a benzofuropyridyl group or a benzothienopyridyl group through an arylene group is not used as the host material are described below.

The following are examples of materials having an electron-transport property: a metal complex such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ); a heterocyclic compound having a polyazole skeleton such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), or 2-[3-(dibenzothiophen-4-yl)phenyl]-1-phenyl-1H-benzimidazole (abbreviation: mDBTBIm-II); a heterocyclic compound having a diazine skeleton such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), or 4,6-bis[3-(4-dibenzothienyl)phenyl]pyrimidine (abbreviation: 4,6mDBTP2Pm-II); and a heterocyclic compound having a pyridine skeleton such as 3,5-bis[3-(9H-carbazol-9-yl)phenyl]pyridine (abbreviation: 35DCzPPy) or 1,3,5-tri[3-(3-pyridyl)phenyl]benzene (abbreviation: TmPyPB). Among the above materials, a heterocyclic compound having a diazine skeleton and a heterocyclic compound having a pyridine skeleton have high reliability and are thus preferable. Specifically, a heterocyclic compound having a diazine (pyrimidine or pyrazine) skeleton has a high electron-transport property to contribute to a reduction in driving voltage. Note that the above compound with a benzothienopyrimidine skeleton has a relatively high electron-transport property, and is classified as a material having an electron-transport property.

The following are examples of materials which have a hole-transport property: a compound having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl]spiro-9,9'-bifluoren-2-amine (abbreviation: PCBASF); a compound having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP); a compound having a thiophene skeleton such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV); and a compound having a furan skeleton such as 4,4',4"-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II). Among the above materials, a compound having an aromatic amine skeleton and a compound having a carbazole skeleton are preferable because these compounds are highly reliable and have high electron-transport properties to contribute to a reduction in driving voltage.

Note that when the emission center substance is a phosphorescent substance, a substance having a higher triplet excitation level (T1 level) than that of the phosphorescent substance is preferably selected as the host material, and when the light-emitting substance is a fluorescent substance, a substance having a wider band gap than that of the fluorescent substance is preferably selected as the host material. The light-emitting layer may contain a third substance in addition to the host material and the phosphorescent substance. Note that this statement does not exclude the possibility that the light-emitting layer contains a component other than the host materials, the phosphorescent substances, and the third substance.

Here, to achieve high emission efficiency of a light-emitting element that uses a phosphorescent substance, energy transfer between the host material and the phosphorescent substance will be considered. Carrier recombination occurs in both the host material and the phosphorescent substance; thus, efficient energy transfer from the host material to the phosphorescent substance is preferable to increase emission efficiency.

In this embodiment, a phosphorescent compound is used as the guest material. In an absorption spectrum of the phosphorescent compound, an absorption band that is considered to contribute to light emission most greatly is at an absorption wavelength corresponding to direct transition from a ground state to a triplet excited state and a vicinity of the absorption wavelength, which is on the longest wavelength side. Therefore, it is considered preferable that the emission spectrum (a fluorescence spectrum and a phosphorescence spectrum) of the host material overlap with the absorption band on the longest wavelength side in the absorption spectrum of the phosphorescent compound.

For example, most organometallic complexes, especially light-emitting iridium complexes, have a broad absorption band around 500 nm to 600 nm as the absorption band on the longest wavelength side. This absorption band is mainly based on a triplet MLCT (metal to ligand charge transfer) transition. Note that it is considered that the absorption band also includes absorptions based on a triplet $\pi$-$\pi^*$ transition and a singlet MLCT transition, and that these absorptions overlap each other to form a broad absorption band on the longest wavelength side in the absorption spectrum. Therefore, when an organometallic complex (especially iridium complex) is used as the guest material, it is preferable to make the broad absorption band on the longest wavelength side have a large overlap with the emission spectrum of the host material as described above.

Here, first, energy transfer from a host material in a triplet excited state will be considered. From the above-described discussion, it is preferable that, in energy transfer from a triplet excited state, the phosphorescence spectrum of the host material and the absorption band on the longest wavelength side of the guest material have a large overlap.

However, a question here is energy transfer from the host molecule in the singlet excited state. In order to efficiently perform not only energy transfer from the triplet excited state but also energy transfer from the singlet excited state, the host material is preferably designed such that not only its phosphorescence spectrum but also its fluorescence spectrum overlaps with the absorption band on the longest wavelength side of the guest material. In other words, when the host material is designed so as to have its fluorescence spectrum in a position similar to that of its phosphorescence spectrum, it is possible to achieve efficient energy transfer from the host material in both the singlet excited state and the triplet excited state.

However, in general, the S1 level differs greatly from the T1 level (S1 level>T1 level); therefore, the fluorescence emission wavelength also differs greatly from the phosphorescence emission wavelength (fluorescence emission wavelength<phosphorescence emission wavelength). For example, 4,4'-di(N-carbazolyl)biphenyl (abbreviation: CBP), which is commonly used in a light-emitting element containing a phosphorescent compound, has a phosphorescence spectrum around 500 nm and has a fluorescence spectrum around 400 nm, which are largely different by about 100 nm. This example also shows that it is extremely difficult to design a host material so as to have its fluorescence spectrum in a position similar to that of its phosphorescence spectrum.

Also, since fluorescence is emitted from an energy level higher than that of phosphorescence, the T1 level of a host material whose fluorescence spectrum corresponds to a wavelength close to an absorption spectrum of a guest material on the longest wavelength side is lower than the T1 level of the guest material.

Thus, in the case where a phosphorescent substance is used as the emission center substance, it is preferable that the light-emitting layer include a third substance in addition to the host material and the emission center substance and a combination of the host material and the third substance form an exciplex (also referred to as an excited complex).

In that case, at the time of recombination of carriers (electrons and holes) in the light-emitting layer, the host material and the third substance form an exciplex. A fluorescence spectrum of the exciplex is on a longer wavelength side than a fluorescence spectrum of the host material alone or the third substance alone. Therefore, energy transfer from a singlet excited state can be maximized while the T1 levels of the host material and the third substance are kept higher than the T1 level of the guest material. In addition, the exciplex is in a state where the T1 level and the 51 level are close to each other; therefore, the fluorescence spectrum and the phosphorescence spectrum exist at substantially the same position. Accordingly, both the fluorescence spectrum and the phosphorescence spectrum of the exciplex can have a large overlap with an absorption corresponding to transition of the guest molecule from the singlet ground state to the triplet excited state (a broad absorption band of the guest molecule existing on the longest wavelength side in the absorption spectrum), and thus a light-emitting element having high energy transfer efficiency can be obtained.

As the third substance, the above material which can be used as the host material or additives can be used. There is no particular limitation on the host materials and the third substance as long as they can form an exciplex; a combination of a compound which readily accepts electrons (a compound having an electron-transport property) and a compound which readily accepts holes (a compound having a hole-transport property) is preferably employed.

In the case where a compound having an electron-transport property and a compound having a hole-transport property are used for the host material and the third substance, carrier balance can be controlled by the mixture ratio of the compounds. Specifically, the ratio of the host material to the third substance (or additive) is preferably from 1:9 to 9:1. Note that in that case, the following structure may be employed: a light-emitting layer in which one kind of an emission center substance is dispersed is divided into two layers, and the two layers have different mixture ratios of the host material to the third substance. With this structure, the carrier balance of the light-emitting element can be optimized, so that the lifetime of the light-emitting element can be improved. Furthermore, one of the light-emitting layers may be a hole-transport layer and the other of the light-emitting layers may be an electron-transport layer.

In the case where the light-emitting layer having the above-described structure is formed using a plurality of materials, the light-emitting layer can be formed using co-evaporation by a vacuum evaporation method; or an inkjet method, a spin coating method, a dip coating method, or the like using a solution of the materials.

The electron-transport layer 114 is a layer containing a substance having an electron-transport property. For example, the electron-transport layer 114 is formed using a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq), or the like. A metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), or the like can also be used. Other than the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances given here are mainly ones having an electron mobility of $10^{-6}$ cm$^2$/Vs or higher. Note that any substance other than the above substances may be used for the electron-transport layer as long as the substance has an electron-transport property higher than a hole-transport property.

The compound having a structure in which a carbazole skeleton is bonded to a benzofuropyridyl group or a benzothienopyridyl group through an arylene group may be used as a material contained in the electron-transport layer 114. Since the compound of one embodiment of the present invention having a structure in which a carbazole skeleton is bonded to a benzofuropyridyl group or a benzothienopyridyl group through an arylene group has a wide band gap and a high T1 level, excitation energy in the light-emitting layer can be prevented from transferring to the electron-transport layer 114 and a decrease in emission efficiency due to the energy transfer can be suppressed, so that a light-emitting element with high emission efficiency can be provided. Moreover, the compound of one embodiment of the present invention has a high carrier-transport property; thus, a light-emitting element driven at low voltage can be provided.

The electron-transport layer is not limited to a single layer, and may be a stack including two or more layers containing any of the above substances.

Between the electron-transport layer and the light-emitting layer, a layer that controls transport of electron carriers may be provided. This is a layer formed by addition of a small amount of a substance having a high electron-trapping property to the aforementioned materials having a high electron-transport property, and the layer is capable of adjusting carrier balance by retarding transport of electron carriers. Such a structure is very effective in preventing a problem (such as a reduction in element lifetime) caused when electrons pass through the light-emitting layer.

It is preferable that the host material in the light-emitting layer and a material of the electron-transport layer have the same skeleton, in which case transfer of carriers can be smooth and thus the driving voltage can be reduced. Moreover, it is effective that the host material and the material of the electron-transport layer be the same material.

The electron-injection layer 115 may be provided in contact with the second electrode 102 between the electron-transport layer 114 and the second electrode 102. For the electron-injection layer 115, lithium, calcium, lithium fluoride (LiF), cesium fluoride (CsF), or calcium fluoride ($CaF_2$) can be used. A composite material of a substance having an electron-transport property and a substance exhibiting an electron-donating property (hereinafter, simply referred to as electron-donating substance) with respect to the substance having an electron-transport property can also be used. Examples of the electron-donating substance include an alkali metal, an alkaline earth metal, and compounds thereof. Note that such a composite material is preferably used for the electron-injection layer 115, in which case electrons are injected efficiently from the second electrode 102. With this structure, a conductive material as well as a material having a low work function can be used for the cathode.

For the electrode functioning as a cathode, any of metals, alloys, electrically conductive compounds, and mixtures thereof which have a low work function (specifically, a work function of 3.8 eV or less) or the like can be used. Specific examples of such a cathode material include elements that belong to Groups 1 and 2 of the periodic table, i.e., lithium (Li), cesium (Cs), magnesium (Mg), calcium (Ca), and strontium (Sr), alloys thereof (e.g., MgAg or AlLi), rare earth metals such as europium (Eu) and ytterbium (Yb), alloys thereof, and the like. However, when the electron-injection layer is provided between the second electrode 102 and the electron-transport layer, for the second electrode 102, any of a variety of conductive materials such as Al, Ag, ITO, or indium tin oxide containing silicon or silicon oxide can be used regardless of the work function. Films of these electrically conductive materials can be formed by a sputtering method, an inkjet method, a spin coating method, or the like.

Any of a variety of methods can be used to form the EL layer 103 regardless whether it is a dry process or a wet process. For example, a vacuum evaporation method, an inkjet method, a spin coating method, or the like may be used. Different formation methods may be used for the electrodes or the layers.

In addition, the electrode may be formed by a wet method using a sol-gel method, or by a wet method using paste of a metal material. Alternatively, the electrode may be formed by a dry method such as a sputtering method or a vacuum evaporation method.

Note that the structure of the EL layer provided between the first electrode 101 and the second electrode 102 is not limited to the above structure. However, it is preferable that a light-emitting region where holes and electrons recombine be positioned away from the first electrode 101 and the second electrode 102 so as to prevent quenching due to the proximity of the light-emitting region and a metal used for an electrode or a carrier-injection layer.

Further, in order that transfer of energy from an exciton generated in the light-emitting layer can be inhibited, preferably, the hole-transport layer and the electron-transport layer which are in direct contact with the light-emitting layer, particularly a carrier-transport layer in contact with a side closer to the light-emitting region in the light-emitting layer 113 is formed with a substance having a wider energy gap than the light-emitting substance of the light-emitting layer or the emission center substance included in the light-emitting layer.

In the light-emitting element having the above-described structure, current flows due to a potential difference between the first electrode 101 and the second electrode 102, and holes and electrons recombine in the light-emitting layer 113 which contains a substance having a high light-emitting property, so that light is emitted. In other words, a light-emitting region is formed in the light-emitting layer 113.

Light is extracted out through one or both of the first electrode 101 and the second electrode 102. Therefore, one or both of the first electrode 101 and the second electrode 102 are light-transmitting electrodes. In the case where only the first electrode 101 is a light-transmitting electrode, light is extracted from the substrate side through the first electrode 101. In contrast, when only the second electrode 102 is a light-transmitting electrode, light is extracted from the side opposite to the substrate side through the second electrode 102. In the case where both the first electrode 101 and the second electrode 102 are light-transmitting electrodes, light is extracted from both the substrate side and the side opposite to the substrate side through the first electrode 101 and the second electrode 102.

Since the light-emitting element of this embodiment is formed using the compound of one embodiment of the present invention having a wide energy gap, efficient light emission can be achieved even if an emission center substance is any of a substance emitting fluorescence in the visible region and a substance emitting green to blue phosphorescence, which have a wide energy gap, and the light-emitting element can have high emission efficiency. Thus, a light-emitting element with lower power consumption can be provided. Furthermore, the compound having a structure in which a carbazole skeleton is bonded to a benzofuropyridyl group or a benzothienopyridyl group through an arylene group has a high carrier-transport property; thus, a light-emitting element having low driving voltage can be provided.

Such a light-emitting element may be fabricated using a substrate made of glass, plastic, or the like as a support. A plurality of such light-emitting elements are formed over one substrate, thereby forming a passive matrix light-emitting device. Alternatively, a transistor may be formed over a substrate made of glass, plastic, or the like, and the light-emitting element may be fabricated over an electrode electrically connected to the transistor. In this manner, an active matrix light-emitting device in which the driving of the light-emitting element is controlled by the transistor can be fabricated. Note that a structure of the transistor is not particularly limited. Either a staggered TFT or an inverted staggered TFT may be employed. In addition, the crystallinity of a semiconductor used for the TFT is not particularly limited. In addition, a driver circuit formed in a TFT substrate may be formed with n-channel FTs and p-channel TFTs, or with either n-channel TFTs or p-channel TFTs. The semiconductor layer for forming the PFTs may be formed using any material as long as the material exhibits semiconductor characteristics; for example, an element belonging to Group 14 of the periodic table such as silicon (Si) and germanium (Ge), a compound such as gallium arsenide and indium phosphide, an oxide such as zinc oxide and tin oxide, and the like can be given. For the oxide exhibiting semiconductor characteristics (oxide semiconductor), composite oxide of an element selected from indium, gallium, aluminum, zinc, and tin can be used. Examples thereof are zinc oxide (ZnO), indium oxide containing zinc oxide (indium zinc oxide), and oxide containing indium oxide, gallium oxide, and zinc oxide (IGZO: indium gallium zinc oxide). An organic semiconductor may also be used. The semiconductor layer may have either a crystalline structure or an amorphous structure. Specific examples of the crystalline semiconductor layer are a single crystal semiconductor, a polycrystalline semiconductor, and a microcrystalline semiconductor.

Embodiment 3

In this embodiment is described one mode of a light-emitting element having a structure in which a plurality of light-emitting units are stacked (hereinafter, also referred to as stacked-type element), with reference to FIG. 1B. This light-emitting element includes a plurality of light-emitting units between a first electrode and a second electrode. Each light-emitting unit can have the same structure as the EL layer 103 which is described in Embodiment 2. In other words, the light-emitting element described in Embodiment 2 is a light-emitting element having one light-emitting unit while the light-emitting element described in this embodiment is a light-emitting element having a plurality of light-emitting units.

Figure 1B:
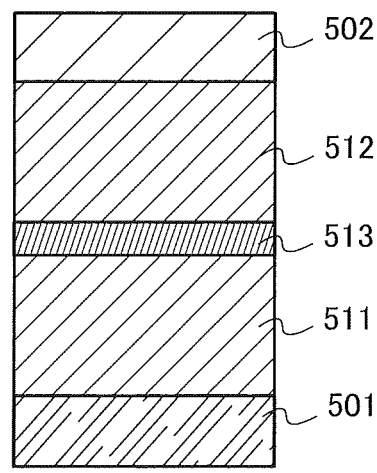

In FIG. 1B, a first light-emitting unit 511 and a second light-emitting unit 512 are stacked between a first electrode 501 and a second electrode 502, and a charge generation layer 513 is provided between the first light-emitting unit 511 and the second light-emitting unit 512. The first electrode 501 and the second electrode 502 respectively correspond to the first electrode 101 and the second electrode 102 in Embodiment 2, and materials described in Embodiment 2 can be used. Further, the structures of the first light-emitting unit 511 and the second light-emitting unit 512 may be the same or different.

The charge generation layer 513 includes a composite material of an organic compound and a metal oxide. As this composite material of an organic compound and a metal oxide, the composite material that can be used for the hole-injection layer and described in Embodiment 2 can be used. As the organic compound, any of a variety of compounds such as aromatic amine compounds, carbazole compounds, aromatic hydrocarbons, and high molecular compounds (oligomers, dendrimers, polymers, or the like) can be used. Note that the organic compound preferably has a hole mobility of $1\times10^{-6}$ cm$^2$/Vs or more. However, any other substance may be used as long as the substance has a hole-transport property higher than an electron-transport property. Since a composite material of an organic compound and a metal oxide is excellent in carrier-injection property and carrier-transport property, low voltage driving and low current driving can be achieved. Note that in the light-emitting unit whose anode side surface is in contact with the charge generation layer, a hole-transport layer is not necessarily provided because the charge generation layer can also function as the hole-transport layer.

The charge generation layer 513 may have a stacked-layer structure of a layer containing the composite material of an organic compound and a metal oxide and a layer containing another material. For example, a layer containing the composite material of an organic compound and a metal oxide may be combined with a layer containing a compound of a substance selected from electron-donating substances and a compound having a high electron-transport property. Moreover, the charge generation layer 513 may be formed by combining a layer containing the composite material of an organic compound and a metal oxide with a transparent conductive film.

The charge generation layer 513 provided between the first light-emitting unit 511 and the second light-emitting unit 512 may have any structure as long as electrons can be injected to a light-emitting unit on one side and holes can be injected to a light-emitting unit on the other side when a voltage is applied between the first electrode 501 and the second electrode 502. For example, in FIG. 1B, any layer can be used as the charge generation layer 513 as long as the layer injects electrons into the first light-emitting unit 511 and holes into the second light-emitting unit 512 when a voltage is applied such that the potential of the first electrode is higher than that of the second electrode.

Although the light-emitting element having two light-emitting units is described in this embodiment, the present invention can be similarly applied to a light-emitting element in which three or more light-emitting units are stacked. With a plurality of light-emitting units partitioned by the charge generation layer between a pair of electrodes, as in the light-emitting element according to this embodiment, light with high luminance can be obtained while current density is kept low; thus, a light-emitting element having a long lifetime can be obtained. In addition, a low power consumption light-emitting device which can be driven at low voltage can be achieved.

By making the light-emitting units emit light of different colors from each other, the light-emitting element can provide light emission of a desired color as a whole. For example, by forming a light-emitting element having two light-emitting units such that the emission color of the first light-emitting unit and the emission color of the second light-emitting unit are complementary colors, the light-emitting element can provide white light emission as a whole. Note that the word "complementary" means color relationship in which an achromatic color is obtained when colors are mixed. In other words, when lights obtained from substances which emit light of complementary colors are mixed, white light emission can be obtained. Further, the same can be applied to a light-emitting element having three light-emitting units. For example, the light-emitting element as a whole can provide white light emission when the emission color of the first light-emitting unit is red, the emission color of the second light-emitting unit is green, and the emission color of the third light-emitting unit is blue. Alternatively, in the case of employing a light-emitting element in which a phosphorescent emission center substance is used for a light-emitting layer of one light-emitting unit and a fluorescent emission center substance is used for a light-emitting layer of the other light-emitting unit, both fluorescence and phosphorescence can be efficiently emitted from the light-emitting element. For example, when red phosphorescence and green phosphorescence are obtained from one light-emitting unit and blue fluorescence is obtained from the other light-emitting unit, white light with high emission efficiency can be obtained.

Since the light-emitting element of this embodiment contains the compound having a structure in which a carbazole skeleton is bonded to a benzofuropyridyl group or a benzothienopyridyl group through an arylene group, the light-emitting element can have high emission efficiency or operate at low driving voltage. In addition, since light emission with high color purity which is derived from the emission center substance can be obtained from the light-emitting unit including the heterocyclic compound, color adjustment of the light-emitting element as a whole is easy.

Note that this embodiment can be combined with any of the other embodiments as appropriate.

Embodiment 4

In this embodiment, a light-emitting device that uses a light-emitting element including the compound having a structure in which a carbazole skeleton is bonded to a benzofuropyridyl group or a benzothienopyridyl group through an arylene group is described.

Figure 2A:
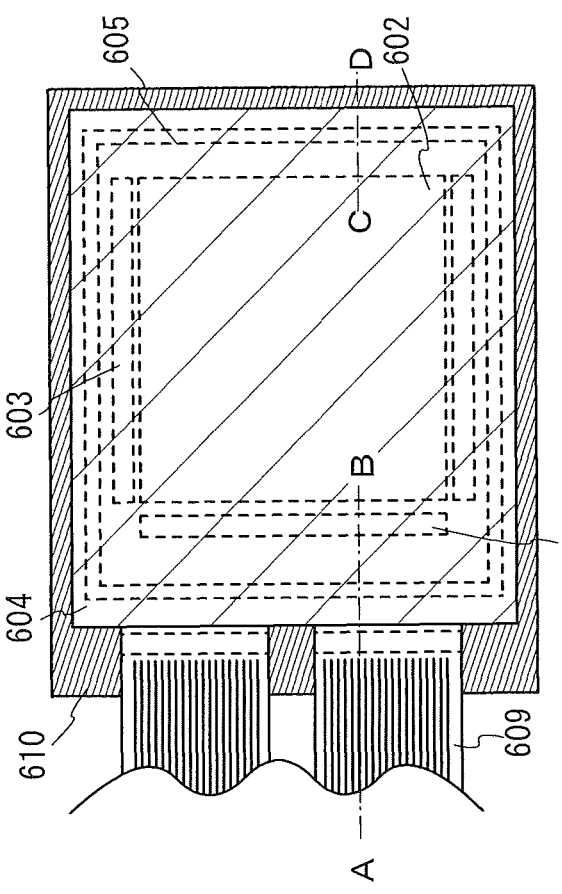
FIGS. 2A and 2B are conceptual diagrams of an active matrix light-emitting device.
Figure 2B:
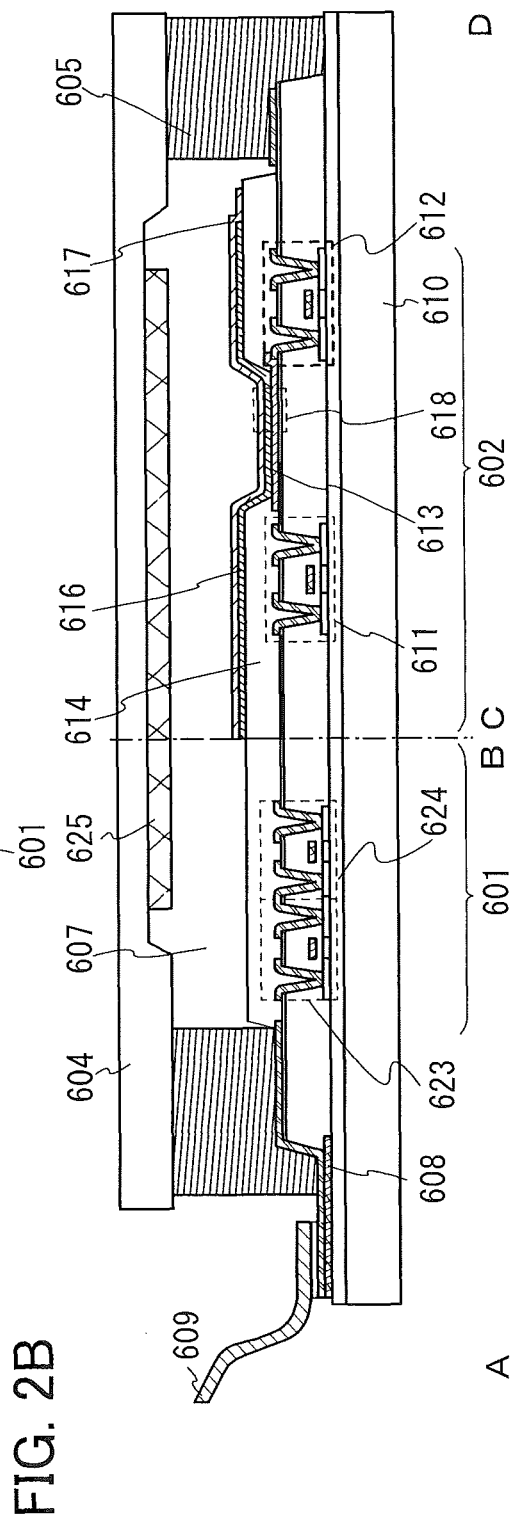

In this embodiment, explanation will be given with reference to FIGS. 2A and 2B of an example of the light-emitting device fabricated using a light-emitting element including the compound having a structure in which a carbazole skeleton is bonded to a benzofuropyridyl group or a benzothienopyridyl group through an arylene group. Note that FIG. 2A is a top view of the light-emitting device and FIG. 2B is a cross-sectional view taken along the lines A-B and C-D in FIG. 2A. This light-emitting device includes a driver circuit portion (source side driver circuit) 601, a pixel portion 602, and a driver circuit portion (gate side driver circuit) 603, which control light emission of a light-emitting element and denoted by dotted lines. A reference numeral 604 denotes a sealing substrate; 625, a desiccant; 605, a sealing material; and 607, a space surrounded by the sealing material 605.

Reference numeral 608 denotes a wiring for transmitting signals to be input to the source side driver circuit 601 and the gate side driver circuit 603 and receiving signals such as a video signal, a clock signal, a start signal, and a reset signal from an FPC (flexible printed circuit) 609 serving as an external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure is explained with reference to FIG. 2B. The driver circuit portion and the pixel portion are formed over an element substrate 610; here, the source line driver circuit 601, which is a driver circuit portion, and one of the pixels in the pixel portion 602 are shown.

As the source line driver circuit 601, a CMOS circuit in which an n-channel TFT 623 and a p-channel TFT 624 are combined is formed. In addition, the driver circuit may be formed with any of a variety of circuits such as a CMOS circuit, a PMOS circuit, and an NMOS circuit. Although a driver integrated type in which the driver circuit is formed over the substrate is illustrated in this embodiment, the driver circuit is not necessarily formed over the substrate, and the driver circuit can be formed outside, not over the substrate.

The pixel portion 602 includes a plurality of pixels including a switching TFT 611, a current controlling TFT 612, and a first electrode 613 electrically connected to a drain of the current controlling TFT 612. Note that to cover an end portion of the first electrode 613, an insulator 614 is formed, for which a positive photosensitive resin film is used here.

In order to improve coverage of a film formed over the insulator 614, the insulator 614 is formed to have a curved surface with curvature at its upper or lower end portion. For example, in the case where a positive photosensitive acrylic resin is used for a material of the insulator 614, only the upper end portion of the insulator 614 preferably has a surface with a curvature radius (0.2 μm to 3 μm). As the insulator 614, either a negative photosensitive material or a positive photosensitive material can be used.

An EL layer 616 and a second electrode 617 are formed over the first electrode 613. As a material used for the first electrode 613 which functions as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack including a titanium nitride film and a film containing aluminum as its main component, a stack including three layers of a titanium nitride an, a film containing aluminum as its main component, and a titanium nitride film, or the like can be used. The stacked structure achieves low wiring resistance, a favorable ohmic contact, and a function as an anode.

The EL layer 616 is formed by any of a variety of methods such as an evaporation method using an evaporation mask, an inkjet method, and a spin coating method. The EL layer 616 contains the compound having a structure in which a carbazole skeleton is bonded to a benzofuropyridyl group or a benzothienopyridyl group through an arylene group. Further, for another material included in the EL layer 616, any of low molecular-weight compounds and polymeric compounds (including oligomers and dendrimers) may be used.

As a material used for the second electrode 617, which is formed over the EL layer 616 and functions as a cathode, a material having a low work function (e.g., Al, Mg, Li, Ca, or an alloy or compound thereof, such as MgAg, MgIn, or AlLi) is preferably used. In the case where light generated in the EL layer 616 passes through the second electrode 617, a stack including a thin metal film and a transparent conductive film (e.g., ITO, indium oxide containing zinc oxide at 2 wt % or higher and 20 wt % or lower, indium tin oxide containing silicon, or zinc oxide (ZnO)) is preferably used for the second electrode 617.

Note that the light-emitting element is formed with the first electrode 613, the EL layer 616, and the second electrode 617. The light-emitting element has the structure described in Embodiment 3. In the light-emitting device of this embodiment, the pixel portion, which includes a plurality of light-emitting elements, may include both the light-emitting element with the structure described in Embodiment 3 and a light-emitting element with a structure other than those.

The sealing substrate 604 is attached to the element substrate 610 with the sealing material 605, so that the light-emitting element 618 is provided in the space 607 surrounded by the element substrate 610, the sealing substrate 604, and the sealing material 605. The space 607 is filled with a filler. The filler may be an inert gas (such as nitrogen or argon), a resin, or a resin and/or a desiccant.

An epoxy-based resin or glass frit is preferably used for the sealing material 605. It is preferable that such a material do not transmit moisture or oxygen as much as possible. As the sealing substrate 604, a glass substrate, a quartz substrate, or a plastic substrate formed of fiber reinforced plastic (FRP), poly(vinyl fluoride) (PVF), a polyester, an acrylic resin, or the like can be used.

As described above, the light-emitting device fabricated by using the light-emitting element including the compound having a structure in which a carbazole skeleton is bonded to a benzofuropyridyl group or a benzothienopyridyl group through an arylene group can be obtained.

FIGS. 3A and 3B illustrates examples of light-emitting devices in which full color display is achieved by forming a light-emitting element exhibiting white light emission and providing a coloring layer (a color filter) and the like. In FIG. 3A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition wall 1025, an EL layer 1028, a second electrode 1029 of the light-emitting elements, a sealing substrate 1031, a sealant 1032, and the like are illustrated.

In FIG. 3A, coloring layers (a red coloring layer 1034R, a green coloring layer 1034G, and a blue coloring layer 1034B) are provided on a transparent base material 1033. Further, a black layer (a black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 3A, light emitted from some of the light-emitting layers does not pass through the coloring layers, while light emitted from the others of the light-emitting layers passes through the coloring layers. Since light which does not pass through the coloring layers is white and light which passes through any one of the coloring layers is red, blue, or green, an image can be displayed using pixels of the four colors.

FIG. 3B illustrates an example in which coloring layers (a red coloring layer 1034R, a green coloring layer 1034G, and a blue coloring layer 1034B) are formed between the gate insulating film 1003 and the first interlayer insulating film 1020. As shown in FIG. 3B, the coloring layers may be provided between the substrate 1001 and the sealing substrate 1031.

Figure 4:
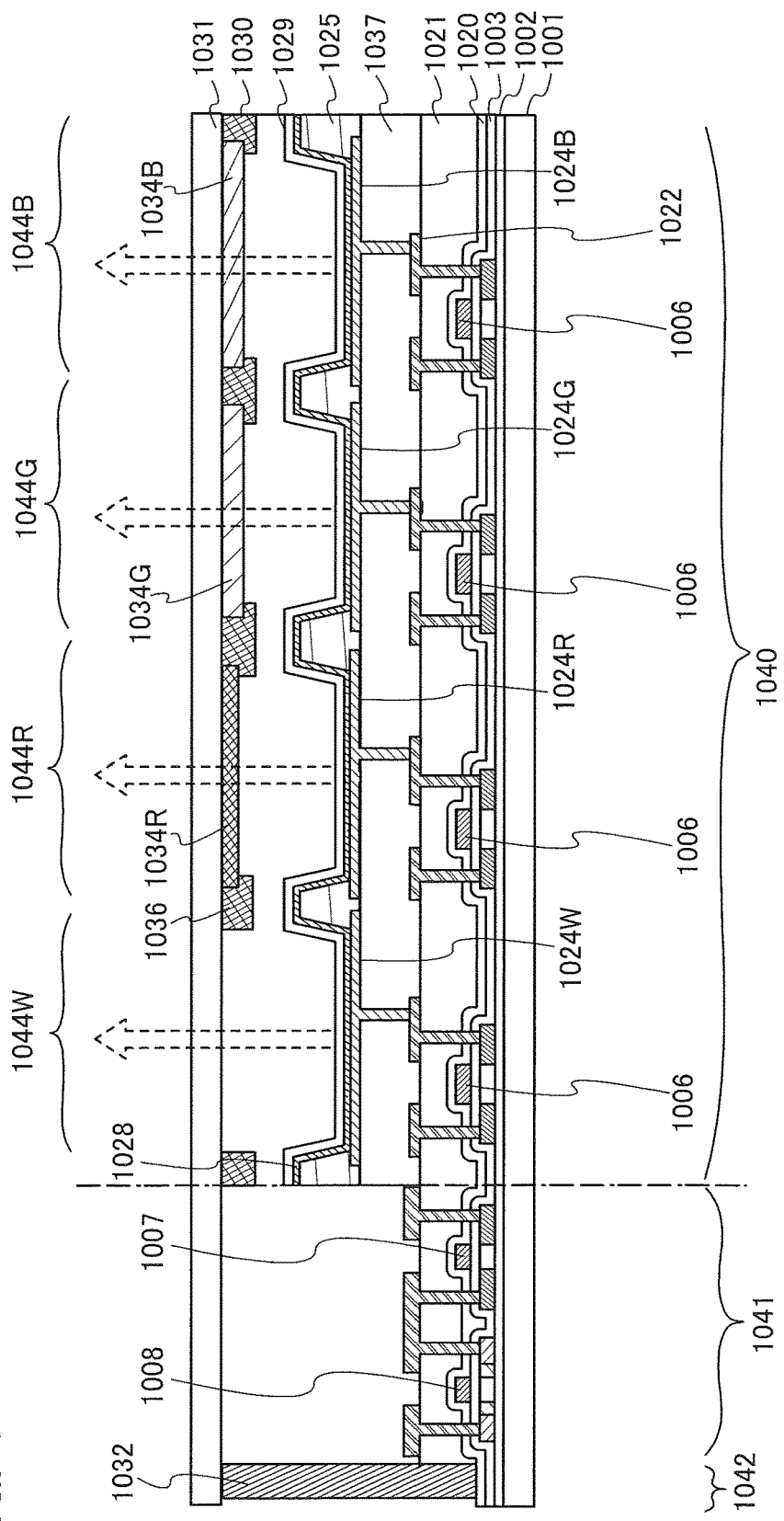
FIG. 4 is a conceptual diagram of an active matrix light-emitting device.

The above-described light-emitting device has a structure in which light is extracted from the substrate 1001 side where the TFTs are formed (a bottom emission structure), but may have a structure in which light is extracted from the sealing substrate 1031 side (a top emission structure). FIG. 4 is a cross-sectional view of a light-emitting device having a top emission structure. In this case, a substrate which does not transmit light can be used as the substrate 1001. The process up to the step of forming a connection electrode which connects the TFT and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film, and can alternatively be formed using any other various materials.

The first electrodes 1024W, 1024R, 1024G, and 1024B of the light-emitting elements each serve as an anode here, but may serve as a cathode. Further, in the case of a light-emitting device having a top emission structure as illustrated in FIG. 4, the first electrodes are preferably reflective electrodes. The EL layer 1028 is formed to have a structure similar to the structure described in Embodiment 2, with which white light emission can be obtained.

In FIGS. 3A and 3B and FIG. 4, the structure of the EL layer for providing white light emission can be achieved by, for example, using a plurality of light-emitting layers or using a plurality of light-emitting units. Note that the structure to provide white light emission is not limited to the above.

In the case of a top emission structure as illustrated in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (the black matrix) 1035 which is positioned between pixels. The coloring layers (the red coloring layer 1034R, the green coloring layer 1034G, and the blue coloring layer 1034B) and the black layer (the black matrix) may be covered with the overcoat layer. Note that a light-transmitting substrate is used as the sealing substrate 1031.

Although an example in which full color display is performed using four colors of red, green, blue, and white is shown here, there is no particular limitation and full color display using three colors of red, green, and blue or four colors of red, green, blue, and yellow may be performed.

Since the light-emitting device of this embodiment uses the light-emitting element described in Embodiment 3 (the light-emitting element including the compound having a structure in which a carbazole skeleton is bonded to a benzofuropyridyl group or a benzothienopyridyl group through an arylene group), the light-emitting device can have favorable characteristics. Specifically, the compound having a structure in which a carbazole skeleton is bonded to a benzofuropyridyl group or a benzothienopyridyl group through an arylene group has a wide energy gap and a high triplet excitation level (T1 level) and can inhibit energy transfer from a light-emitting substance; thus, a light-emitting element having high emission efficiency can be provided, leading to a light-emitting device having reduced power consumption. Furthermore, the compound having a structure in which a carbazole skeleton is bonded to a benzofuropyridyl group or a benzothienopyridyl group through an arylene group has a high carrier-transport property, so that a light-emitting element driven at low voltage can be provided, leading to a light-emitting device driven at low voltage.

Figure 5A:
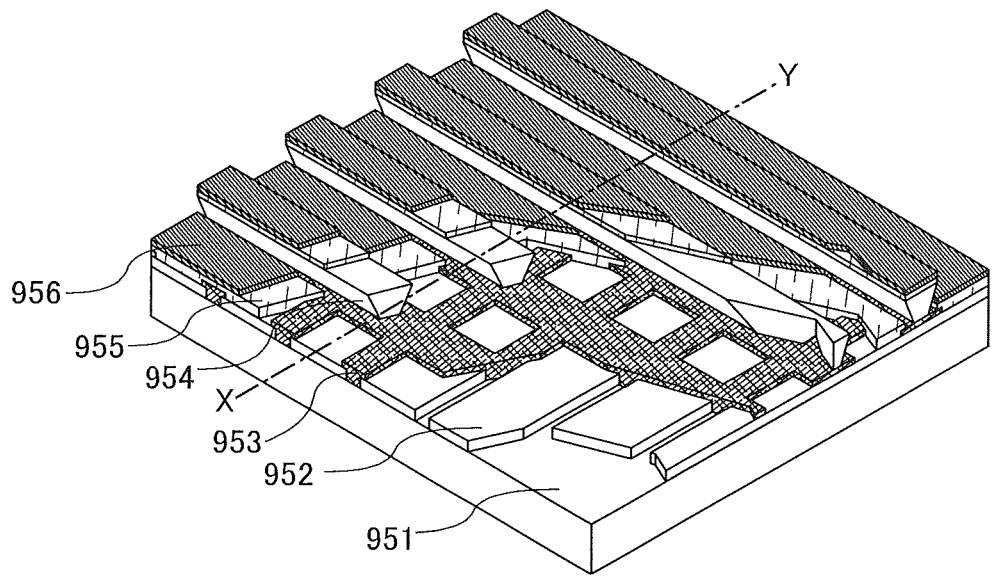
FIGS. 5A and 5B are conceptual diagrams of a passive matrix light-emitting device.
Figure 5B:
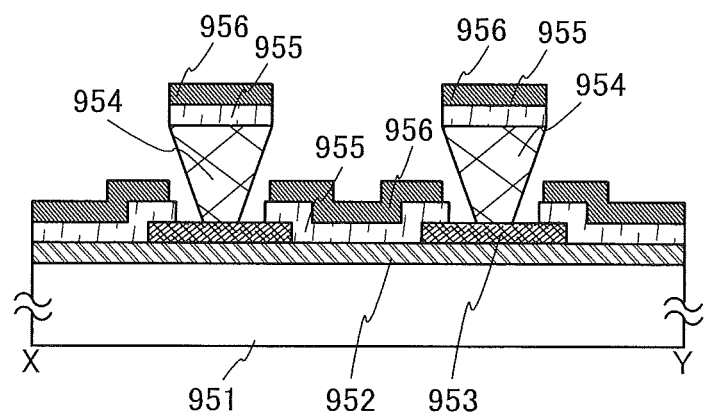

An active matrix light-emitting device is described above, whereas a passive matrix light-emitting device is described below. FIGS. 5A and 5B illustrate a passive matrix light-emitting device fabricated by application of one embodiment of the present invention. FIG. 5A is a perspective view of the light-emitting device, and FIG. 5B is a cross-sectional view of FIG. 5A taken along line X-Y. In FIGS. 5A and 5B, over a substrate 951, an EL layer 955 is provided between an electrode 952 and an electrode 956. An edge portion of the electrode 952 is covered with an insulating layer 953. A partition layer 954 is provided over the insulating layer 953. The sidewalls of the partition layer 954 slope so that the distance between one sidewall and the other sidewall gradually decreases toward the surface of the substrate. In other words, a cross section taken along the direction of the short side of the partition layer 954 is trapezoidal, and the base (a side which is in the same direction as a plane direction of the insulating layer 953 and in contact with the insulating layer 953) is shorter than the upper side (a side which is in the same direction as the plane direction of the insulating layer 953 and not in contact with the insulating layer 953). By providing the partition layer 954 in such a manner, a defect of the light-emitting element due to static electricity or the like can be prevented. The passive matrix light-emitting device can also be driven with low power consumption, by including the light-emitting element described in Embodiment 3 (the light-emitting element having a structure in which a carbazole skeleton is bonded to a benzofuropyridyl group or a benzothienopyridyl group through an arylene group) capable of operating at low driving voltage. In addition, the light-emitting device can be driven with less power consumption by including the light-emitting element described in Embodiment 3 because the element has high emission efficiency due to the compound having a structure in which a carbazole skeleton is bonded to a benzofuropyridyl group or a benzothienopyridyl group through an arylene group.

Note that in this specification and the like, a transistor or a light-emitting element can be formed using any of a variety of substrates, for example. The type of a substrate is not limited to a certain type. As the substrate, a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, or the like can be used, for example. As an example of a glass substrate, a barium borosilicate glass substrate, an aluminoborosilicate glass substrate, a soda lime glass substrate, or the like can be given. Examples of the flexible substrate, the attachment film, the base film, and the like are substrates of plastics typified by polyethylene terephthalate (PET), polyethylene naphthalate (PEN), polyether sulfone (PES), and polytetrafluoroethylene (PTFE). Another example is a synthetic resin such as acrylic. Alternatively, polypropylene, polyester, polyvinyl fluoride, polyvinyl chloride, or the like can be used. Alternatively, polyamide, polyimide, aramid, epoxy, an inorganic vapor deposition film, paper, or the like can be used. Specifically, the use of semiconductor substrates, single crystal substrates, SOI substrates, or the like enables the manufacture of small-sized transistors with a small variation in characteristics, size, shape, or the like and with high current capability. A circuit using such transistors achieves lower power consumption of the circuit or higher integration of the circuit.

Alternatively, a flexible substrate may be used as the substrate, and the transistor or the light-emitting element may be provided directly on the flexible substrate. Still alternatively, a separation layer may be provided between the substrate and the transistor. The separation layer can be used when part or the whole of a semiconductor device formed over the separation layer is separated from the substrate and transferred onto another substrate. In such a case, the transistor can be transferred to a substrate having low heat resistance or a flexible substrate. For the separation layer, a stack including inorganic films, which are a tungsten film and a silicon oxide film, or an organic resin film of polyimide or the like formed over a substrate can be used, for example.

In other words, a transistor or a light-emitting element may be formed using one substrate, and then transferred to another substrate. Examples of a substrate to which a transistor or a light-emitting element is transferred include, in addition to the above-described substrates over which transistors can be formed, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. When such a substrate is used, a transistor with excellent characteristics or a transistor with low power consumption can be formed, a device with high durability or high heat resistance can be provided, or reduction in weight or thickness can be achieved.

Since many minute light-emitting elements arranged in a matrix in the light-emitting device described above can each be controlled, the light-emitting device can be suitably used as a display device for displaying images.

Embodiment 5

In this embodiment, electronic devices each including the light-emitting element described in Embodiment 3 are described. The light-emitting element described in Embodiment 3 includes the compound of one embodiment of the present invention having a structure in which a carbazole skeleton is bonded to a benzofuropyridyl group or a benzothienopyridyl group through an arylene group and thus has reduced power consumption; as a result, the electronic devices described in this embodiment can each include a display portion having reduced power consumption. In addition, the electronic devices can be driven at low voltage since the light-emitting element described in Embodiment 3 is driven at low voltage.

Examples of the electronic device to which the above light-emitting element is applied include television devices (also referred to as TV or television receivers), monitors for computers and the like, cameras such as digital cameras and digital video cameras, digital photo frames, cellular phones (also referred to as mobile phones or mobile phone devices), portable game machines, portable information terminals, audio playback devices, large game machines such as pachinko machines, and the like. Specific examples of these electronic devices are given below.

Figure 6A:
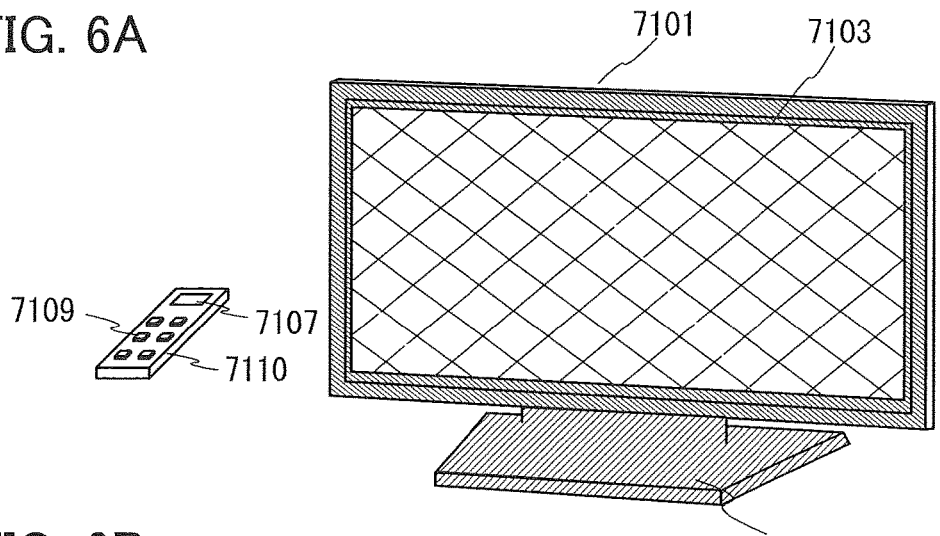
FIGS. 6A to 6D illustrate electronic devices.

FIG. 6A illustrates an example of a television device. In the television device, a display portion 7103 is incorporated in a housing 7101. In addition, here, the housing 7101 is supported by a stand 7105. The display portion 7103 enables display of images and includes light-emitting elements which are the same as the light-emitting element described in Embodiment 3 and arranged in a matrix. The light-emitting elements each include the compound having a structure in which a carbazole skeleton is bonded to a benzofuropyridyl group or a benzothienopyridyl group through an arylene group and thus can have high emission efficiency and low driving voltage. Therefore, the television device including the display portion 7103 which is formed using the light-emitting elements can have reduced power consumption and low driving voltage.

The television device can be operated with an operation switch of the housing 7101 or a separate remote controller 7110. With operation keys 7109 of the remote controller 7110, channels and volume can be controlled and images displayed on the display portion 7103 can be controlled.

Furthermore, the remote controller 7110 may be provided with a display portion 7107 for displaying data output from the remote controller 7110.

Note that the television device is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

Figure 6B:
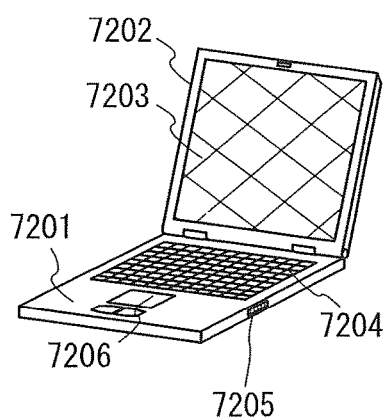

FIG. 6B illustrates a computer, which includes a main body 7201, a housing 7202, a display portion 7203, a keyboard 7204, an external connection port 7205, a pointing device 7206, and the like. Note that this computer is fabricated by using light-emitting elements arranged in a matrix in the display portion 7203, which are the same as that described in Embodiment 3. The light-emitting elements each include the compound of one embodiment of the present invention and thus can have high emission efficiency and low driving voltage. Therefore, the computer including the display portion 7203 which is formed using the light-emitting elements can have reduced power consumption and low driving voltage.

Figure 6C:
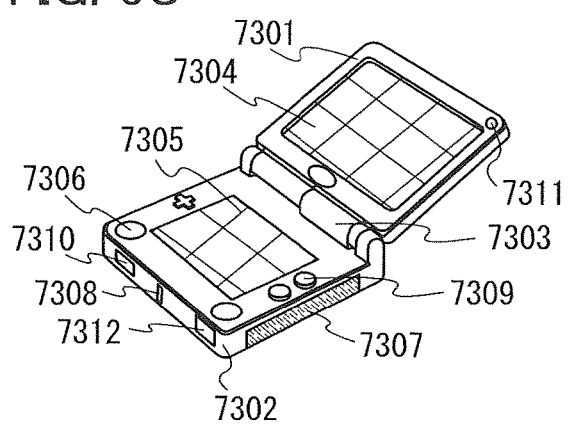

FIG. 6C illustrates a portable game machine having two housings, a housing 7301 and a housing 7302, which are connected with a joint portion 7303 so that the portable game machine can be opened or folded. A display portion 7304 including light-emitting elements which are the same as that described in Embodiment 3 and arranged in a matrix is incorporated in the housing 7301, and a display portion 7305 is incorporated in the housing 7302. In addition, the portable game machine illustrated in FIG. 6C includes a speaker portion 7306, a recording medium insertion portion 7307, an LED lamp 7308, an input unit (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as far as the display portion including light-emitting elements which are the same as that described in Embodiment 3 and arranged in a matrix is used as at least either the display portion 7304 or the display portion 7305, or both, and the structure can include other accessories as appropriate. The portable game machine illustrated in FIG. 6C has a function of reading out a program or data stored in a storage medium to display it on the display portion, and a function of sharing information with another portable game machine by wireless communication. The portable game machine illustrated in FIG. 6C can have a variety of functions without limitation to the above. Since the light-emitting elements used in the display portion 7304 have high emission efficiency by including the compound of one embodiment of the present invention having a structure in which a carbazole skeleton is bonded to a benzofuropyridyl group or a benzothienopyridyl group through an arylene group, the portable game machine including the above-described display portion 7304 can be a portable game machine having reduced power consumption. Since the light-emitting elements used in the display portion 7304 each have low driving voltage by including the compound of one embodiment of the present invention, the portable game machine can also be a portable game machine having low driving voltage.

Figure 6D:
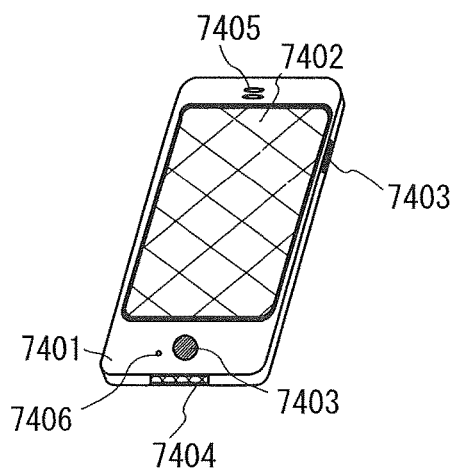

FIG. 6D illustrates an example of a mobile phone. A mobile phone is provided with a display portion 7402 incorporated in a housing 7401, operation buttons 7403, an external connection port 7404, a speaker 7405, a microphone 7406, and the like. Note that the mobile phone has the display portion 7402 including light-emitting elements which are the same as that described in Embodiment 3 and arranged in a matrix. The light-emitting elements each include the compound of one embodiment of the present invention and thus can have high emission efficiency and low driving voltage. Therefore, the mobile phone including the display portion 7402 which is formed using the light-emitting elements can have reduced power consumption and low driving voltage.

When the display portion 7402 of the mobile phone illustrated in FIG. 6D is touched with a finger or the like, data can be input into the mobile phone. In this case, operations such as making a call and creating e-mail can be performed by touching the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are combined.

For example, in the case of making a call or creating e-mail, a character input mode mainly for inputting characters is selected for the display portion 7402 so that characters displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone, display on the screen of the display portion 7402 can be automatically changed by determining the orientation of the cellular phone (whether the cellular phone is placed horizontally or vertically for a landscape mode or a portrait mode).

The screen modes are switched by touch on the display portion 7402 or operation with the operation buttons 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Further, by providing a backlight or a sensing light source which emits near-infrared light in the display portion, an image of a finger vein, a palm vein, or the like can be taken.

Note that the structure described in this embodiment can be combined with any of the structures described in Embodiments 1 to 4 as appropriate.

As described above, the application range of the light-emitting device having the light-emitting element described in Embodiment 3 which includes the compound of one embodiment of the present invention is wide so that this light-emitting device can be applied to electronic devices in a variety of fields. By using the compound, an electronic device having reduced power consumption and low driving voltage can be obtained.

The light-emitting element including the compound of one embodiment of the present invention can also be used for a light source device. One mode is described with reference to FIG. 7. Note that the light source device includes a light-emitting element including the compound of one embodiment of the present invention as a light irradiation unit and at least includes an input-output terminal portion which supplies current to the light-emitting element. Further, the light-emitting element is preferably shielded from the outside atmosphere by sealing.

Figure 7:
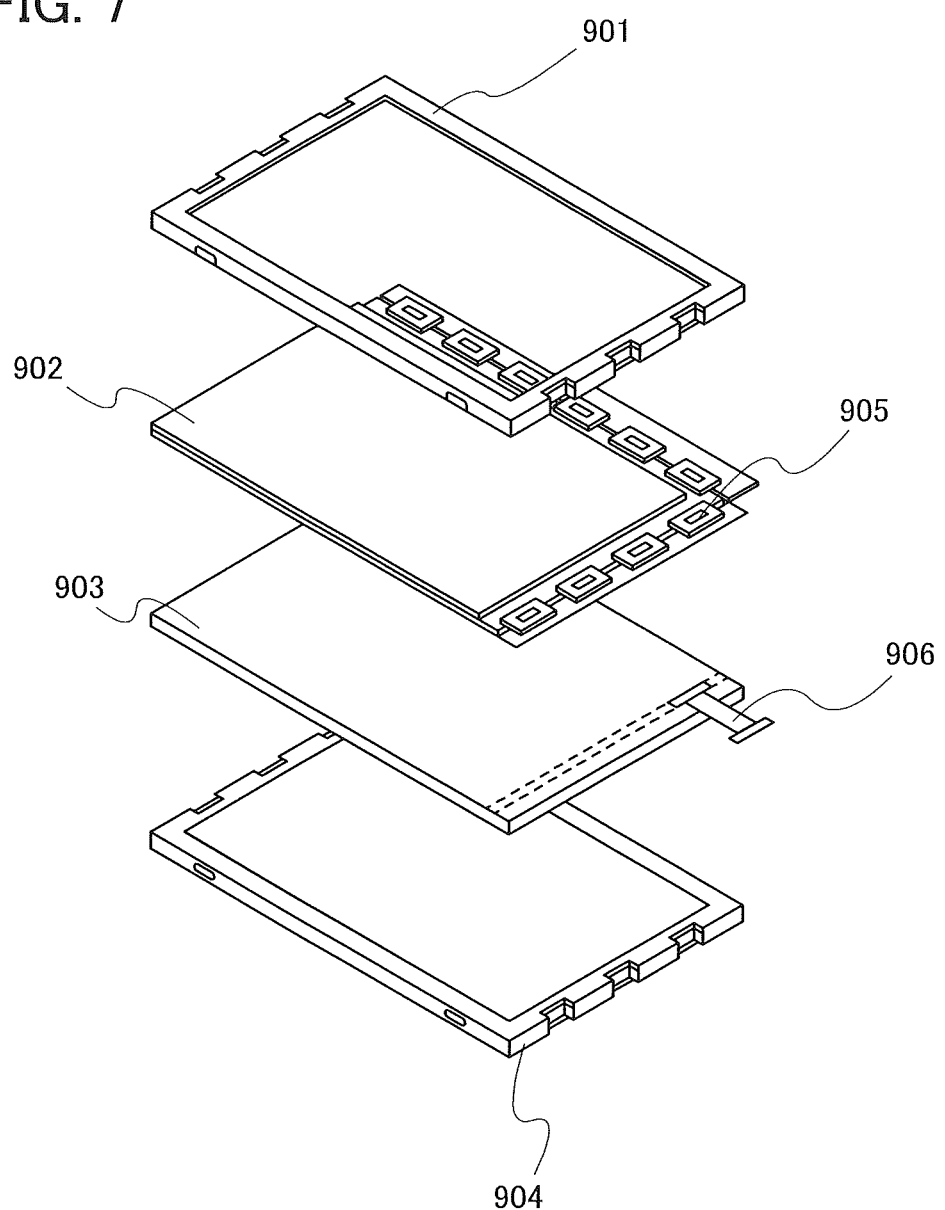
FIG. 7 illustrates a light source device.

FIG. 7 illustrates an example of a liquid crystal display device using the light-emitting elements including the compound of one embodiment of the present invention for a backlight. The liquid crystal display device illustrated in FIG. 7 includes a housing 901, a liquid crystal layer 902, a backlight 903, and a housing 904. The liquid crystal layer 902 is connected to a driver IC 905. The light-emitting element including the above compound is used in the backlight 903, to which current is supplied through a terminal 906.

The light-emitting element including the above compound is used for the backlight of the liquid crystal display device; thus, the backlight can have reduced power consumption. In addition, the use of the light-emitting element including the above compound enables fabrication of a planar-emission lighting device and further a larger-area planar-emission lighting device; therefore, the backlight can be a larger-area backlight, and the liquid crystal display device can also be a larger-area device. Furthermore, with the backlight using the light-emitting element including the above compound, the light-emitting device can be thinner than a conventional one; accordingly, the display device can also be thinner.

Figure 8:
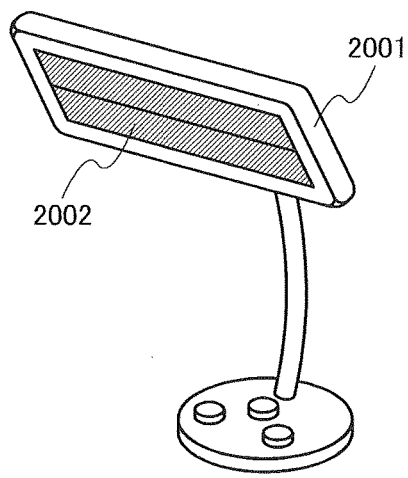
FIG. 8 illustrates a lighting device.

FIG. 8 illustrates an example in which the light-emitting element including the compound of one embodiment of the present invention is used for a table lamp which is a lighting device. The table lamp illustrated in FIG. 8 includes a housing 2001 and a light source 2002, and the light-emitting element including the above heterocyclic compound is used for the light source 2002.

Figure 9:
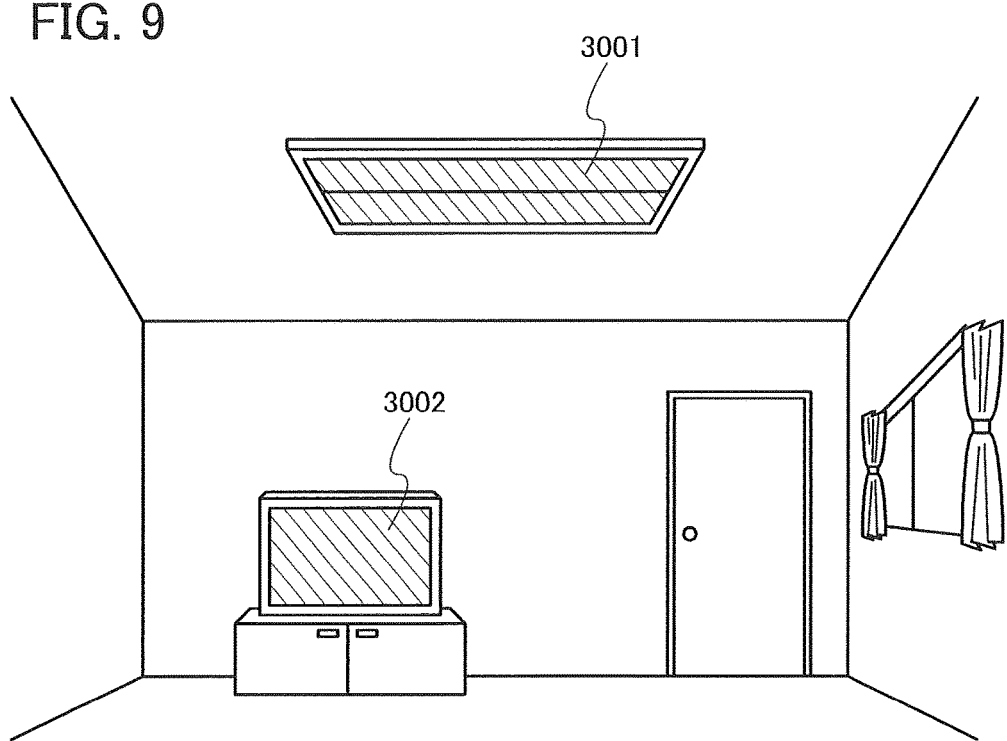
FIG. 9 illustrates a lighting device and an electronic device.

FIG. 9 illustrates an example in which the light-emitting element including the compound of one embodiment of the present invention is used for an indoor lighting device 3001. Since the light-emitting element including the above compound has reduced power consumption, a lighting device that has reduced power consumption can be obtained. Further, since the light-emitting element including the above compound can have a large area, the light-emitting element can be used for a large-area lighting device. Furthermore, since the light-emitting element including the above compound is thin, a lighting device having a reduced thickness can be fabricated. FIG. 9 also illustrates an example in which the light-emitting element including the compound of one embodiment of the present invention is used for a display device 3002.

The light-emitting element including the compound of one embodiment of the present invention can also be used for an automobile windshield or an automobile dashboard. FIG. 10 illustrates one mode in which the light-emitting elements including the above heterocyclic compound are used for an automobile windshield and an automobile dashboard. Display regions 5000 to 5005 each include the light-emitting element including the above heterocyclic compound.

The display regions 5000 and 5001 are display devices which are provided in the automobile windshield and in which light-emitting elements including the above heterocyclic compound are incorporated. The light-emitting element including the above heterocyclic compound can be formed into a so-called see-through display device, through which the opposite side can be seen, by including a first electrode and a second electrode formed of electrodes having light-transmitting properties. Such see-through display devices can be provided even in the windshield of the car, without hindering the vision. Note that in the case where a transistor for driving the light-emitting element is provided, a transistor having a light-transmitting property, such as an organic transistor using an organic semiconductor material or a transistor using an oxide semiconductor, is preferably used.

The display region 5002 is a display device which is provided in a pillar portion and in which the light-emitting element including the above heterocyclic compound is incorporated. The display region 5002 can compensate for the view hindered by the pillar portion by showing an image taken by an imaging unit provided in the car body. Similarly, the display region 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display region 5004 and the display region 5005 can provide a variety of kinds of information such as navigation data, a speedometer, a tachometer, a mileage, a fuel meter, a gearshift indicator, and air-condition setting. The content or layout of the display can be changed freely by a user as appropriate. Note that such information can also be shown by the display regions 5000 to 5003. The display regions 5000 to 5005 can also be used as lighting devices.

By including the compound having a structure in which a carbazole skeleton is bonded to a benzofuropyridyl group or a benzothienopyridyl group through an arylene group, the light-emitting element including the above heterocyclic compound can have low driving voltage and the light-emitting device with lower power consumption can be obtained. Therefore, load on a battery is small even when a number of large screens such as the display regions 5000 to 5005 are provided, which provides comfortable use. For that reason, the light-emitting device and the lighting device each of which includes the light-emitting element including the above heterocyclic compound can be suitably used as an in-vehicle light-emitting device and lighting device.

The compound of one embodiment of the present invention can be used for an electronic device such as an organic thin film solar cell. Specifically, the compound can be used in a carrier-transport layer or a carrier-injection layer since the compound has a carrier-transport property. The compound can be photoexcited and hence can be used in a power generation layer.

Example 1

Synthesis Example 1

In this example, a method for synthesizing 8-[3'-(9H-carbazol-9-yl)biphenyl-3-yl]benzo[4,5]furo[3,2-b]pyridine (abbreviation: mCzBPBfpy) (Structural Formula (112)) that is the compound described in Embodiment 1 having a structure in which a carbazole skeleton is bonded to a benzofuropyridyl group or a benzothienopyridyl group through an arylene group is described. The structural formula of mCzBPBfpy is shown below.

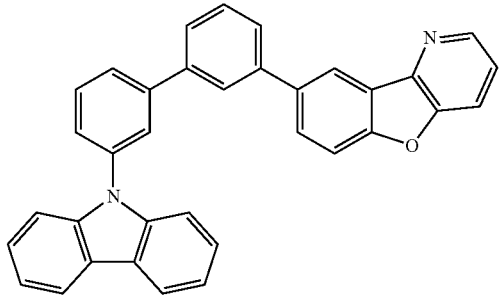

(112)

Synthesis of 8-[3'-(9H-carbazol-9-yl)biphenyl-3-yl]benzo[4,5]furo[3,2-b]pyridine First, 1.6 g (6.4 mmol) of 8-bromobenzo[4,5]furo[3,2-b]pyridine, 2.6 g (7.0 mmol) of 3'-(9H-carbazol-9-yl)-3-biphenylboronic acid, 0.19 g (0.64 mmol) of tri(o-tolyl)phosphine, 1.8 g (13 mmol) of potassium carbonate, 60 mL of toluene, 12 mL of ethanol, and 6.0 mL of water were put into a 200 mL three-neck flask. This mixture was degassed by being stirred under reduced pressure, and the atmosphere in the flask was replaced with nitrogen. To this mixture was added 29 mg (0.13 mmol) of palladium(II) acetate, and stirring was performed under a nitrogen stream at 80° C. for 24 hours. After a certain period of time, water was added to the reaction mixture, and an aqueous layer was subjected to extraction with toluene. The obtained solution of the extract and the organic layer were combined, and washed with water and saturated saline, and then magnesium sulfate was added to the organic layer so that moisture was adsorbed. This mixture was subjected to gravity filtration, and the filtrate was concentrated to give a brown solid. The obtained solid was purified by silica gel column chromatography (toluene) to give a white powder. This powder was recrystallized with a mixed solvent of ethyl acetate and hexane to give 2.0 g of a white powder of the target substance in a yield of 64%. The synthesis scheme of this step is shown in Formula (B-1).

Scheme (B-1)

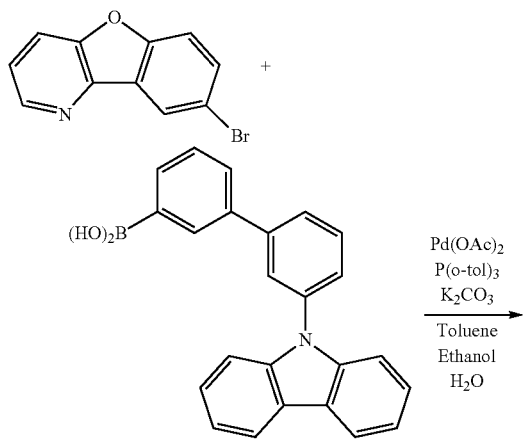

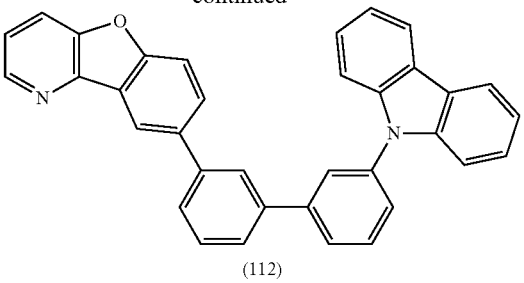

(112)

By a train sublimation method, 2.0 g of the obtained white powder of 8-[3'-(9H-carbazol-9-yl)biphenyl-3-yl]benzo[4,5]furo[3,2-b]pyridine was purified. In the purification by sublimation, mCzBPBfpy was heated at 280° C. under a pressure of 2.4 Pa with a flow rate of argon gas of 5 mL/min. Through the purification by sublimation, 1.6 g of a white powder of mCzBPBfpy was obtained at a collection rate of 80%.

The obtained white powder was purified by high-performance liquid column chromatography (HPLC). The obtained fraction was concentrated to give a white powder.

By a train sublimation method, 1.6 g of the obtained white powder of mCzBPBfpy was purified. The purification by sublimation was conducted by heating at 260° C. under a pressure of 3.0 Pa with a flow rate of argon gas of 5 mL/min to give 1.2 g of a white powder of mCzBPBfpy at a collection rate of 75%.

The obtained compound was subjected to nuclear magnetic resonance spectrometry ($^1$H NMR), and the results are shown below. The results revealed that mCzBPBfpy was obtained.

$^1$H NMR (CDCl$_3$, 300 MHz): δ=8.66 (dd, J=1.5 Hz, 4.5 Hz, 1H), 8.53 (d, J=1.5 Hz, 1H), 8.17 (d, J=7.5 Hz, 2H), 7.97-7.98 (m, 1H), 7.85-7.89 (m, 3H), 7.78-7.82 (m, 1H), 7.65-7.75 (m, 4H), 7.58-7.61 (m, 2H), 7.39-7.51 (m, 5H), 7.26-7.33 (m, 2H).

Figure 11A:
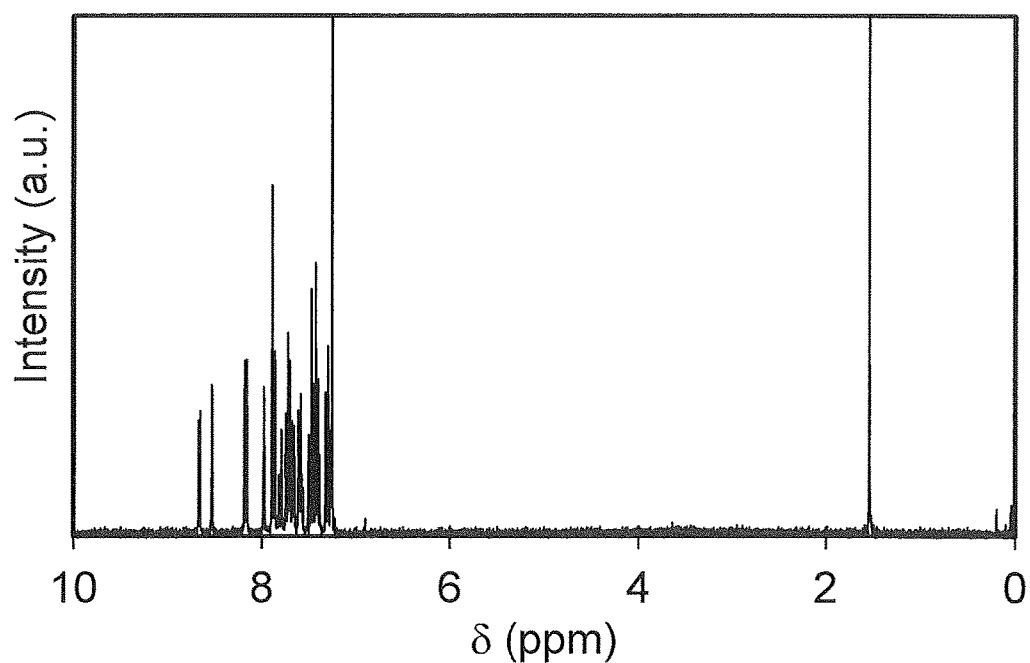
FIGS. 11A and 11B are NMR charts of mCzBPBfpy.
Figure 11B:
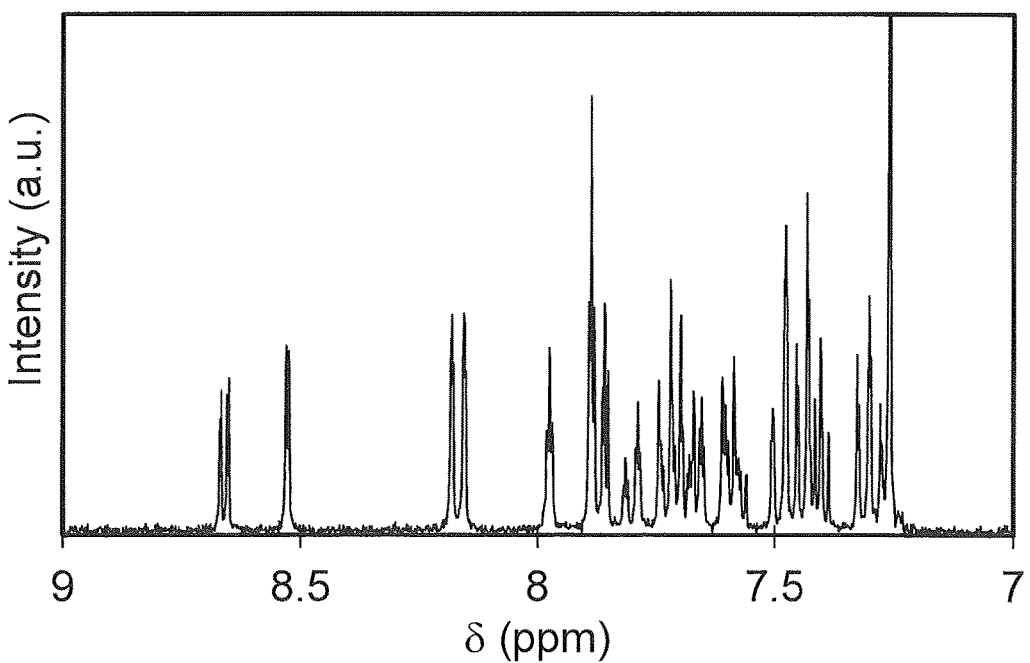

FIGS. 11A and 11B are $^1$H NMR charts. Note that FIG. 11B is a chart showing an enlarged part in the range of 7 ppm to 9 ppm of FIG. 11A. The results revealed that mCzBPBfpy was obtained.

The obtained compound was analyzed by LC/MS.

In the LC/MS analysis, liquid chromatography (LC) separation was carried out with ACQUITY UPLC (manufactured by Waters Corporation) and mass spectrometry (MS) analysis was carried out with Xevo G2 Tof MS (manufactured by Waters Corporation). ACQUITY UPLC BEH C8 (2.1×100 mm, 1.7 μm) was used as a column for the LC separation, and the column temperature was 40° C. Acetonitrile was used for Mobile Phase A and a 0.1% formic acid aqueous solution was used for Mobile Phase B. Furthermore, a sample was prepared in such a manner that mCzBPBfpy was dissolved in toluene at a given concentration and the solution was diluted with acetonitrile. The injection amount was 5.0 μL.

In the LC separation, a gradient method in which the composition of mobile phases is changed was employed. The ratio of Mobile Phase A to Mobile Phase B was kept to be 60:40 for 0 to 1 minute after the start of the measurement, and then the composition gradient was generated such that the ratio of Mobile Phase A to Mobile Phase B after 10 minutes from the start of the measurement was 95:5. The composition has a linear gradient.

In the MS analysis, ionization was carried out by an electrospray ionization (ESI) method. At this time, the capillary voltage and the sample cone voltage were set to 3.0 kV and 30 V, respectively, and detection was performed in a positive mode. A component which underwent the ionization under the above-described conditions was collided with an argon gas in a collision cell to dissociate into product ions. Energy (collision energy) for the collision with argon was 70 eV. The mass range for the measurement was m/z=100 to 1200. The detection results of the dissociated product ions by time-of-flight (TOF) MS are shown in FIG. 20.

Figure 20:
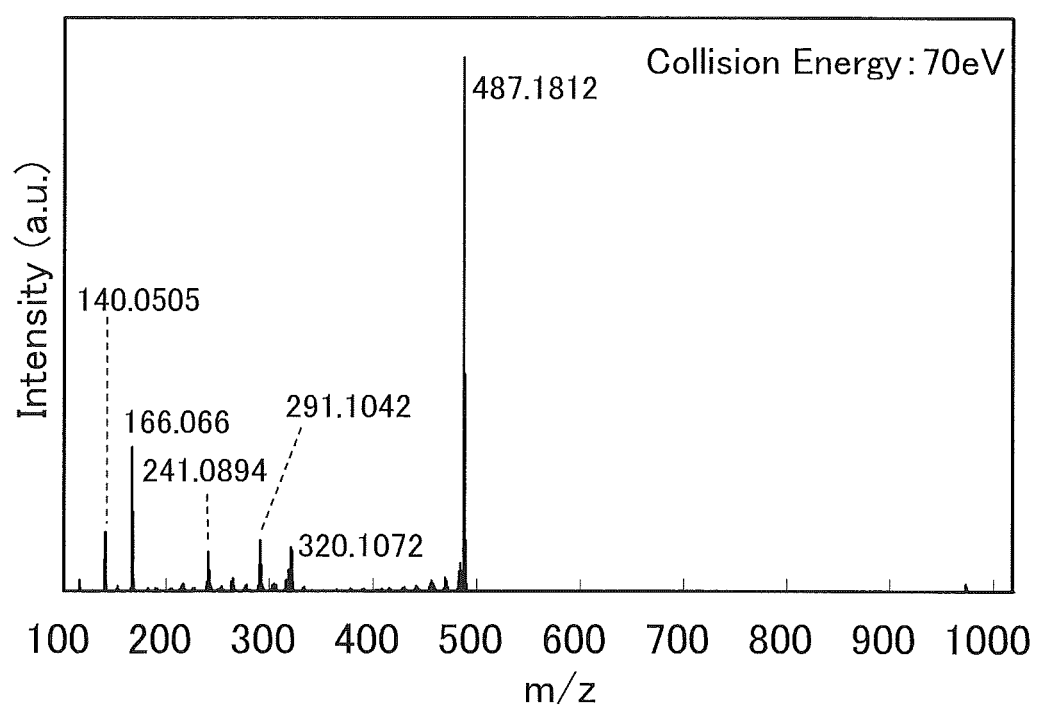
FIG. 20 shows an MS spectrum of mCzBPBfpy.

It was found from the result of FIG. 20 that product ions of mCzBPBfpy were detected mainly around m/z=320, 241, 166. Note that the result in FIG. 20 shows characteristics derived from mCzBPBfpy and therefore can be regarded as important data for identifying mCzBPBfpy contained in a mixture.

The product ion around m/z=320 is presumed to be a cation expressed as $C_{23}H_{14}NO^+$ in the state where carbazole is dissociated from mCzBPBfpy. The product ion around m/z=241 is presumed to be a radical cation expressed as $C_{18}H_{11}N^+$ of 9-phenyl carbazole in mCzBPBfpy. The product ion around m/z=166 is presumed to be a cation expressed as $C_{12}H_8N^+$ of carbazole in mCzBPBfpy. These indicate that mCzBPBfpy includes a carbazole skeleton and a benzene skeleton. Note that there is a possibility that the above m/z values±1 are detected as protonation or deprotonation products of the product ions.

Physical Properties of mCzBPBfpy

Figure 12:
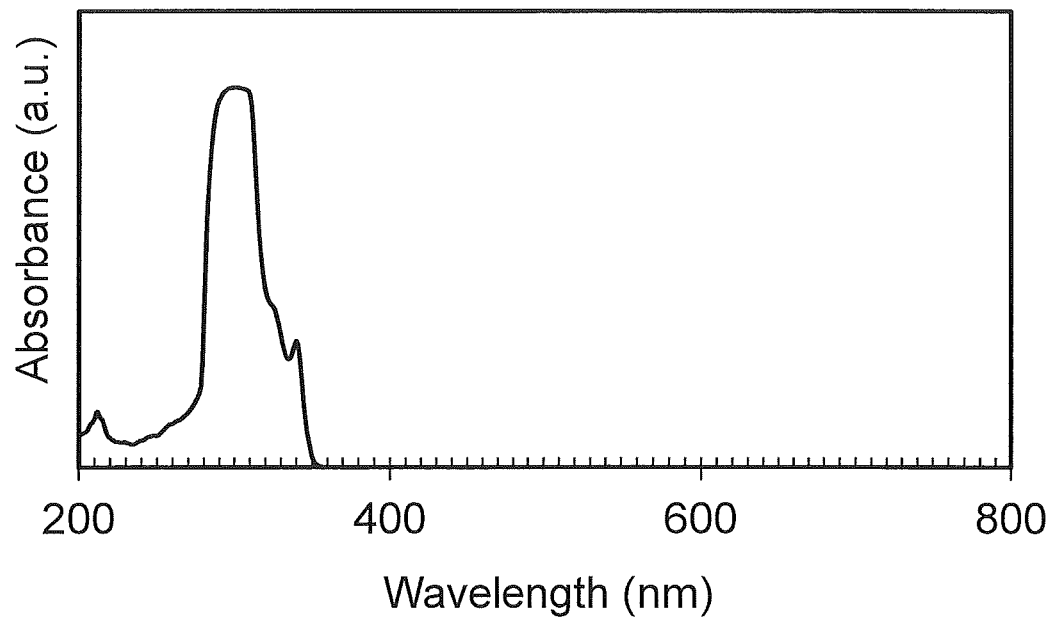
FIG. 12 shows an absorption spectrum of a solution of mCzBPBfpy.
Figure 13:
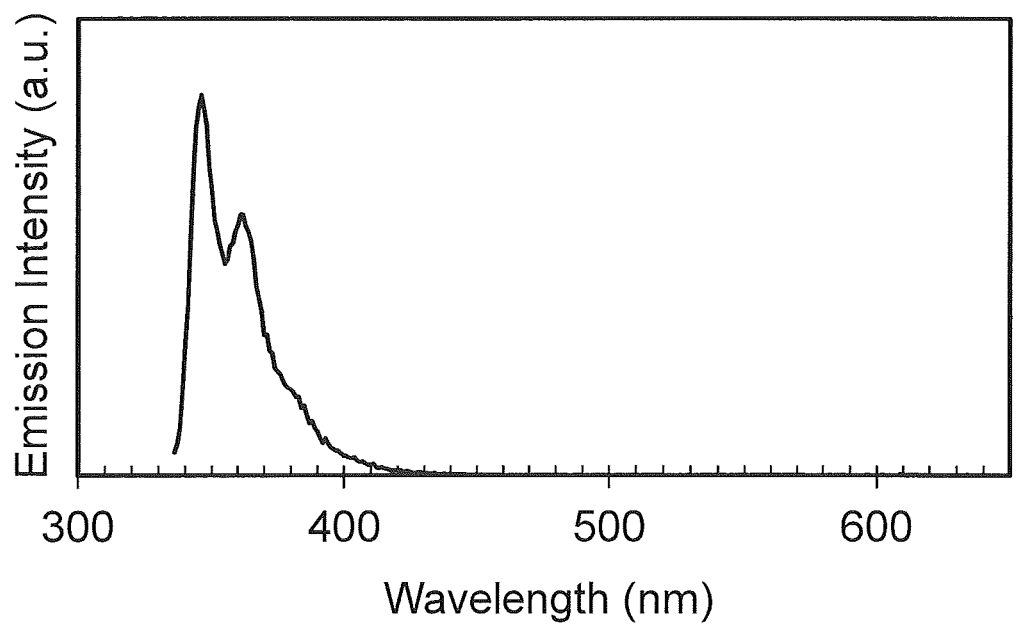
FIG. 13 shows an emission spectrum of a solution of mCzBPBfpy.
Figure 14:
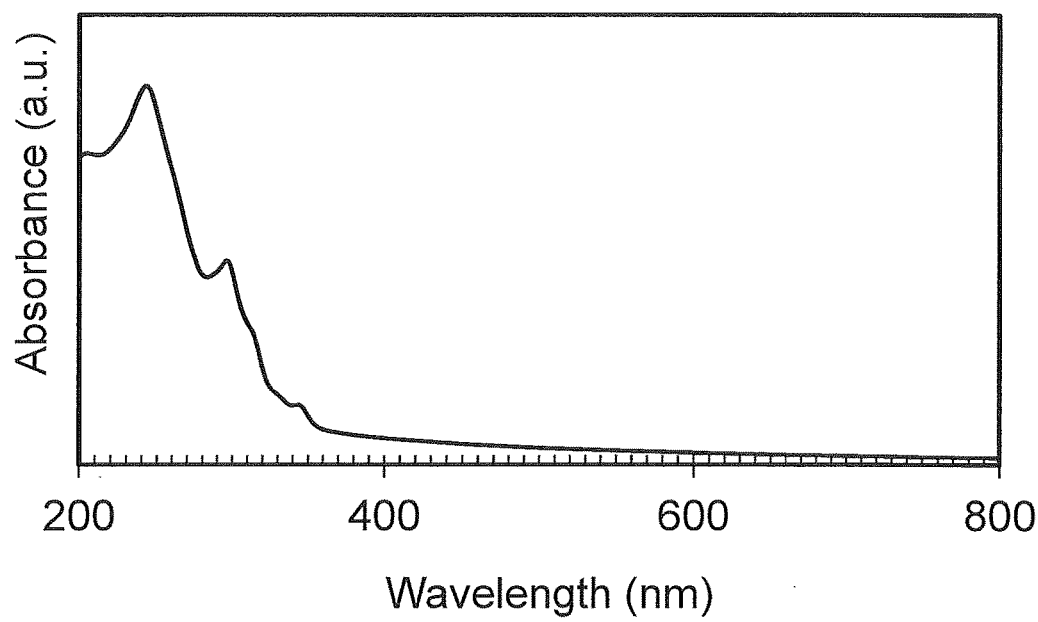
FIG. 14 shows an absorption spectrum of a thin film of mCzBPBfpy.
Figure 15:
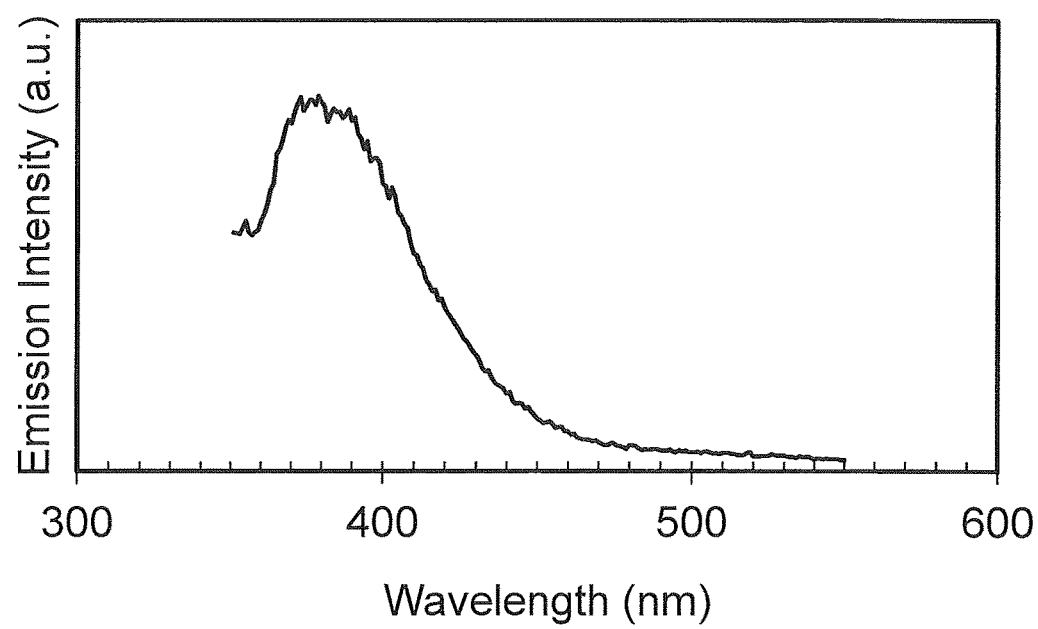
FIG. 15 shows an emission spectrum of a thin film of mCzBPBfpy.

FIG. 12 shows an absorption spectrum of a toluene solution of mCzBPBfpy, and FIG. 13 shows an emission spectrum thereof. FIG. 14 shows an absorption spectrum of a thin film of mCzBPBfpy, and FIG. 15 shows an emission spectrum thereof. The absorption spectra were measured with an ultraviolet-visible spectrophotometer (V-550, produced by JASCO Corporation). The emission spectra were measured with a fluorescence spectrophotometer (FS920, produced by Hamamatsu Photonics K.K.). The spectrum of mCzBPBfpy in the toluene solution was measured with a toluene solution of mCzBPBfpy put in a quartz cell. The spectrum of the thin film was measured with a sample prepared by deposition of mCzBPBfpy on a quartz substrate by evaporation. Note that the absorption spectrum of mCzBPBfpy in the toluene solution shown in the drawing was obtained by subtraction of the absorption spectrum of quartz and toluene from the measured spectrum, and the absorption spectrum of the thin film of mCzBPBfpy shown in the drawing was obtained by subtraction of the absorption spectrum of the quartz substrate from the measured spectrum.

As observed in FIG. 12 and FIG. 13, absorption peaks of mCzBPBfpy in the toluene solution are at approximately 212 nm, 300 nm, 327 nm, and 340 nm, and emission wavelength peaks thereof are at 346 nm, 361 nm, and 383 nm (excitation wavelength: 327 nm). As observed in FIG. 14 and FIG. 15, absorption peaks of the thin film of mCzBPBfpy are at approximately 206 nm, 243 nm, 267 nm, 296 nm, 314 nm, and 345 nm, and emission wavelength peaks thereof are at 355 nm and 379 nm (excitation wavelength: 345 nm). It was found that mCzBPBfpy emitted violet light. Therefore, the compound of one embodiment of the present invention can be used as a host material for a light-emitting substance or a host material for a substance emitting phosphorescence in the visible region.

The characteristics of oxidation-reduction reaction were examined by cyclic voltammetry (CV) measurement. An electrochemical analyzer (ALS model 600A or 600C, produced by BAS Inc.) was used for the measurement. The solution for the measurement was prepared by dissolving a supporting electrolyte of tetra-n-butylammonium perchlorate (n-Bu$_4$NClO$_4$) in a solvent of dehydrated dimethylformamide (DMF) such that the concentration became 100 mmol/L, and by further dissolving the measurement object such that the concentration became 2 mmol/L. In addition, a platinum electrode (PTE platinum electrode, produced by BAS Inc.) was used as a working electrode, a platinum electrode (Pt counter electrode for VC-3, (5 cm), produced by BAS Inc.) was used as an auxiliary electrode, and an Ag/Ag$^+$ electrode (RE-7 reference electrode for nonaqueous solvent, produced by BAS Inc.) was used as a reference electrode. The scan rate was set to 0.1 V/sec in all the measurement. According to the measurement results, the oxidation potential was −5.89 eV and the reduction potential was −2.47 eV. When the oxidation potential was regarded as a HOMO level and the reduction potential was regarded as a LUMO level, a gap between the HOMO level and the LUMO level was estimated to be 3.43 eV. The energy value of the first peak on the short wavelength side of the emission spectrum caused by photoexcitation was 3.49 eV, which was close to the estimated value; thus, a structural change due to excitation by carrier injection was expected to be small. Therefore, a light-emitting element can achieve a low driving voltage by using mCzBPBfpy in its light-emitting layer.

The phosphorescence spectrum of mCzBPBfpy was measured. A sample for the measurement was fabricated in such a manner that a thin film of mCzBPBfpy with a thickness of approximately 50 nm was formed over a quartz substrate, and sealed with another quartz substrate in a nitrogen atmosphere. The measurement was performed by using a PL microscope, LabRAM HR-PL (produced by HORIBA, Ltd.), a He—Cd laser (325 nm) as excitation light, and a CCD detector at a measurement temperature of 10 K. Utilizing the fact that the emission lifetime of phosphorescence is longer than that of fluorescence, the phosphorescence spectrum was measured by time-resolved measurement using a mechanical shutter. The first peak of this phosphorescence on the short wavelength side was 448 nm (2.77 eV), and this value was regarded as the T1 level. Therefore, mCzBPBfpy has a high T1 level and is suitable as a host material for an emission center substance emitting blue phosphorescence.

Example 2

In this example, a light-emitting element (a light-emitting element 1) is described. In the light-emitting element 1, 8-[3'-(9H-carbazol-9-yl)biphenyl-3-yl]benzo[4,5]furo[3,2-b]pyridine (abbreviation: mCzBPBfpy) that is the compound described in Embodiment 1 having a structure in which a carbazole skeleton is bonded to a benzofuropyridyl group or a benzothienopyridyl group through an arylene group, is used as a host material in a light-emitting layer that includes an emission center substance emitting blue phosphorescence.

The molecular structures of compounds used in this example are shown in Structural Formulae (i) to (v) and (112) below. The element structure in FIG. 1A was employed.

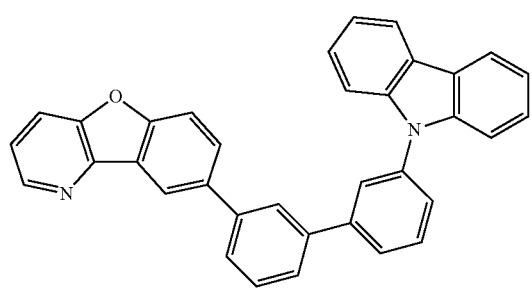

mCzBPBfpy

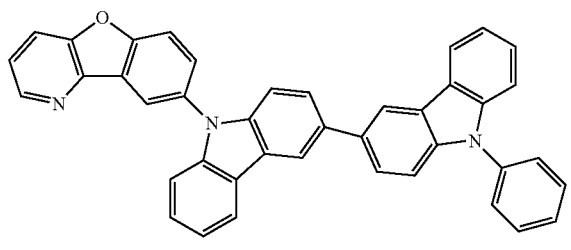

PCCzBfpy

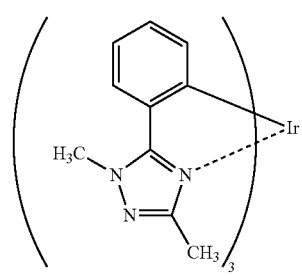

Ir(Mptz1-Me)₃

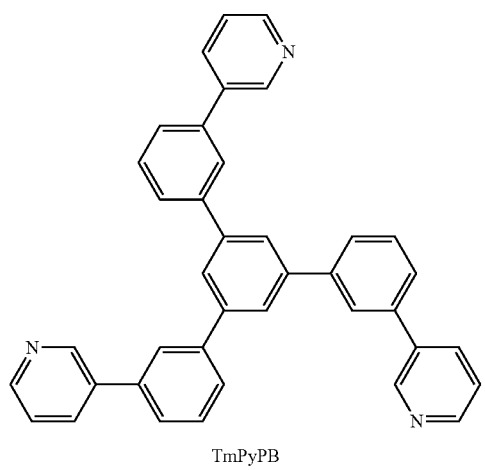

TmPyPB

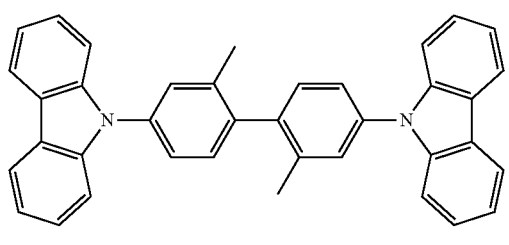

dmCBP

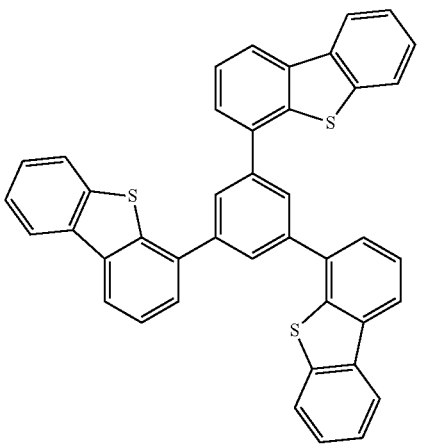

DBT3P-II

Fabrication of Light-Emitting Element 1

First, a glass substrate, over which a film of indium tin oxide containing silicon (ITSO) was formed to a thickness of 70 nm as the first electrode 101, was prepared. A surface of the ITSO was covered with a polyimide film so that an area of 2 mm×2 mm of the surface was exposed. The electrode area was 2 mm×2 mm. As pretreatment for forming the light-emitting element over the substrate, the surface of the substrate was washed with water and baked at 200° C. for 1 hour, and then a UV ozone treatment was performed for 370 seconds. Then, the substrate was transferred into a vacuum evaporation apparatus where the pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed to a holder provided in the vacuum evaporation apparatus such that the surface of the substrate over which the first electrode 101 was formed faced downward. In this example, a case is described in which the hole-injection layer 111, the hole-transport layer 112, the light-emitting layer 113, the electron-transport layer 114, and the electron-injection layer 115, which were included in the EL layer 103, were sequentially formed by a vacuum evaporation method.

After reducing the pressure in the vacuum evaporation apparatus to $10^{-1}$ Pa, 4,4',4"-(benzene-1,3,5-triyl)tri(dibenzothiophene) (abbreviation: DBT3P-II) and molybdenum oxide were deposited by co-evaporation such that the mass ratio of DBT3P-II to molybdenum oxide was 2:1, whereby the hole-injection layer 111 was formed over the first electrode 101. The thickness was set to 20 nm. Note that a co-evaporation method is an evaporation method in which a plurality of different substances is concurrently vaporized from respective different evaporation sources.

Next, 4,4'-bis(9H-carbazol-9-yl)-2,2'-dimethylbiphenyl (abbreviation: dmCBP) was deposited by evaporation to a thickness of 20 nm, whereby the hole-transport layer 112 was formed.

Next, the light-emitting layer 113 was formed over the hole-transport layer 112.

The light-emitting layer 113 was formed in the following manner: 8-[3'-(9H-carbazol-9-yl)biphenyl-3-yl]benzo[4,5]furo[3,2-b]pyridine (abbreviation: mCzBPBfpy) (Structural Formula (112)) and tris(1,3-dimethyl-5-phenyl-1H-1,2,4-triazolato)iridium(III) (abbreviation: [Ir(Mptz1-Me)$_3$]) were deposited by co-evaporation to a thickness of 30 nm such that the mass ratio of mCzBPBfpy to [Ir(Mptz1-Me)$_3$] was 1:0.06.

Next, 1,3,5-tri[3-(3-pyridyl)phenyl]benzene (abbreviation: TinPyPB) was deposited by evaporation to a thickness of approximately 25 nm, whereby the electron-transport layer 114 was formed over the light-emitting layer 113.

Next, lithium fluoride was deposited by evaporation to a thickness of 1 nm over the electron-transport layer 114, whereby the electron-injection layer 115 was formed.

Finally, aluminum was deposited by evaporation to a thickness of 200 nm over the electron-injection layer 115 to form the second electrode 102 serving as a cathode; thus, the light-emitting element 1 was obtained. It is to be noted that an evaporation method using resistive heating was employed for all the evaporation steps.

Table 1 shows an element structure of the light-emitting element 1 obtained in the above manner.

Thus, the comparative light-emitting element 1 was completed. Note that the difference between the comparative light-emitting element 1 and the light-emitting element 1 was only the material of the light-emitting layer. In the comparative light-emitting element 1, PCCzBfpy was used instead of mCzBPBfpy having a structure in which a carbazole skeleton is bonded to a benzofuropyridyl group through an arylene group. Note that PCCzBfpy has a structure in which a carbazole skeleton is directly bonded to a benzofuropyridyl group not through an arylene group, and a carbazolyl group is bonded to the 3-position of the carbazole skeleton.

Operation Characteristics of Light-Emitting Element 1 and Comparative Light-Emitting Element 1

Operation characteristics of the light-emitting element 1 and the comparative light-emitting element 1 obtained as

TABLE 1

| | First electrode 101 | Hole-injection layer 111 | Hole-transport layer 112 | Light-emitting layer 113 | Electron-transport layer 114 | Electron-injection layer 115 | Second electrode 102 |
|---|---|---|---|---|---|---|---|
| Element 1 | ITSO (70 nm) | DBT3P-II:MoOx (2:1 20 nm) | dmCBP (20 nm) | *1 | TmPyPB (25 nm) | LiF (1 nm) | Al (200 nm) |

*1 mCzBPBfpy:[Ir(Mptz1-Me)$_3$] (1:0.06, 30 nm)

The light-emitting element 1 fabricated was sealed in a glove box under a nitrogen atmosphere so as not to be exposed to the air (specifically, a sealant was applied to surround the element, and at the time of sealing, first, UV treatment was performed and then heat treatment was performed at 80° C. for 1 hour).

Fabrication of Comparative Light-Emitting Element 1

A comparative light-emitting element 1 was fabricated in the same trimmer as the light-emitting element 1 except for the light-emitting layer. The light-emitting layer in the comparative light-emitting element 1 was formed in the following manner: 8-[3-(N-phenyl-9H-carbazol-3-yl)-9H-carbazol-9-yl]benzo[4,5]furo[3,2-b]pyridine (abbreviation: PCCzBfpy) (Structural Formula (v)) and tris(1,3-dimethyl-5-phenyl-1H-1,2,4-triazolato)iridium(III) (abbreviation: [Ir(Mptz1-Me)$_3$]) were deposited by co-evaporation to a thickness of 30 nm such that the mass ratio of PCCzBfpy to [Ir(Mptz1-Me)$_3$] was 1:0.06.

The structure except for the light-emitting layer is the same as that of the light-emitting element 1, and repetition of the description thereof is omitted. Refer to the fabrication method of the light-emitting element 1.

described above were examined. Note that the measurement was performed at room temperature (in an atmosphere kept at 25° C.).

Figure 17:
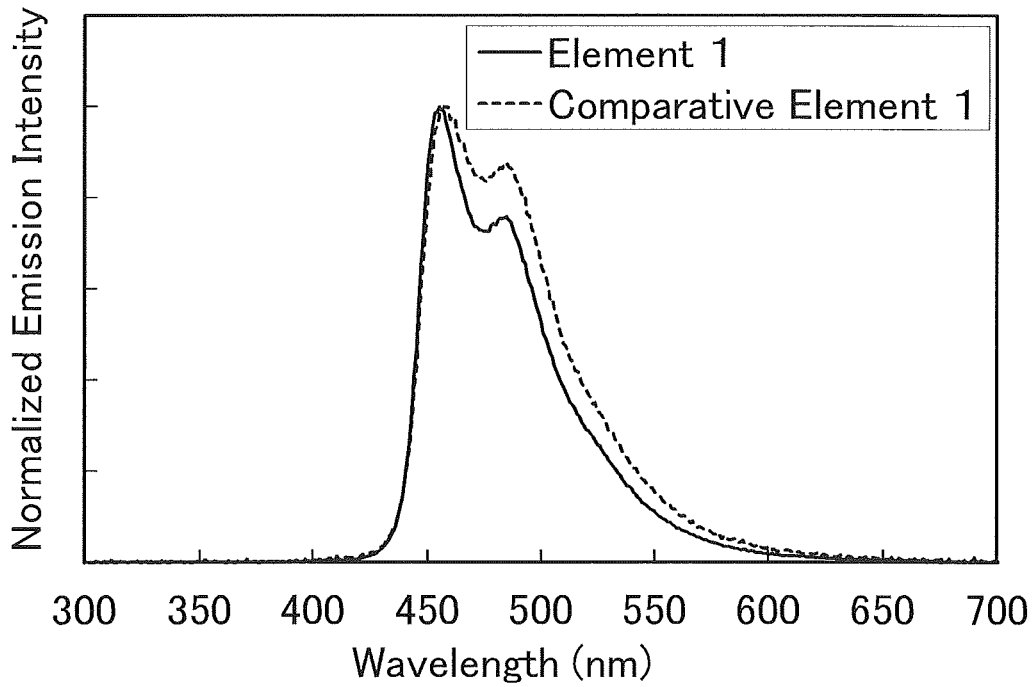
FIG. 17 shows normalized emission spectra of a light-emitting element 1 and a comparative light-emitting element 1.
Figure 18:
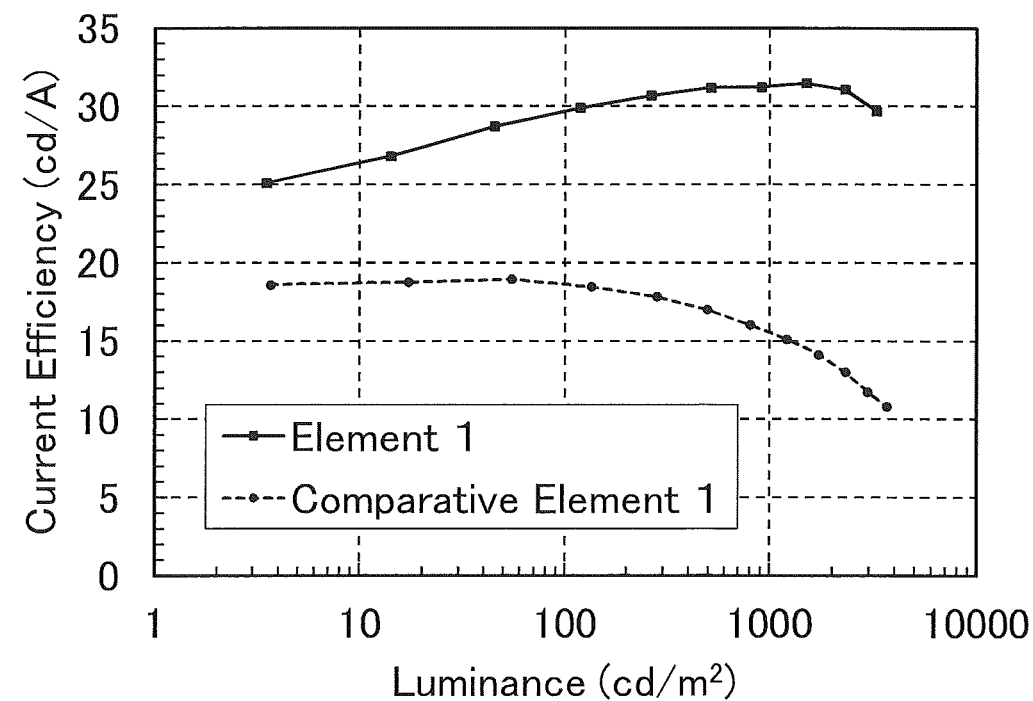
FIG. 18 shows luminance-current efficiency characteristics of the light-emitting element 1 and the comparative light-emitting element 1.
Figure 19:
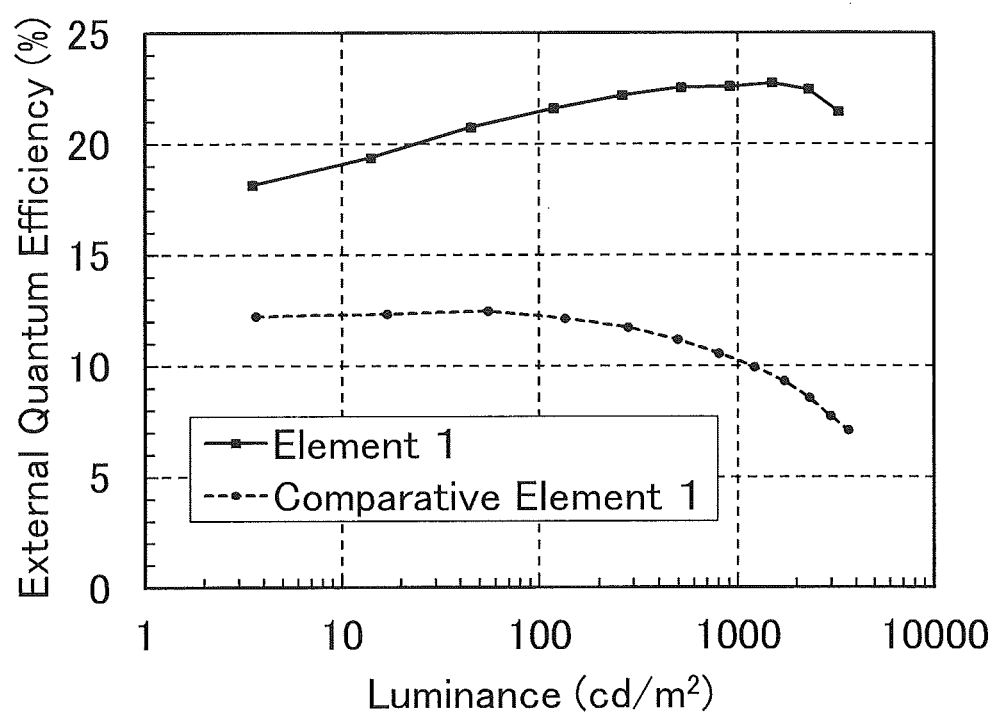
FIG. 19 shows luminance-external quantum efficiency characteristics of the light-emitting element 1 and the comparative light-emitting element 1.

FIG. 17 shows normalized emission spectra of the light-emitting element 1 and the comparative light-emitting element 1, FIG. 18 shows luminance-current efficiency characteristics thereof, and FIG. 19 shows luminance-external quantum efficiency characteristics thereof. Table 2 shows characteristics of the light-emitting element 1 and the comparative light-emitting element 1.

TABLE 2

| | Voltage (V) | Current (mA) | Current density (mA/cm$^2$) | Chromaticity (x, y) | Luminance (cd/m$^2$) | Current efficiency (cd/A) | Power efficiency (lm/W) |
|---|---|---|---|---|---|---|---|
| Element 1 | 4.8 | 0.12 | 2.91 | (0.15, 0.18) | 910 | 31.2 | 20.5 |
| Comparative Element 1 | 4.6 | 0.2 | 4.99 | (0.15, 0.21) | 801 | 16.1 | 11.0 |

According to these results, the light-emitting element 1 that includes the compound of one embodiment of the present invention having a structure in which a carbazole skeleton is bonded to a benzofuropyridyl group through an arylene group has significantly improved current efficiency and external quantum efficiency compared with the comparative light-emitting element 1. This is probably because mCzBPBfpy of one embodiment of the present invention has a higher T1 level and can make a dopant [Ir(Mptz1-Me)$_3$] emit light more efficiently than PCCzBfpy used in the comparative light-emitting element 1 does. Therefore, mCzBPBfpy of one embodiment of the present invention can preferably be used as a host material for a material emitting blue phosphorescence. Note that the T1 level of PCCzBfpy was estimated to be 2.65 eV (468 nm) by the same measurement method as that in Example 1.

Example 3

Synthesis Example 2

In this example, a method for synthesizing 6-[3'-(9H-carbazol-9-yl)biphenyl-3-yl]benzo[4,5]furo[3,2-b]pyridin (abbreviation: mCzBPBfpy-02) (Structural Formula (122)) that is the compound described in Embodiment 1 having a structure in which a carbazole skeleton is bonded to a benzofuropyridyl group or a benzothienopyridyl group through an arylene group is described. The structural formula of mCzBPBfpy-02 is shown below.

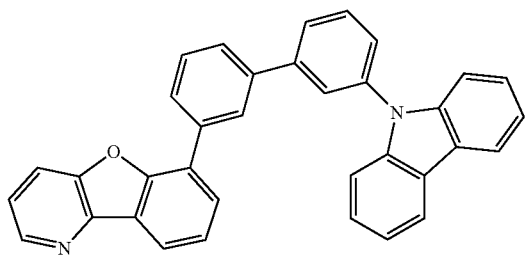

(122)

Synthesis of 6-methoxybenzo[4,5]furo[3,2-b]pyridine

Into a 500 mL three-neck flask were put 4.7 g (27 mmol) of 2-bromo-3-hydroxypyridine, 5.0 g (29 mmol) of 2-fluoro-3-methoxyphenylboronic acid, and 15 g (110 mmol) of potassium carbonate, and the atmosphere in the flask was replaced with nitrogen. To this mixture was added 250 mL of dimethylacetamide, and the mixture was degassed by being stirred under reduced pressure. To this mixture was added 0.62 g (0.53 mmol) of tetrakis(triphenylphosphine)palladium(0), and stirring was performed under a nitrogen stream at 90° C. for 44 hours. After a certain period of time, stirring was performed at 160° C. for 30 hours. After a certain period of time, water was added to the reaction mixture, and an aqueous layer was subjected to extraction with toluene. The obtained solution of the extract and the organic layer were combined, and washed with water and saturated saline, and then magnesium sulfate was added to the organic layer so that moisture was adsorbed. This mixture was subjected to gravity filtration, and the filtrate was concentrated to give a black liquid. This liquid was purified by silica gel column chromatography (toluene:ethyl acetate=9:1) to give 1.7 g of a white solid in a yield of 32%. The synthesis scheme of this step is shown in Formula (C-1).

Scheme (C-1)

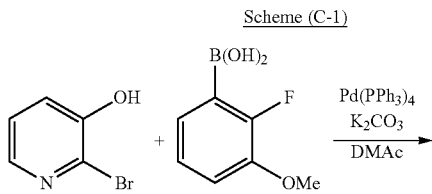

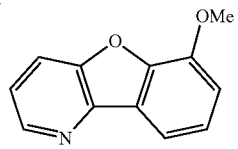

The obtained compound was subjected to nuclear magnetic resonance spectrometry ($^1$H NMR), and the results are shown below. The results revealed that 6-methoxybenzo[4,5]furo[3,2-b]pyridine was obtained.

$^1$H NMR (CDCl$_3$, 300 MHz): δ=8.65 (dd, J=1.5 Hz, 4.9 Hz, 1H), 7.89 (dd, J=1.5 Hz, 8.8 Hz, 1H), 7.83 (dd, J=1.0 Hz, 7.8 Hz, 1H), 7.35-7.41 (m, 2H), 7.11 (d, J=7.3 Hz, 1H), 4.09 (s, 3H).

Figure 21A:
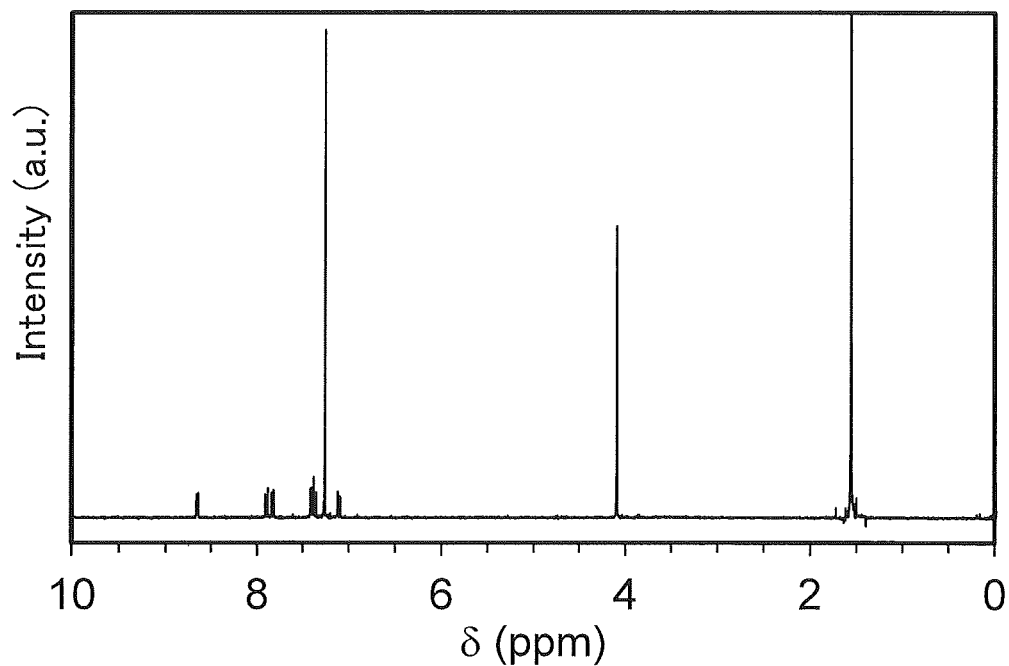
FIGS. 21A and 21B are NMR charts of 6-methoxybenzo[4,5]furo[3,2-b]pyridine.
Figure 21B:
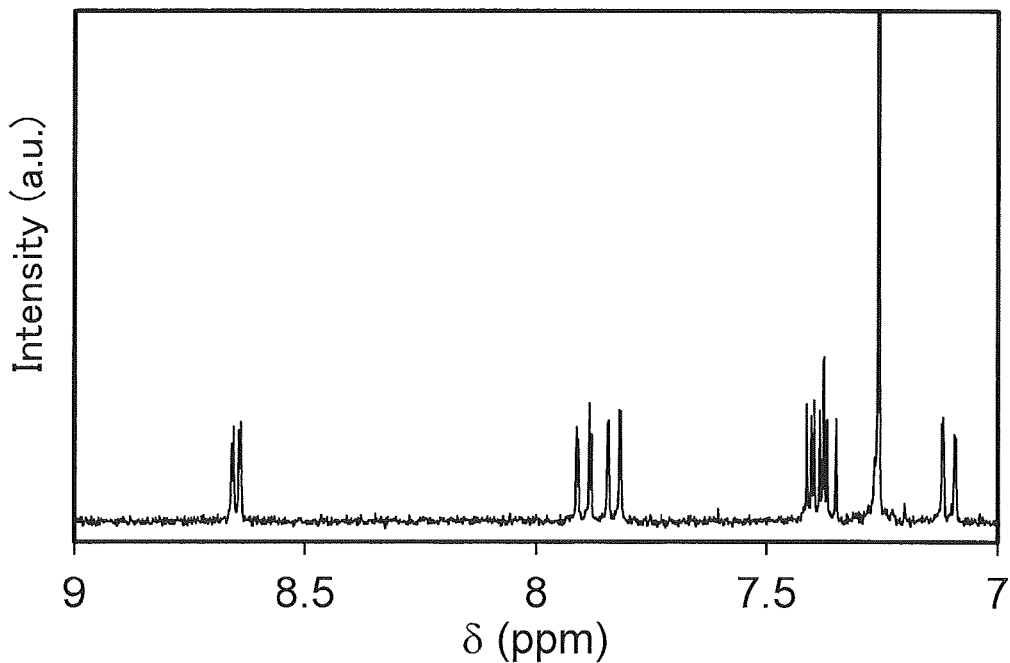

FIGS. 21A and 21B are $^1$H NMR charts. Note that FIG. 21B is a chart showing an enlarged part in the range of 7 ppm to 9 ppm of FIG. 21A. The results revealed that the target substance, 6-methoxybenzo[4,5]furo[3,2-b]pyridine was obtained.

Synthesis of benzo[4,5]furo[3,2-b]pyridin-6-yl 1,1,1-trifluoromethanesulfonate

Into a 200 mL three-neck flask was put 1.7 g (8.4 mmol) of 6-methoxybenzo[4,5]furo[3,2-b]pyridine, and the atmosphere in the flask was replaced with nitrogen. To this mixture was added 60 mL of dehydrated dichloromethane, and the mixture was cooled down to 0° C. To this mixture was dropped 17 mL of boron tribromide (a 1M dichloromethane solution), and stirring was performed at room temperature for 24 hours. After a certain period of time, water was added to the reaction mixture, and an aqueous layer was subjected to extraction with dichloromethane. The obtained solution of the extract and the organic layer were combined and washed with a saturated aqueous solution of sodium hydrogen carbonate, water, and saturated saline, and the organic layer was dried over magnesium sulfate. This mixture was subjected to gravity filtration, and the filtrate was concentrated to give 2.2 g of a yellow solid of 6-hydroxybenzo[4, 5]furo[3,2-b]pyridine.

The obtained solid was put into a 200 mL three-neck flask, and the atmosphere in the flask was replaced with nitrogen. Into this flask were put 84 mL of dehydrated dichloromethane and 2.7 mL of pyridine, and the mixture was cooled down to 0° C. After the cooling, a solution obtained by adding 2.8 mL (17 mmol) of trifluoromethanesulfonic anhydride into 8 mL of dehydrated dichloromethane was dropped, the temperature of this solution was raised to room temperature, and stirring was performed for 20 hours. After a certain period of time, water and a saturated aqueous solution of sodium hydrogen carbonate were added to the reaction mixture, and an aqueous layer was subjected to extraction with dichloromethane. The obtained solution of the extract and the organic layer were combined, and washed with a saturated aqueous solution of sodium hydrogen carbonate, water, and saturated saline, and then magnesium sulfate was added to the organic layer so that moisture was adsorbed. This mixture was subjected to gravity filtration, and the filtrate was concentrated to give a brown solid. This solid was purified by silica gel column chromatography (chloroform) to give 1.2 g of a white solid in a yield of 46%. The synthesis scheme of this step is shown in Formula (C-2).

Scheme (C-2)

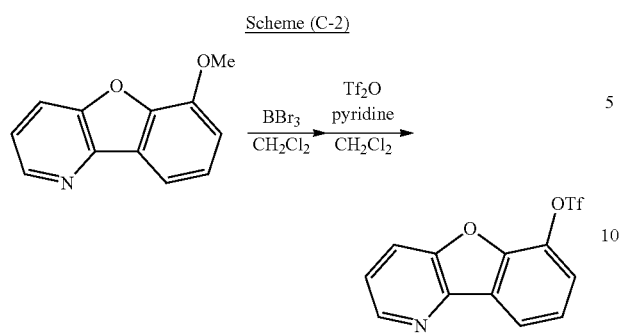

The obtained compound was subjected to nuclear magnetic resonance spectrometry ($^1$H NMR), and the results are shown below. The results revealed that benzo[4,5]furo[3,2-b]pyridin-6-yl 1,1,1-trifluoromethanesulfonate was obtained.

$^1$H-NMR (CDCl$_3$, 300 MHz): δ=8.72 (dd, J=1.5 Hz, 4.8 Hz, 1H), 8.26 (dd, J=1.8 Hz, 6.9 Hz, 1H), 7.87 (dd, J=1.5 Hz, 8.4 Hz, 1H), 7.46-7.53 (m, 3H).

Synthesis of 6-[3'-(9H-carbazol-9-yl)biphenyl-3-yl]benzo[4,5]furo[3,2-b]pyridine Into a 100 mL three-neck flask were added 0.75 g (2.4 mmol) of benzo[4,5]furo[3,2-b]pyridin-6-yl 1,1,1-trifluoromethanesulfonate, 0.94 g (2.6 mmol) of 3'-(9H-carbazol-9-yl)-3-biphenylboronic acid, 72 mg (0.24 mmol) of tri(o-tolyl)phosphine, 0.65 g (4.7 mmol) of potassium carbonate, 25 mL of toluene, 10 mL of ethanol, and 5.0 mL of water. This mixture was degassed by being stirred under reduced pressure, and the atmosphere in the flask was replaced with nitrogen. To this mixture was added 11 mg (0.047 mmol) of palladium(II) acetate, and stirring was performed under a nitrogen stream at 80° C. for 24 hours. After a certain period of time, water was added to the reaction mixture, and an aqueous layer was subjected to extraction with toluene. The obtained solution of the extract and the organic layer were combined, and washed with water and saturated saline, and then magnesium sulfate was added to the organic layer so that moisture was adsorbed. This mixture was subjected to gravity filtration, and the filtrate was concentrated to give a brown solid. The obtained solid was purified by silica gel column chromatography (chloroform) to give a colorless transparent oily substance. The obtained oily substance was recrystallized with a mixed solvent of hexane and toluene to give a white powder. The obtained white powder was purified by high-performance liquid column chromatography (HPLC). The obtained fractions were concentrated to give a colorless transparent oily substance. The obtained oily substance was recrystallized with a mixed solvent of hexane and ethyl acetate, so that 0.41 g of a white powder of the target substance was obtained in a yield of 36%. The synthesis scheme of this step is shown in Formula (C-3).

Scheme (C-3)

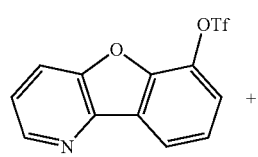

+

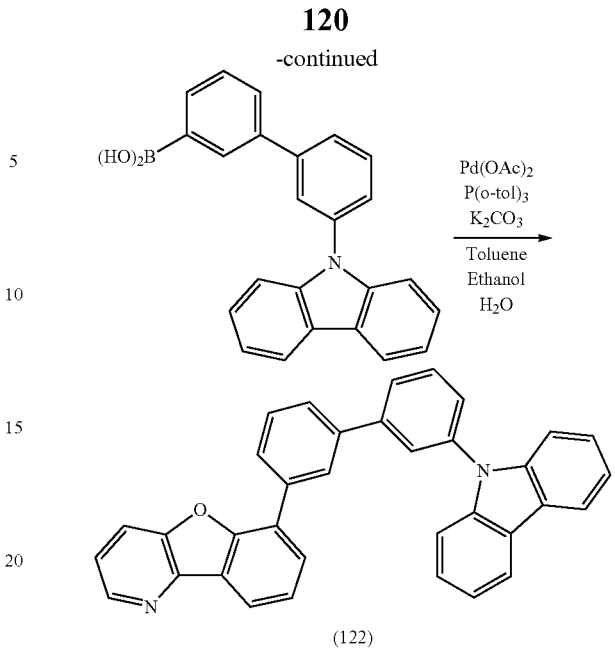

(122)

The obtained compound was subjected to nuclear magnetic resonance spectrometry ($^1$H NMR), and the results are shown below. The results revealed that mCzBPBfpy-02 was obtained.

$^1$H NMR (CDCl$_3$, 300 MHz): δ=8.67 (dd, J=2.1 Hz, 4.9 Hz, 1H), 8.25 (dd, J=1.4 Hz, 7.8 Hz, 1H), 8.16-8.18 (m, 3H), 7.89-7.94 (m, 2H), 7.65-7.83 (m, 6H), 7.58-7.64 (m, 1H), 7.50-7.58 (m, 3H), 7.36-7.45 (m, 3H), 7.27-7.33 (m, 2H).

Figure 16A:
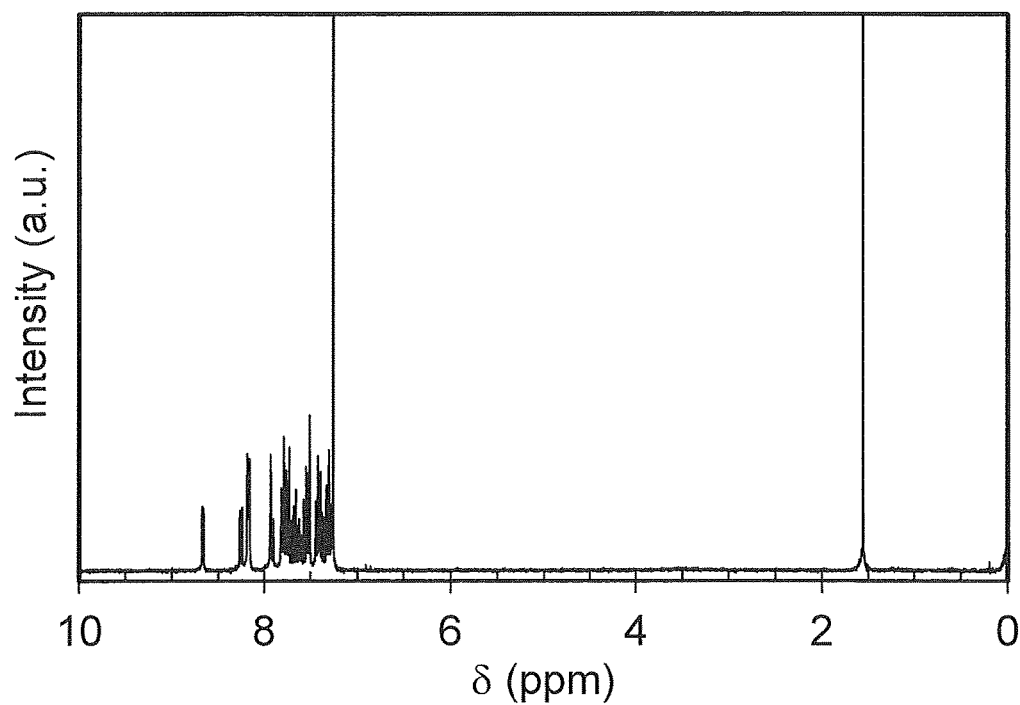
FIGS. 16A and 16B are NMR charts of mCzBPBfpy-02.
Figure 16B:
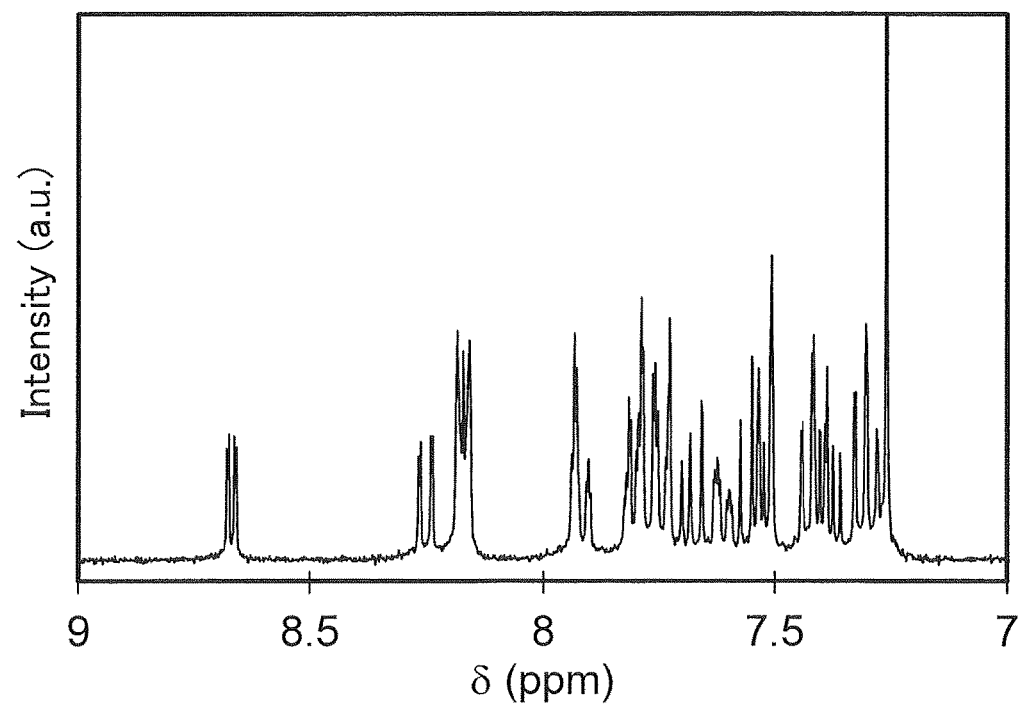

FIGS. 16A and 16B are $^1$H NMR charts. Note that FIG. 16B is a chart showing an enlarged part in the range of 7 ppm to 9 ppm of FIG. 16A. The results revealed that mCzBPBfpy-02 was obtained.

Physical Properties of mCzBPBfpy-02

Next, the absorption spectrum and emission spectrum of a toluene solution of mCzBPBfpy-02 were measured in a manner similar to that described in Example 1.

An absorption peak of mCzBPBfpy-02 in the toluene solution was observed at approximately 341 nm, and emission wavelength peaks thereof were observed at 347 nm and 362 nm (excitation wavelength: 325 nm). Accordingly, the compound of one embodiment of the present invention can be used as a host material for a light-emitting substance or a host material for a substance emitting phosphorescence in the visible region.

The characteristics of oxidation-reduction reaction of mCzBPBfpy-02 were examined by cyclic voltammetry (CV) measurement in a manner similar to that described in Example 1.

According to the measurement results, the oxidation potential was −5.92 eV and the reduction potential was −2.47 eV. When the oxidation potential was regarded as a HOMO level and the reduction potential was regarded as a LUMO level, a gap between the HOMO level and the LUMO level was estimated to be 3.45 eV. The energy value of the first peak on the short wavelength side of the emission spectrum caused by photoexcitation was 3.57 eV, which was close to the estimated value; thus, a structural change due to excitation by carrier injection was expected to be small.

Therefore, a light-emitting element can achieve a low driving voltage by using mCzBPBfpy-02 in its light-emitting layer.

Example 4

In this example, in order to attain the knowledge of the relation between the molecular structure and physical properties of the compounds of embodiments of the present invention having a structure in which a carbazole skeleton is bonded to a benzofuropyridyl group or a benzothienopyridyl group through an arylene group, the HOMO levels, the LUMO levels, and the T1 levels of the structures were obtained by quantum chemical calculation. Note that since not all the physical properties of a compound are examined by the calculation described in this example, sometimes physical properties of compounds cannot be compared by only the calculation results shown in this example. For example, the thermal stability of a compound contained in the EL layer significantly influences the reliability of a light-emitting device, but is not a subject of the calculation here. Therefore, sometimes there is a compound whose practicality should be estimated to be relatively high in terms of reliability although the performance of the compound is estimated to be relatively low by the calculation.

The most stable structures in the singlet state and in the triplet state were obtained by calculation using the density functional theory. In addition, vibration analysis was conducted on each of the most stable structures. As a basis function, 6-311G was applied to all the atoms. Furthermore, to improve calculation accuracy, the p function and the d function as polarization basis sets were added respectively to hydrogen atoms and atoms other than hydrogen atoms. As a functional, B3LYP was used. Each of the HOMO level and the LUMO level of the structure in the singlet state was calculated. Then, a zero-point corrected energy difference was obtained from the most stable structures in the singlet ground state and in the lowest excited triplet state, and the T1 level was calculated from the zero-point corrected energy difference. Gaussian 09 was used as the quantum chemistry computational program.

<Calculation 1>

In a group of compounds each having a structure in which a carbazole skeleton is bonded to a benzofuropyridyl group, the influence of a substituent bonded to the carbazole skeleton on the HOMO level, the LUMO level, and the T1 level of the compound was examined by calculations of the following compounds.

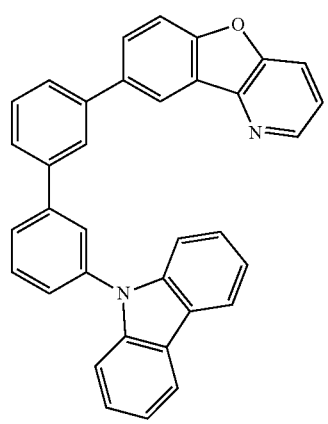
(320)

-continued

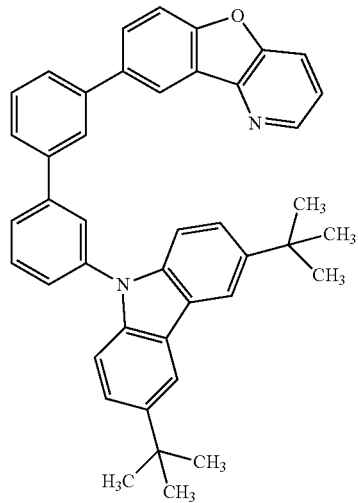
(501)

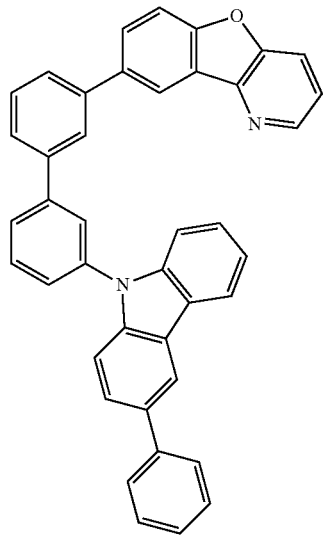
(502)

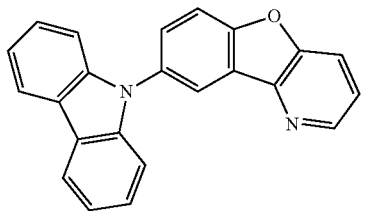
(505)

-continued (503)

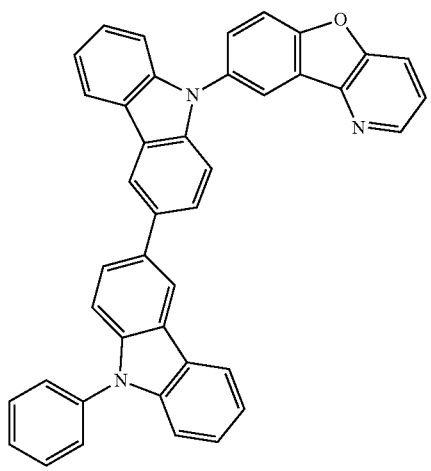

(504)

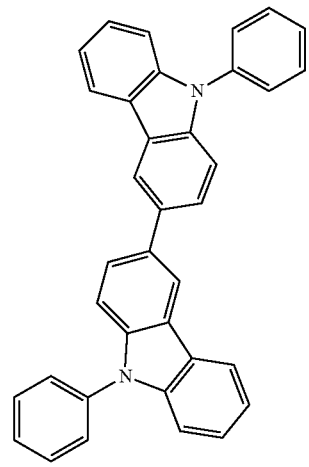

Table 3 shows the calculation results.

TABLE 3

| Formula number | LUMO level [eV] | HOMO level [eV] | T1 level [eV] |
| --- | --- | --- | --- |
| (320) | −1.69 | −5.59 | 2.83 |
| (501) | −1.68 | −5.38 | 2.82 |
| (502) | −1.70 | −5.49 | 2.79 |
| (505) | −1.84 | −5.60 | 2.90 |
| (503) | −1.82 | −5.21 | 2.76 |
| (504) | −0.97 | −5.22 | 2.75 |

The calculation was performed on a compound represented by Structural Formula (320) and compounds represented by Structural Formulae (501) and (502) in each of which a substituent is bonded to a carbazole skeleton of the compound represented by Structural Formula (320). In addition, the calculation was performed on a compound represented by Structural Formula (505), a compound represented by Structural Formula (503) in which another carbazolyl group is bonded to the 3-position of a carbazole skeleton of the compound represented by Structural Formula (505), and a compound represented by Structural Formula (504). Note that the compound represented by Structural Formula (320) was used for the light-emitting element 1 in Example 2, and the compound represented by Structural Formula (503) was used for the comparative light-emitting element 1 in Example 2.

First, the calculation results of the compound represented by Structural Formula (320) and the compounds represented by Structural Formulae (501) and (502) in each of which a substituent is bonded to the carbazole skeleton of the compound represented by Structural Formula (320) are compared. The T1 levels of the compounds represented by Structural Formulae (320) and (501) are substantially the same. The T1 level of the compound represented by Structural Formula (502) is slightly lower, but its absolute value is large. This is probably because when an aliphatic hydrocarbon group is bonded to the carbazole skeleton, conjugation is less likely to extend, and when an aryl group is bonded to the carbazole skeleton, conjugation extends but the degree of the extension is not large because the aryl group is one phenyl group. Therefore, in one embodiment of the present invention, an alkyl group and a phenyl group can be used as a substituent bonded to the carbazole skeleton having a high T1 level. Note that these compounds have substantially the same LUMO levels. This is probably because the LUMO extends over the benzofuropyridyl group. The HOMO levels of the compounds represented by Structural Formulae (501), (502), and (320) have a relation of (320)<(502)<(501). That is, an aliphatic hydrocarbon group, a phenyl group, and hydrogen have a higher electron-donating property in descending order.

Next, the calculation results of the compound represented by Structural Formula (505) and the compound represented by Structural Formula (503) in which a carbazolyl-3-yl group is bonded to the 3-position of the carbazole skeleton of the compound represented by Structural Formula (505) as a substituent are compared. The compound represented by Structural Formula (503) has a shallower HOMO level and a lower T1 level as shown in Table 3.

According to the calculation results, when the carbazolyl-3-yl group is used as a substituent bonded to the carbazole skeleton, the conjugation extends and the T1 spin orbit extends from the carbazole skeleton to the carbazolyl group, which is a factor of the decrease in the T1 level. Like the compound represented by Structural Formula (503), the compound represented by Structural Formula (504) has a structure in which two carbazolyl groups are bonded. According to Table 3, each of the compounds represented by Structural Formulae (503) and (504) has a shallow HOMO level and a low T1 level. This indicates that the T1 level is determined by the structure that includes the carbazole skeleton to the carbazolyl group. Therefore, when the carbazolyl-3-yl group is used as the substituent bonded to the carbazole skeleton, the T1 level tends to be low.

<Calculation 2>

Next, in a group of compounds each having a structure in which a carbazole skeleton is bonded to a benzofuropyridyl group, the influence of an arylene group between the carbazole skeleton and the benzofuropyridyl group on the HOMO level, the LUMO level, and the T1 level of the compound was examined by calculations of the following compounds.

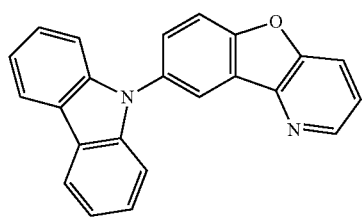
(505)
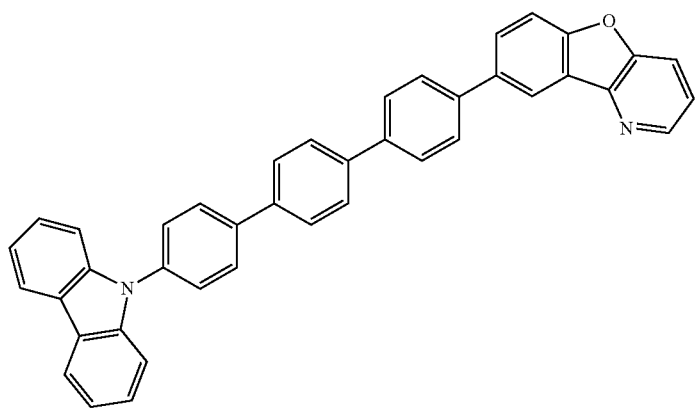
(512)
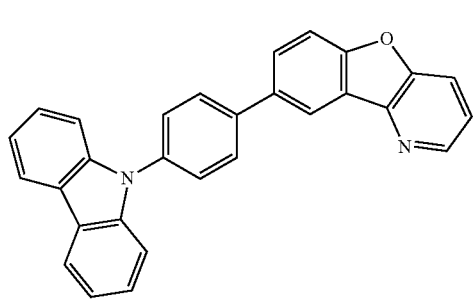
(510)
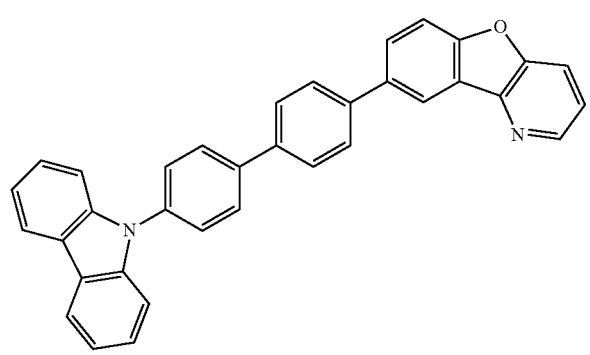
(511)
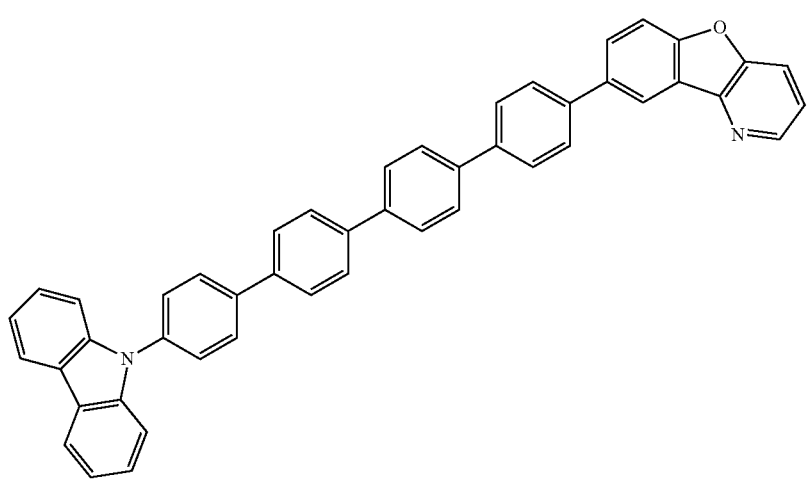
(513)

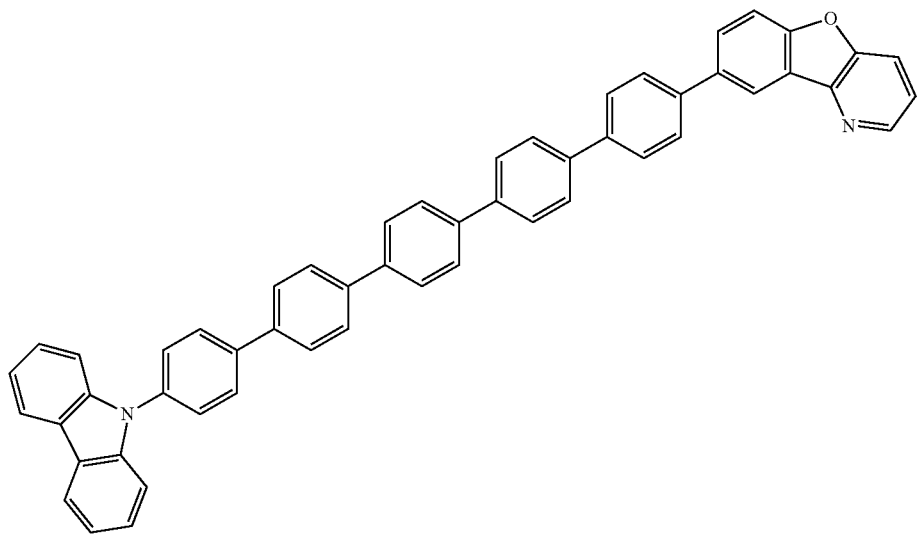
(514)

Table 4 shows the calculation results.

TABLE 4

| Formula number | LUMO level [eV] | HOMO level [eV] | T1 level [eV] |
| --- | --- | --- | --- |
| (505) | −1.84 | −5.60 | 2.90 |
| (510) | −1.73 | −5.57 | 2.74 |
| (511) | −1.69 | −5.56 | 2.52 |
| (512) | −1.67 | −5.56 | 2.43 |
| (513) | −1.67 | −5.56 | 2.39 |
| (514) | −1.71 | −5.56 | 2.37 |

The calculation was performed on a compound represented by Structural Formula (505) in which an arylene group is not disposed between a carbazole skeleton and a benzofuropyridyl group, a compound represented by Structural Formula (510) in which a phenylene group is disposed as an arylene group, a compound represented by Structural Formula (511) in which two phenylene groups are disposed, a compound represented by Structural Formula (512) in which three phenylene groups are disposed, a compound represented by Structural Formula (513) in which four phenylene groups are disposed, and a compound represented by Structural Formula (514) in which five phenylene groups are disposed. Note that these phenylene groups are bonded at the para positions.

As shown in Table 4, the T1 level decreases as the number of phenylene groups increases. This is because the conjugation of the T1 spin orbit extends over the arylene group as the number of phenylene groups increases. Therefore, in order to keep the T1 level high, the number of arylene groups between the carbazole skeleton and the benzofuropyridyl group is preferably small, specifically, the number is preferably 5 or smaller. However, in the case where the carbazole skeleton is directly bonded to the benzofuropyridyl group without an arylene group therebetween, the compound has a low molecular weight and low thermal stability, and thus an EL layer including the compound has low reliability. For this reason, the number of arylene groups is preferably 1 or larger.

<Calculation 3>

Next, in a group of compounds each having a structure in which a carbazole skeleton is bonded to a benzofuropyridyl group, the influence of the substitution site of an arylene group between the carbazole skeleton and the benzofuropyridyl group on the HOMO level, the LUMO level, and the T1 level of the compound was examined by calculations of the following compounds.

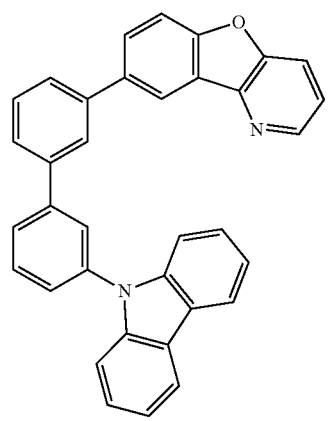
(320)

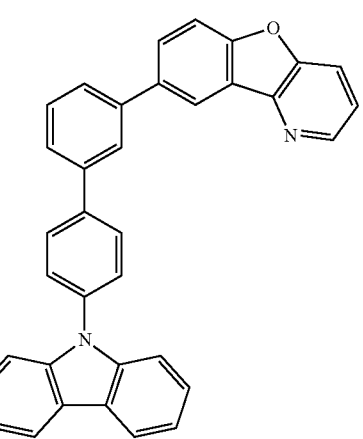
(515)

-continued

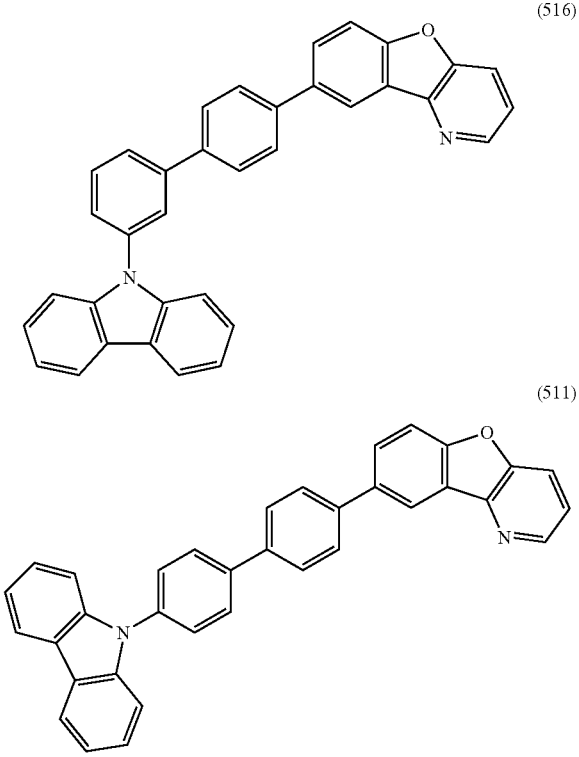

(516)

(511)

Table 5 shows the calculation results.

TABLE 5

| Formula number | LUMO level [eV] | HOMO level [eV] | T1 level [eV] |
|---|---|---|---|
| (320) | −1.69 | −5.59 | 2.83 |
| (515) | −1.69 | −5.58 | 2.71 |
| (516) | −1.68 | −5.59 | 2.58 |
| (511) | −1.69 | −5.56 | 2.52 |

The calculation was performed on four compounds each having a structure in which two phenylene groups are disposed between a carbazole skeleton and a benzofuropyridyl group. In each of the four compounds, groups and skeletons are single-bonded. The four compounds have the following respective features. In the compound represented by Structural Formula (320), each of the two phenylene groups has a single bond at the meta position. In the compound represented by Structural Formula (515), a phenylene group single-bonded to the benzofuropyridyl group is single-bonded to the other phenylene group at the meta position, and the other phenylene group is single-bonded to the carbazole skeleton at the para position. In the compound represented by Structural Formula (516), a phenylene group single-bonded to the benzofuropyridyl group is single-bonded to the other phenylene group at the para position, and the other phenylene group is single-bonded to the carbazole skeleton at the meta position. In the compound represented by Structural Formula (511), each of the two phenylene groups has two single bonds at the para positions.

As shown in Table 5, the four compounds have substantially the same LUMO levels and substantially the same HOMO levels. This is because the LUMO extends over the benzofuropyridyl group and the HOMO extends over the carbazolyl group. As the number of meta-position single-bonds the two phenylene groups have increases, the T1 level is higher. Furthermore, between the compounds represented by Structural Formulae (515) and (516) each having one meta-position single-bond and one para-position single-bond, the compound represented by Structural Formula (515) in which the phenylene group single-bonded to the benzofuropyridyl group is single-bonded to the other phenylene group at the meta position has a higher T1 level.

In the calculation, the T1 spin orbit extends over two or more six-membered rings which are bonded at the para positions, determining the T1 level. That is, the number of six-membered rings including the benzofuropyridyl group bonded at the para-positions is two in the compound represented by Structural Formula (515) whereas is three in the compound represented by Structural Formula (516). As the T1 spin orbit extends due to conjugation, the T1 level tends to be lowered. From this calculation, it is found that in the compound represented by Structural Formula (516) in which the relation between two single bonds of the phenylene group bonded to the benzofuropyridyl group is the para position, the T1 level spin orbit extends from the biphenylene group to the benzofuropyridyl group; while in the compounds represented by Structural Formulae (320) and (515) in which the relation is the meta position, the T1 level spin orbit extends only to the biphenylene group. Therefore, each of the compounds represented by Structural Formulae (320) and (515) has a higher T1 level than the compound represented by Structural Formula (516). Moreover, in the compound of one embodiment of the present invention, the T1 level becomes higher as the number of six-membered rings bonded at the para-positions is smaller; and when all the positions at which phenylene groups are single-bonded are meta positions, the T1 level can be kept high even when the number of phenylene groups is large.

<Calculation 4>

Next, in a group of compounds each having a structure in which a carbazole skeleton is bonded to a benzofuropyridyl group, the influence of the substitution site of an arylene group bonded to the benzofuropyridyl group on the HOMO level, the LUMO level, and the T1 level of the compound was examined by calculations of the following compounds.

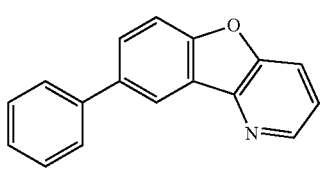

(300)

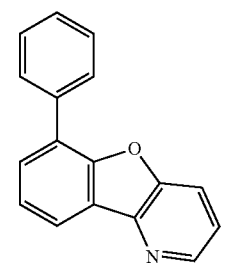

(301)

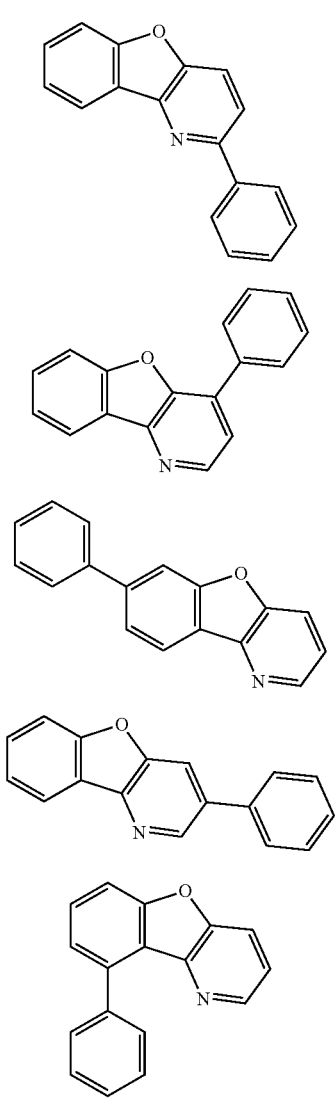

(302)

(303)

(304)

(305)

(306)

Table 6 shows the calculation results.

TABLE 6

| Formula number | LUMO level [eV] | HOMO level [eV] | T1 level [eV] | Substitution position on the benzofuropyridine ring |
|---|---|---|---|---|
| (300) | −1.61 | −6.24 | 2.90 | 8-position |
| (301) | −1.65 | −6.24 | 2.69 | 6-position |
| (302) | −1.64 | −6.14 | 2.77 | 2-position |
| (303) | −1.77 | −6.45 | 2.79 | 4-position |
| (304) | −1.73 | −6.19 | 2.60 | 7-position |
| (305) | −1.73 | −6.22 | 2.59 | 3-position |
| (306) | −1.68 | −6.16 | 2.66 | 9-position |

The calculation was performed on a compound in which a phenyl group is used as a substituent of benzofuropyridine. The calculation was performed on seven compounds having different substitution sites of the phenyl group. The aim of this calculation is to attain the knowledge of the influence of the substitution site of the arylene group bonded to the benzofuropyridyl group in the compound of one embodiment of the present invention on the LUMO level, the HOMO level, and the T1 level.

In a compound represented by Structural Formula (300), a phenyl group is bonded to a carbon atom at the 8-position of benzofuropyridine; in a compound represented by Structural Formula (301), the 6-position; in a compound represented by Structural Formula (302), the 2-position; in a compound represented by Structural Formula (303), the 4-position; in a compound represented by Structural Formula (304), the 7-position; in a compound represented by Structural Formula (305), the 3-position; and in a compound represented by Structural Formula (306), the 9-position.

Table 6 shows that the LUMO level, the HOMO level, and the T1 level vary depending on the substitution site of the phenyl group. It is also shown that the compounds in each of which a phenyl group is bonded to carbon at the 2-position, the 4-position, the 6-position, or the 8-position have a higher T1 level than the compounds in each of which a phenyl group is bonded to carbon at the 3-position, the 7-position, or the 9 position. This indicates that when two six-membered rings of the benzofuropyridine skeleton and the phenyl group are single-bonded at the meta position, the T1 level is high. The compounds in each of which a phenyl group is bonded to carbon at the 2-position, the 4-position, the 6-position, or the 8-position can be used in elements having an emission wavelength in the visible region. In particular, the compounds can be used as host materials for elements emitting blue phosphorescence because the T1 level can be kept high. The compounds in each of which a phenyl group is bonded to carbon at the 2-position or the 8-position are more preferred because a higher T1 level can be obtained. The compound in which a phenyl group is bonded to carbon at the 2-position is further more preferred because the highest T1 level can be obtained. In the compounds in each of which a phenyl group is bonded to carbon at the 3-position or the 7-position, two six-membered rings of the benzofuropyridine skeleton and the phenyl group are single-bonded at the para position, which is preferable because the compounds have a high carrier-transport property. These compounds can be used in a fluorescent element or a phosphorescent element emitting long-wavelength light including green light.

<Calculation 5>

Next, in a group of compounds each having a structure in which a carbazole skeleton and a benzothienopyridyl group are bonded to each other, the influence of the substitution site of an arylene group bonded to the benzothienopyridyl group on the HOMO level, the LUMO level, and the T1 level of the compound was examined by calculations of the following compounds.

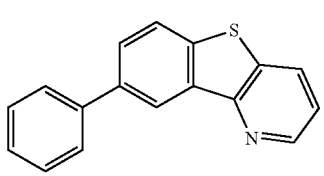

(400)

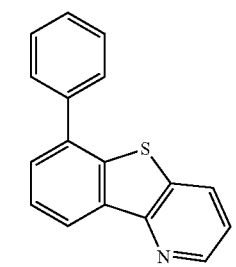

(401)

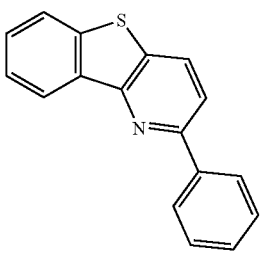
(402)

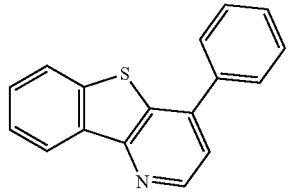
(403)

Table 7 shows the calculation results.

TABLE 7

| Formula number | LUMO level [eV] | HOMO level [eV] | T1 level [eV] | Substitution position on the benzofuropyridine ring |
|---|---|---|---|---|
| (400) | −1.58 | −6.05 | 2.82 | 8-position |
| (401) | −1.56 | −6.08 | 2.77 | 6-position |
| (402) | −1.63 | −5.99 | 2.69 | 2-position |
| (403) | −1.66 | −6.14 | 2.83 | 4-position |

The calculation was performed on a compound in which a phenyl group is used as a substituent of benzothienopyridine. The calculation was performed on four compounds having different substitution sites of the phenyl group. The aim of this calculation is to attain the knowledge of the influence of the substitution site of the arylene group bonded to the benzothienopyridine group in the compound of one embodiment of the present invention on the LUMO level, the HOMO level, and the T1 level. In addition, another aim of this calculation is to compare benzothienopyridine with benzofuropyridine based on the result of this calculation and the result of the above-described calculation on the benzofuropyridine compound.

In a compound represented by Structural Formula (400), a phenyl group is bonded to a carbon atom at the 8-position of benzothienopyrimidine; in a compound represented by Structural Formula (401), the 6-position; in a compound represented by Structural Formula (402), the 2-position; and in a compound represented by Structural Formula (403), the 4-position.

The comparison between Table 6 and Table 7 shows that in the case where a phenyl group is bonded at the 2-position or the 8-position, the compound including benzofuropyridine tends to have a higher T1 level than the compound including benzothienopyridine. However, in the case where a phenyl group is bonded at the 4-position or the 6-position, the compound including benzothienopyridine tends to have a higher T1 level than the compound including benzofuropyridine. This is probably because an S atom of benzothienopyridine is larger than an O atom of benzofuropyridine, and thus steric hindrance is larger when a substituent is positioned close to the S atom. In either case, in one embodiment of the present invention, when the benzofuropyridyl group is replaced with the benzothienopyridyl group, an expected T1 level is not largely changed.

The comparison between Table 6 and Table 7 also shows that the use of benzofuropyridine can provide a deeper LUMO level and a higher electron-injection property than the use of benzothienopyridine.

<Calculation 6>

Next, in a group of compounds each having a structure in which a carbazole skeleton is bonded to a benzofuropyridyl group, the influence of the substitution site of an arylene group bonded to the benzofuropyridyl group on the HOMO level, the LUMO level, and the T1 level of the compound was examined by calculations of the following compounds.

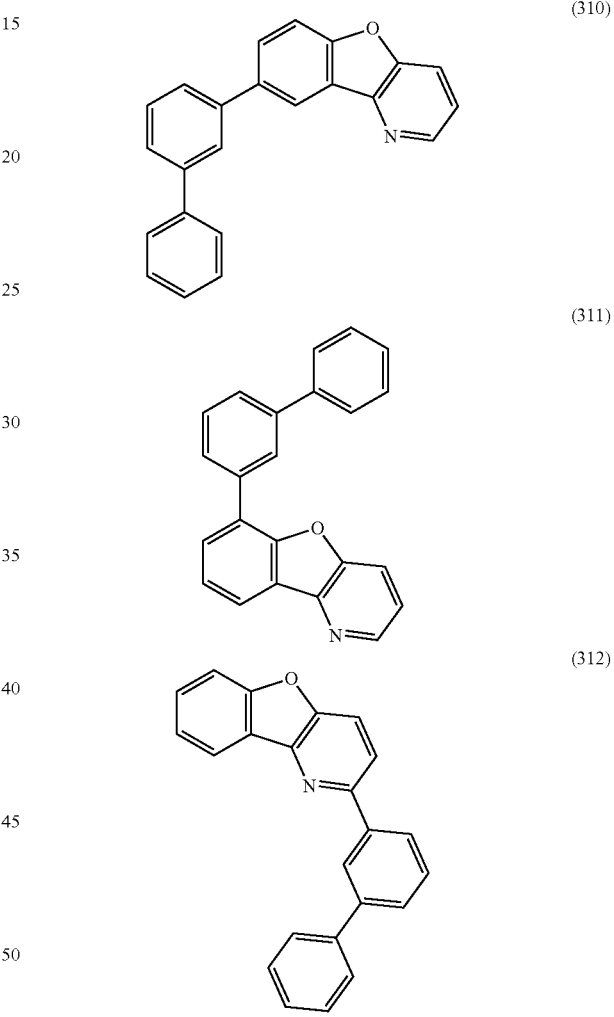

Table 8 shows the calculation results.

TABLE 8

| Formula number | LUMO level [eV] | HOMO level [eV] | T1 level [eV] | Substitution position on the benzofuropyridine ring |
|---|---|---|---|---|
| (310) | −1.62 | −6.19 | 2.86 | 8-position |
| (311) | −1.67 | −6.21 | 2.69 | 6-position |
| (312) | −1.66 | −6.11 | 2.75 | 2-position |
| (313) | −1.88 | −5.63 | 2.77 | 4-position |

The calculation was performed on a compound in which a biphenyl group is used as a substituent of benzofuropyridine. The calculation was performed on four compounds having different substitution sites of the phenyl group. The aim of this calculation is to attain the knowledge of the influence of the substitution site of the arylene group bonded to the benzofuropyridyl group in the compound of one embodiment of the present invention on the LUMO level, the HOMO level, and the T1 level.

As seen from the comparison between Table 8 and Table 6, the result of this calculation is the same as that of Calculation 4.

<Calculation 7>

Next, in a group of compounds each having a structure in which a carbazole skeleton is bonded to a benzofuropyridyl group, the influence of the substitution site of an arylene group bonded to the benzofuropyridyl group on the HOMO level, the LUMO level, and the T1 level of the compound was examined by calculations of the following compounds.

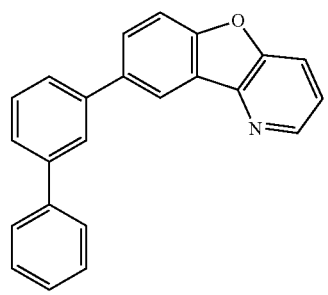

(310)

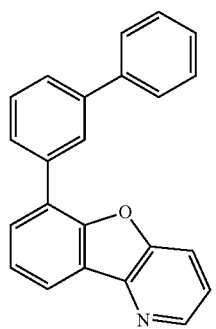

(311)

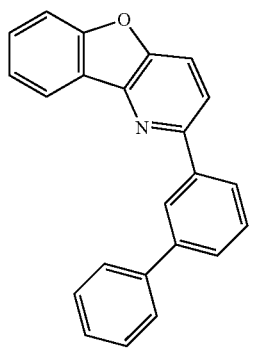

(312)

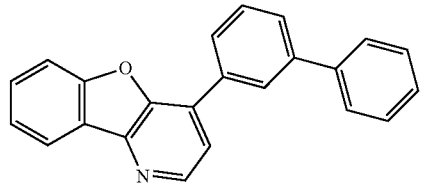

(313)

Table 9 shows the calculation results.

TABLE 9

| Formula number | LUMO level [eV] | HOMO level [eV] | T1 level [eV] | Substitution position on the benzofuropyridine ring |
|---|---|---|---|---|
| (310) | −1.69 | −5.59 | 2.83 | 8-position |
| (311) | −1.76 | −5.61 | 2.69 | 6-position |
| (312) | −1.72 | −5.59 | 2.74 | 2-position |
| (313) | −1.88 | −5.63 | 2.77 | 4-position |

The calculation was performed on four compounds of embodiments of the present invention. The substitution site of an arylene group is different in each compound. The aim of this calculation is to attain the knowledge of the influence of the substitution site of the arylene group bonded to the benzofuropyridyl group in the compound of one embodiment of the present invention on the LUMO level, the HOMO level, and the T1 level.

As seen from the comparison between Tables 9, 8, and 6, the result of this calculation is the same as that of Calculation 4.

From Table 3, Table 4, Table 5, and Table 9 which show the results of the calculation assuming the state where the carbazole skeleton is bonded, it is found that the HOMO extends over the carbazole skeleton and accordingly the carbazole skeleton transfers holes. Bonding to N at the 9-position of the carbazole skeleton is preferable because conjugation is less likely to extend through N and the distribution of HOMO and that of LUMO are likely to be separated and thus the T1 level can be kept high.

In this example, the relation between the molecular structure and the physical properties of the compounds of embodiments of the present invention having a structure in which a carbazole skeleton is bonded to a benzofuropyridyl group or a benzothienopyridyl group through an arylene group and several other compounds has been described on the basis of the calculations.

Example 5

Synthesis Example 3

In this example, a method for synthesizing 4-[3'-(9H-carbazol-9-yl)biphenyl-3-yl]benzo[4,5]furo[3,2-b]pyridine (abbreviation: mCzBPBfpy-03) (Structural Formula (134)) that is the compound described in Embodiment 1 having a structure in which a carbazole skeleton is bonded to a benzofuropyridyl group or a benzothienopyridyl group through an arylene group is described. The structural formula of mCzBPBfpy-03 is shown below.

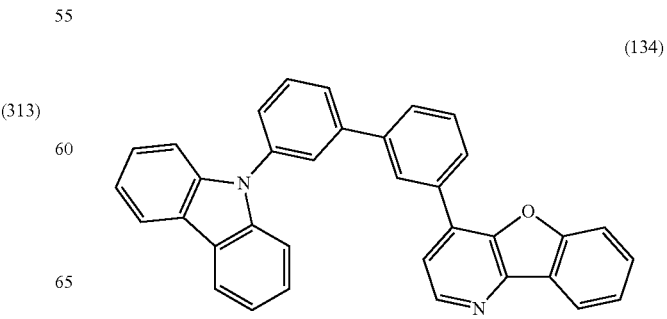

(134)

Synthesis of 4-iodobenzo[4,5]furo[3,2-b]pyridine

Into a 100 mL three-neck flask was put 0.66 g (3.9 mmol) of benzo[4,5]furo[3,2-b]pyridine, and the atmosphere in the flask was replaced with nitrogen. Into this was added 40 mL of dehydrated tetrahydrofuran, and the mixture was cooled down to −80° C. under a nitrogen stream. After the cooling, 4.7 mL (4.7 mmol) of 1.0M lithium diisopropylamide (abbreviation: LDA) was dropped. This solution was stirred at the same temperature for 0.5 hours. After a certain period of time, 1.5 g (5.9 mmol) of iodine was added, and the temperature of the solution was raised to room temperature and stirring was performed for 20 hours. After a certain period of time, an aqueous solution of sodium thiosulfate was added to this mixture, and extraction was performed with ethyl acetate. The obtained solution was purified by silica gel column chromatography (developing solvent with a toluene:ethyl acetate ratio of 9:1) to give 0.73 g of a brown solid of the target substance in a yield of 64%. Formula (D-1) is shown below.

Scheme (D-1)

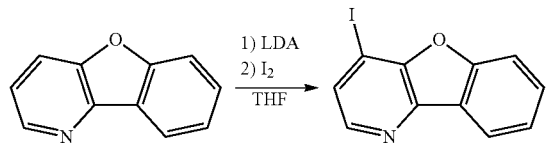

Figure 22A:
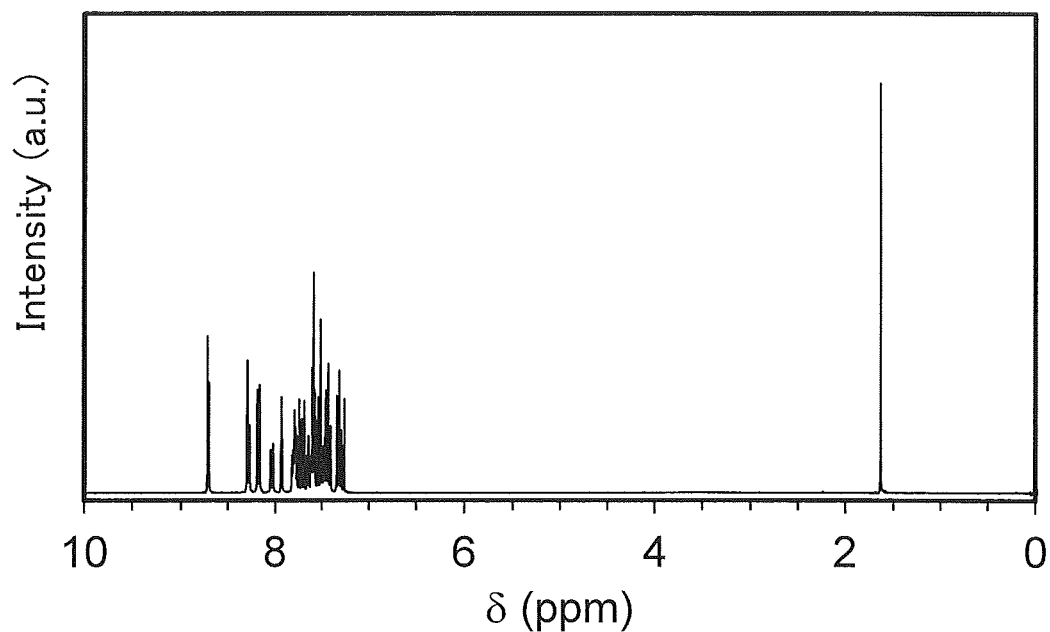
FIGS. 22A and 22B are NMR charts of mCzBPBfpy-03.
Figure 22B:
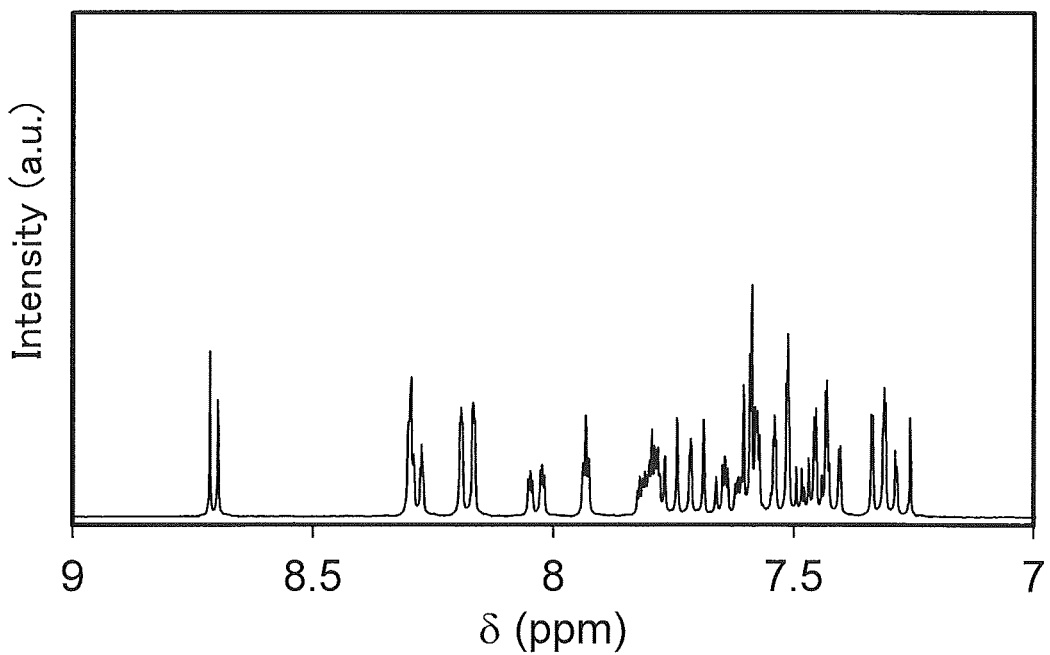

$^1$H NMR data of the obtained compound is shown below. FIGS. 22A and 22B show an NMR spectrum.

$^1$H NMR (CDCl$_3$, 300 MHz): δ=7.49 (td, J=1.5 Hz, J=7.8 Hz, 1H), 7.63 (td, J=1.5 Hz, 8.4 Hz, 1H), 7.71 (dd, 1.5 Hz, 8.4 Hz, 1H), 7.79 (d, J=4.8 Hz, 1H), 8.23 (dd, J=1.5 Hz, 7.8 Hz, 1H), 8.28 (d, J=4.8 Hz, 1H).

Synthesis of 4-[3'-(9H-carbazol-9-yl)biphenyl-3-yl]benzo[4,5]furo[3,2-b]pyridine (abbreviation: mCzBPBfpy-03)

Into a Schlenk flask were put 0.73 g (2.5 mmol) of 4-iodobenzo[4,5]furo[3,2-b]pyridine, 1.0 g (2.8 mmol) of 3'-(9H-carbazol-9-yl)-3-biphenylboronic acid, 76 mg (0.25 mmol) of tri(o-tolyl)phosphine, 0.69 g (5.0 mmol) of potassium carbonate, 13 mL of toluene, 2.5 mL of ethanol, and 1.3 mL of water. This mixture was degassed by being stirred under reduced pressure, and the atmosphere in the flask was replaced with nitrogen. To this mixture was added 11 mg (0.050 mmol) of palladium(II) acetate, and stirring was performed under a nitrogen stream at 90° C. for 10 hours. After a certain period of time, extraction was performed with toluene, and purification was performed by silica gel column chromatography (developing solvent: chloroform) to give a yellow oily substance. This was recrystallized with a mixed solvent of hexane and toluene to give 0.75 g of a yellow powder of the target substance in a yield of 60%. Formula (D-2) is shown below.

Scheme (D-2)

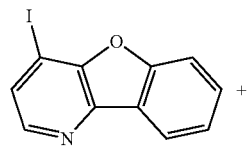

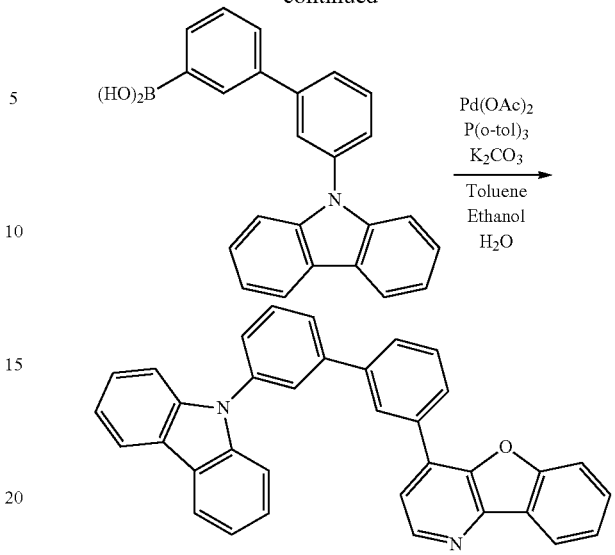

By a train sublimation method, 0.72 g of the obtained yellow powder was purified. The purification by sublimation was conducted by heating at 225° C. under a pressure of 2.8 Pa with a flow rate of argon gas of 5.0 mL/min to give 0.57 g of a white solid of mCzBPBfpy-03 in a yield of 79%.

$^1$H NMR data of the obtained compound is shown below. The results revealed that mCzBPBfpy-03 was obtained.

$^1$H NMR (CDCl$_3$, 300 MHz): δ=7.31 (td, J=1.0 Hz, J=7.8 Hz, 2H), 7.40-7.50 (m, 3H), 7.51-7.55 (m, 2H), 7.57-7.66 (m, 4H), 7.70 (d, J=7.8 Hz, 1H), 7.74-7.83 (m, 3H), 7.93 (t, J=1.5 Hz, 1H), 8.04 (dt, J=1.5 Hz, J=7.8 Hz, 1H), 8.18 (dd, J=1.5 Hz, 8.7 Hz, 2H), 8.27-8.29 (m, 2H), 8.71 (d, J=5.1 Hz, 1H).

FIGS. 22A and 22B are $^1$H NMR charts. Note that FIG. 22B is a chart showing an enlarged part in the range of 7 ppm to 9 ppm of FIG. 22A. The results revealed that mCzBPBfpy-03 was obtained.

The obtained compound was analyzed by LC/MS. The measurement was performed in a manner similar to that described in Example 1. Energy (collision energy) for the collision with argon was 50 eV.

Figure 23:
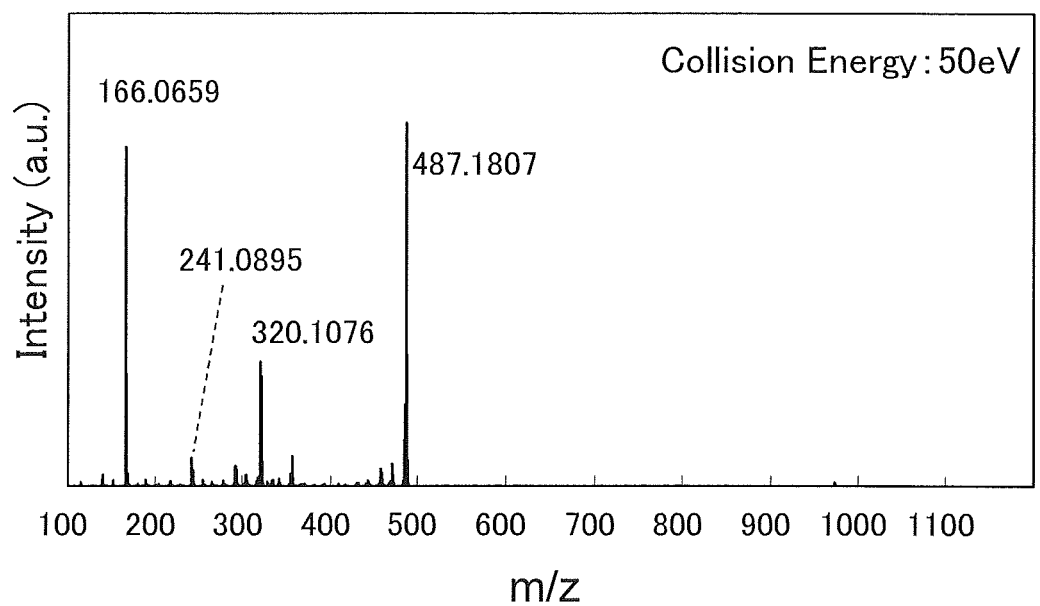
FIG. 23 shows an MS spectrum of mCzBPBfpy-03.

The detection results of the dissociated product ions by time-of-flight (TOF) MS are shown in FIG. 23.

It was found from the result of FIG. 23 that product ions of mCzBPBfpy-03 were detected mainly around m/z=320, 241, 166. Note that the result in FIG. 23 shows characteristics derived from mCzBPBfpy-03 and therefore can be regarded as important data for identifying mCzBPBfpy-03 contained in a mixture.

The product ion around m/z=320 is presumed to be a cation expressed as $C_{23}H_{14}NO^+$ in the state where carbazole is dissociated from mCzBPBfpy-03. The product ion around m/z=241 is presumed to be a radical cation expressed as $C_{18}H_{11}N^+$ of 9-phenyl carbazole in mCzBPBfpy-03. The product ion around m/z=166 is presumed to be a cation expressed as $C_{12}H_8N^+$ of carbazole in mCzBPBfpy-03. These indicate that mCzBPBfpy-03 includes a carbazole skeleton and a benzene skeleton. Note that there is a possibility that the above m/z values±1 are detected as protonation or deprotonation products of the product ions.

Physical Properties of mCzBPBfpy

Figure 25:
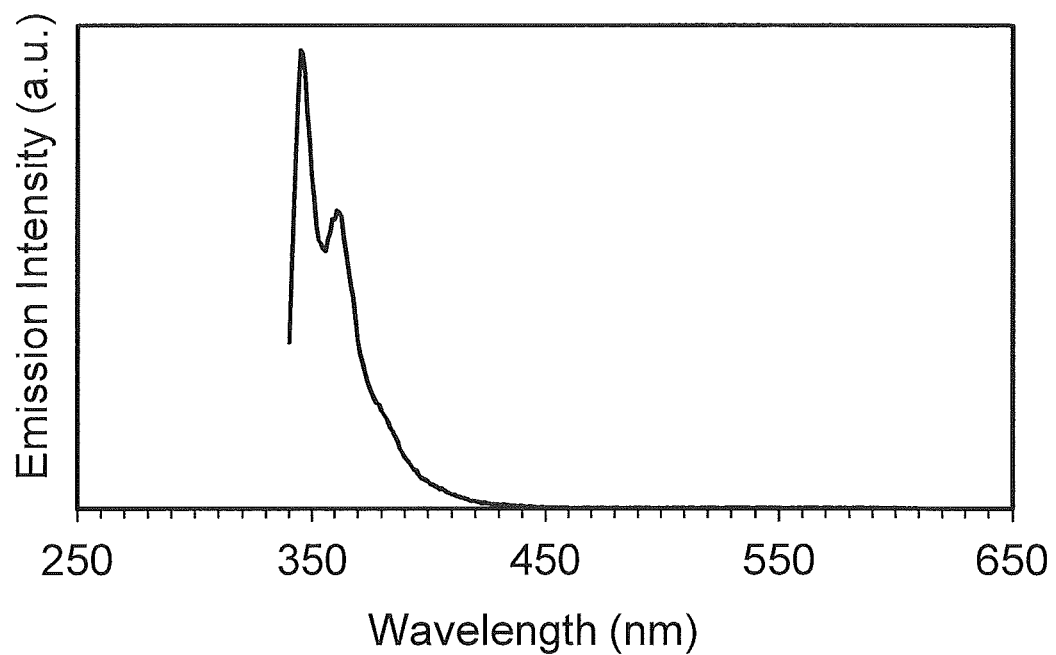
FIG. 25 shows an emission spectrum of a solution of mCzBPBfpy-03.
Figure 26:
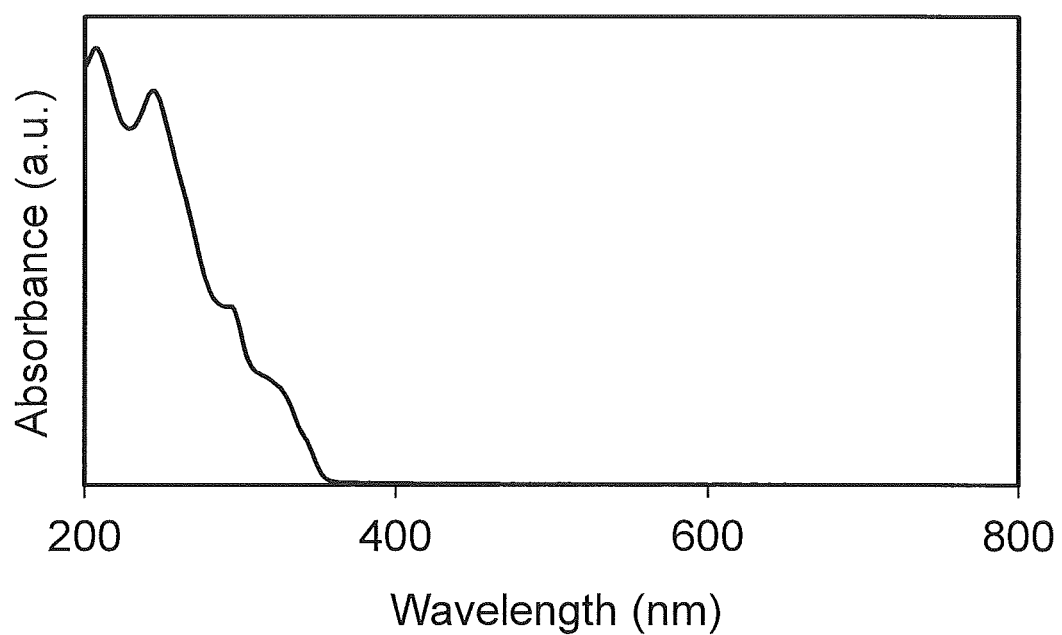
FIG. 26 shows an absorption spectrum of a thin film of mCzBPBfpy-03.
Figure 27:
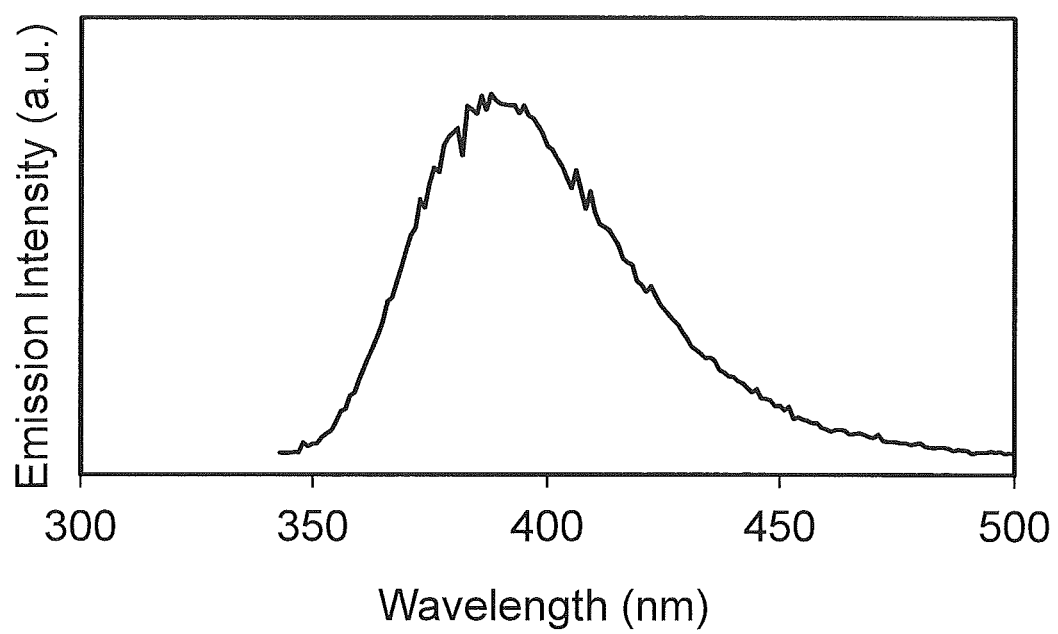
FIG. 27 shows an emission spectrum of a thin film of mCzBPBfpy-03.

FIGS. 22A and 22B show an absorption spectrum of a toluene solution of mCzBPBfpy-03, and FIG. 25 shows an emission spectrum thereof. FIG. 26 shows an absorption spectrum of a thin film of mCzBPBfpy-03, and FIG. 27 shows an emission spectrum thereof. The absorption and emission spectra of the solution and the emission spectrum of the thin film were measured in a manner similar to that described in Example 1. The absorption spectrum of the thin film including the absorption spectrum of the quartz substrate was measured with an ultraviolet-visible spectrophotometer (U-4100, produced by Hitachi High-Technologies Corporation).

Figure 24:
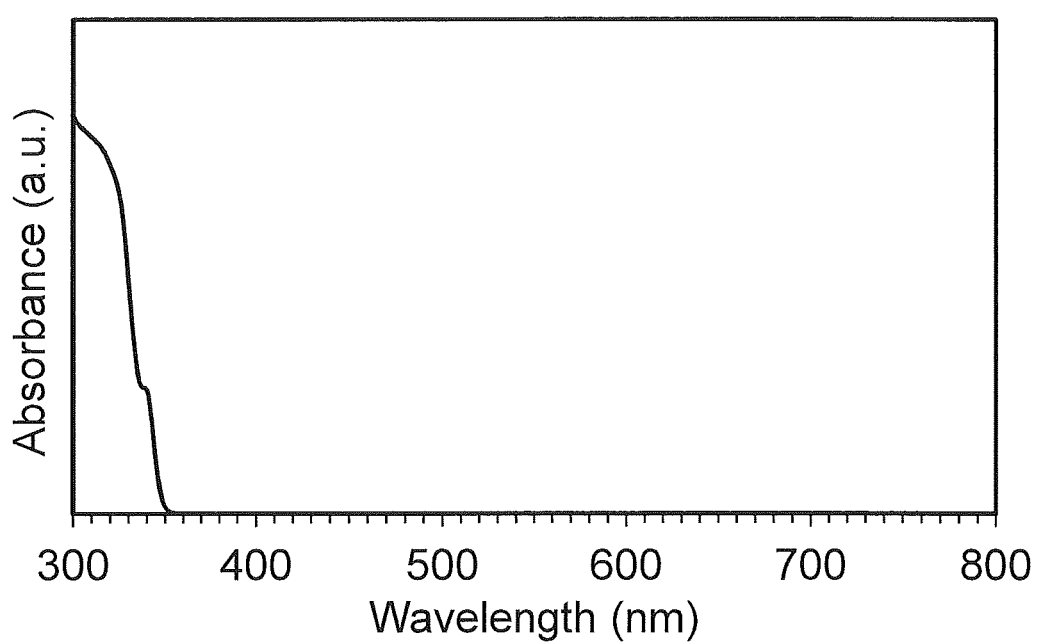
FIG. 24 shows an absorption spectrum of a solution of mCzBPBfpy-03.

As observed in FIG. 24 and FIG. 25, an absorption peaks of mCzBPBfpy-03 in the toluene solution is at approximately 341 nm, and emission wavelength peaks thereof are at 345 nm and 361 nm (excitation wavelength: 325 nm). As observed in FIG. 26 and FIG. 27, absorption peaks of the thin film of mCzBPBfpy-03 are at approximately 342 nm, 325 nm, 312 nm, 291 nm, and 265 nm, and an emission wavelength peak thereof is at 398 nm (excitation wavelength: 339 nm). It was found that mCzBPBfpy-03 emitted violet light. Therefore, the compound of one embodiment of the present invention can be used as a host material for a light-emitting substance or a host material for a substance emitting phosphorescence in the visible region.

The characteristics of oxidation-reduction reaction of mCzBPBfpy-03 were examined by cyclic voltammetry (CV) measurement. The measurement was performed in a manner similar to that described in Example 1.

According to the measurement results, the oxidation potential was −5.90 eV and the reduction potential was −2.66 eV. When the oxidation potential was regarded as a HOMO level and the reduction potential was regarded as a LUMO level, a gap between the HOMO level and the LUMO level was estimated to be 3.24 eV. The energy value of the first peak on the short wavelength side of the emission spectrum caused by photoexcitation was 3.59 eV, which was close to the estimated value; thus, a structural change due to excitation by carrier injection was expected to be small. Therefore, a light-emitting element can achieve a low driving voltage by using mCzBPBfpy-03 in its light-emitting layer. Furthermore, the reduction potential was −2.66 eV, and thus the compound including mCzBPBfpy-03 has a relatively deep LUMO level. The calculation results of Example 4 also show that the compound in which a substituent is bonded to the 4-position of benzofuropyridine has a deeper LUMO level than the other compounds in which a substituent is bonded to a site other than the 4-position. Accordingly, electron injection from a layer including mCzBPBfpy-03 of one embodiment of the present invention into a layer with a relatively deep LUMO level (−2.6 eV or lower) and electron injection from a layer with a relatively deep LUMO level (−2.8 eV or higher) into the layer including mCzBPBfpy-03 are improved, which is preferable.

The phosphorescence spectrum of mCzBPBfpy-03 was measured. A sample for the measurement was fabricated in such a manner that a thin film of mCzBPBfpy-03 with a thickness of approximately 50 nm was formed over a quartz substrate, and sealed with another quartz substrate in a nitrogen atmosphere. The measurement was performed in a manner similar to that described in Example 1. The first peak of this phosphorescence on the short wavelength side was 456 nm (2.72 eV), and this value was regarded as the T1 level. Therefore, mCzBPBfpy-03 has a high T1 level and is suitable as a host material for an emission center substance emitting blue phosphorescence.

Example 6

In this example, the light-emitting element (the light-emitting element 1) in which 4-[3′-(9H-carbazol-9-yl)biphenyl-3-yl]benzo[4,5]furo[3,2-b]pyridine (abbreviation: mCz-BPBfpy-03) that is the compound described in Embodiment 1 having a structure in which a carbazole skeleton is bonded to a benzofuropyridyl group or a benzothienopyridyl group through an arylene group is used as a host material in a light-emitting layer including an emission center substance emitting blue phosphorescence is described.

The molecular structures of compounds used in this example are shown in Structural Formulae (vi) to (ix) and (134) below. The element structure in FIG. 1A was employed.

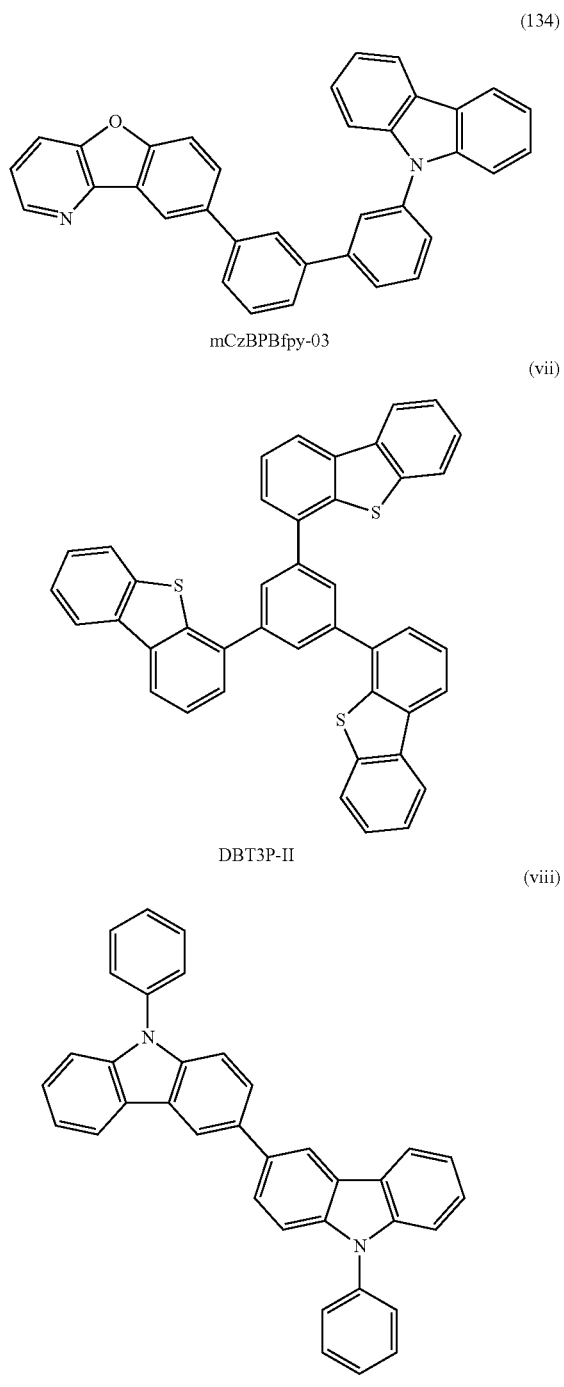

(134)

mCzBPBfpy-03

(vii)

DBT3P-II (viii)

PCCP

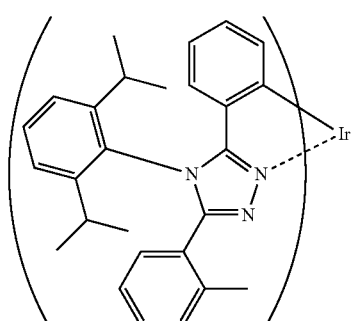

[Ir(mpptz-diPrp)3]

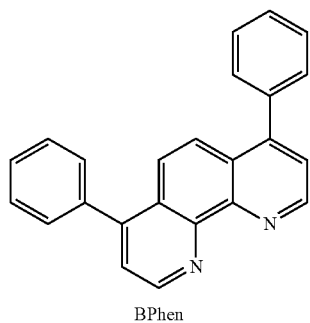

BPhen

The light-emitting element 2 was formed in a manner similar to that of the light-emitting element 1 except for the hole-transport layer 112 to the electron-injection layer 115. Instead of the hole-transport layer 112 of the light-emitting element 1, 3,3'-bis(9-phenyl-9H-carbazole) (abbreviation: PCCP) was deposited to a thickness of 20 nm. The light-emitting layer 113 was formed as follows: PCCP, mCzBPBfpy-03, and tris{2-[5-(2-methylphenyl)-4-(2,6-diisopropylphenyl)-4H-1,2,4-triazol-3-yl-κN2]phenyl-κC}iridium(III) (abbreviation: [Ir(mpptz-diPrp)$_3$]) were co-deposited to a thickness of 30 nm by evaporation such that the mass ratio of PCCP to mCzBPBfpy-03 and [Ir(mpptz-diPrp)$_3$] was 1:0.3:0.06, and then mCzBPBfpy-03 and [Ir(mpptz-diPrp)$_3$] were co-deposited to a thickness of 10 nm by evaporation such that the mass ratio of mCzBPBfpy-03 to [Ir(mpptz-diPrp)$_3$] was 1:0.06. Then, mCzBPBfpy-03 was deposited to a thickness of 10 nm as the electron-transport layer 114. After that, the electron-injection layer 115 was formed as follows: bathophenanthroline (abbreviation: BPhen) was deposited to a thickness of 15 nm and lithium fluoride was deposited to a thickness of 1 nm.

Table 10 shows an element structure of the light-emitting element 2 obtained in the above manner.

TABLE 10

| | First electrode 101 | Hole-injection layer 111 | Hole-transport layer 112 | Light-emitting layer 113 | Electron-transport layer 114 | Electron-injection layer 115 | Second electrode 102 |
|---|---|---|---|---|---|---|---|
| Element 2 | ITSO (70 nm) | DBT3P-II:MoOx (20 nm, 2:1) | PCCP (20 nm) | *1 | mCzBPBfpy-03 (10 nm) | *2 | Al (200 nm) |

*1 PCCP:mCzBPBfpy-03:[Ir(mpptz-diPrp)$_3$] (1:0.3:0.06, 30 nm)\CzBPBfpy-03:[Ir(mpptz-diPrp)$_3$] (1:0.06, 10 nm)
*2 BPhen (15 nm)\LiF (1 nm)

The structure except for the hole-transport layer to the electron-injection layer is the same as that of the light-emitting element 1, and repetition of the description thereof is omitted. Refer to the fabrication method of the light-emitting element 1.

Operation Characteristics of Light-Emitting Element 2

Operation characteristics of the light-emitting element 2 obtained in the above-described manner were measured. Note that the measurement was performed at room temperature (in an atmosphere kept at 25° C.).

Figure 28:
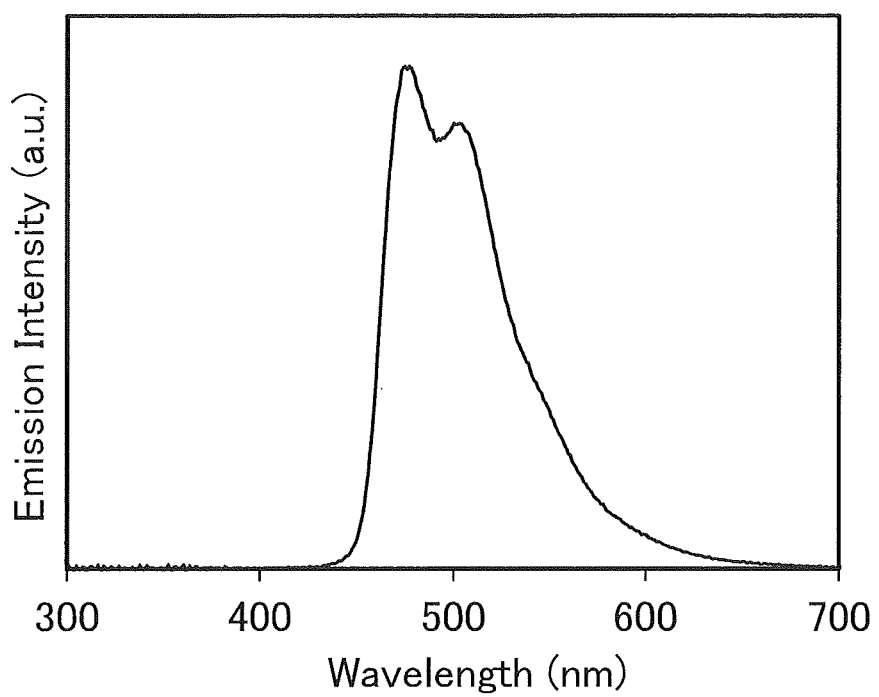
FIG. 28 shows a normalized emission spectrum of a light-emitting element 2.
Figure 29:
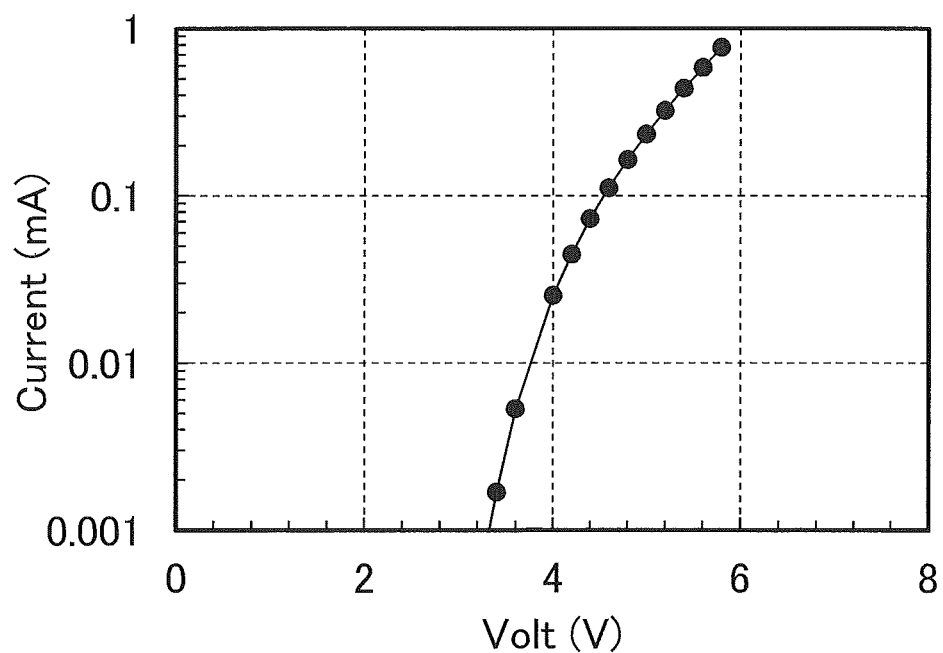
FIG. 29 shows current-voltage characteristics of the light-emitting element 2.
Figure 30:
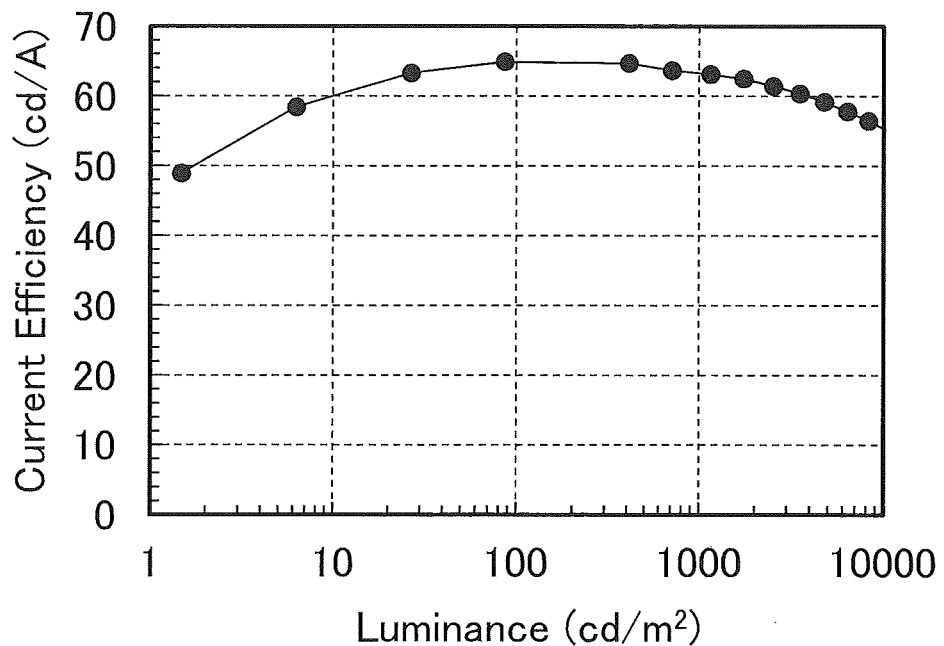
FIG. 30 shows luminance-current efficiency characteristics of the light-emitting element 2.
Figure 31:
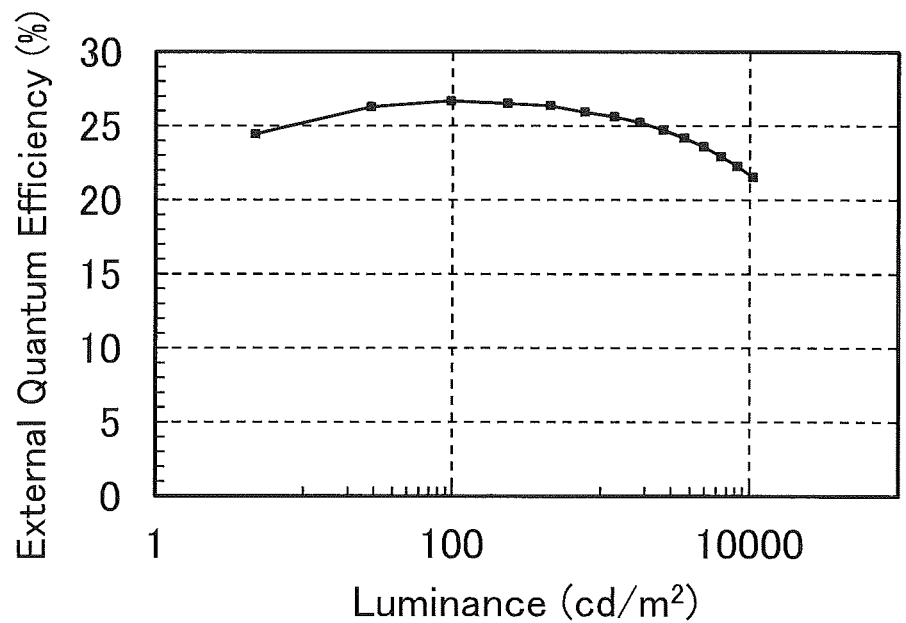
FIG. 31 shows luminance-external quantum efficiency characteristics of the light-emitting element 2.

FIG. 28 shows a normalized emission spectrum of the light-emitting element 2, FIG. 29 shows current-voltage characteristics thereof, FIG. 30 shows luminance-current efficiency characteristics thereof, and FIG. 31 shows luminance-external quantum efficiency characteristics thereof. Table 11 lists characteristics of the light-emitting element 2.

TABLE 11

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Element 2 | 3.8 | 0.051 | 1.3 | (0.18, 0.41) | 773 | 60 | 50 | 26 |

FIG. 28 shows that light emission derived from [Ir(mpptz-diPrp)$_3$] is obtained. According to FIG. 31, the maximum external quantum efficiency is 26%; thus, the dopant can emit light very efficiently. Therefore, mCzBPBfpy-03 has a high T1 level. According to FIG. 29, the voltage at which light emission starts is as significantly low as 2.6 V, and the driving voltage at 1000 cd/m$^2$ is also as low as 3.8 V. FIG. 30 shows that the current efficiency is as high as 62 cd/A. From these results, it is found that with use of the material of one embodiment of the present invention having a structure in which a carbazole skeleton is bonded to a benzofuropyridyl group through an arylene group as a host material for an emission center material emitting blue phosphorescence or for an electron-transport layer, an excellent element which has high efficiency and which is driven at low voltage can be obtained. In addition, FIG. 30 shows that the current efficiency is stably high at any luminance; therefore, the element has excellent carrier balance.

Furthermore, the reliability of the element driven at a constant current of 0.14 mA at initial luminance of 1700 cd/m$^2$ was examined. It took 165 hours until the luminance decreased to 51%. Note that before the reliability test, aging was performed at 0.14 mA for 20 hours. Accordingly, mCzBPBfpy-03 of one embodiment of the present invention has high reliability as a host material for an emission center material emitting blue phosphorescence. Therefore, it is found that with use of the material of one embodiment of the present invention having a structure in which a carbazole skeleton is bonded to a benzofuropyridyl group through an arylene group as a host material of an emission center material emitting blue phosphorescence, a highly reliable element can be obtained.

This application is based on Japanese Patent Application serial no. 2015-097649 filed with Japan Patent Office on May 12, 2015, the entire contents of which are hereby incorporated by reference.

What is claimed is:

1. A light-emitting element comprising:
a pair of electrodes; and
an EL layer between the pair of electrodes,
wherein the EL layer comprises a substance comprising a carbazole skeleton,
wherein the substance has a bond between a substituted or unsubstituted first arylene group and a nitrogen atom comprised in the carbazole skeleton,
wherein the first arylene group is bonded to a substituted or unsubstituted benzofuropyridyl group or a substituted or unsubstituted benzothienopyridyl group, and
wherein the first arylene group comprises 1 to 5 substituted or unsubstituted second arylene groups which are bonded to one another.

2. The light-emitting element according to claim 1, wherein the EL layer comprises a layer comprising a light-emitting substance.

3. The light-emitting element according to claim 1, wherein the EL layer comprises a layer comprising an iridium compound.

4. A compound represented by Formula (G1):

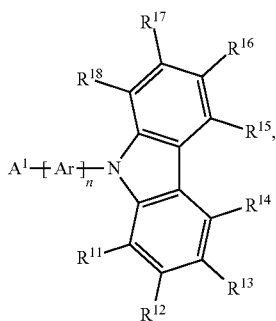

(G1)

wherein A$^1$ represents a substituted or unsubstituted benzofuropyridyl group or a substituted or unsubstituted benzothienopyridyl group;

wherein Ar represents a substituted or unsubstituted arylene group having 6 to 13 carbon atoms;

wherein each of R$^{11}$ to R$^{18}$ independently represents hydrogen, a substituted or unsubstituted alkyl group having 1 to 6 carbon atoms, or a substituted or unsubstituted aryl group having 6 to 13 carbon atoms; and wherein n represents a natural number of 1 to 5.

5. The compound according to claim 4,
wherein the compound is represented by Formula (G2-1):

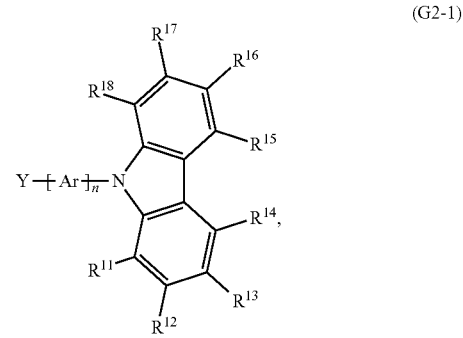

(G2-1)

wherein Ar represents a substituted or unsubstituted arylene group having 6 to 13 carbon atoms;

wherein each of R$^{11}$ to R$^{18}$ independently represents hydrogen, a substituted or unsubstituted alkyl group having 1 to 6 carbon atoms, or a substituted or unsubstituted aryl group having 6 to 13 carbon atoms;

wherein n represents a natural number of 1 to 5;

wherein Y is represented by Formula (G2-2):

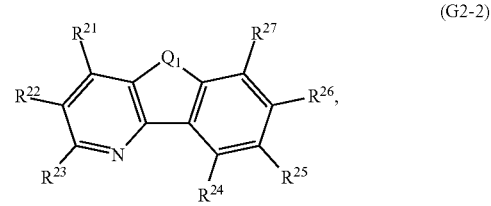

(G2-2)

wherein one of R$^{21}$ to R$^{27}$ represents a single bond between Ar and Y in Formula (G2-1);

wherein each of the others of R$^{21}$ to R$^{27}$ independently represents hydrogen, a substituted or unsubstituted alkyl group having 1 to 6 carbon atoms, or a substituted or unsubstituted aryl group having 6 to 13 carbon atoms; and wherein Q$^1$ represents an oxygen atom or a sulfur atom.

6. The compound according to claim 5, wherein one of R$^{25}$, R$^{27}$ and R$^{21}$ represents the single bond between Ar and Y.

7. A compound represented by Formula (G3-1):

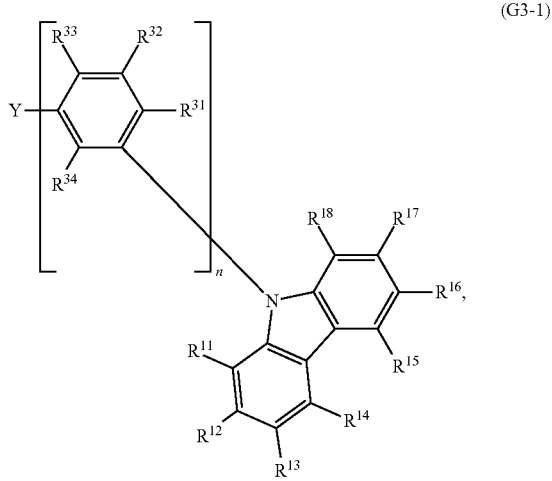

wherein each of $R^{11}$ to $R^{18}$ and $R^{31}$ to $R^{34}$ independently represents hydrogen, a substituted or unsubstituted alkyl group having 1 to 6 carbon atoms, or a substituted or unsubstituted aryl group having 6 to 13 carbon atoms;
wherein n represents a natural number of 1 to 5; and
wherein Y is represented by Formula (G3-2):

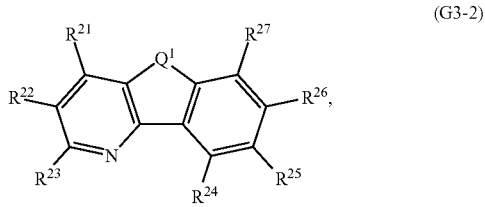

wherein one of $R^{21}$ to $R^{27}$ represents a single bond between a phenylene skeleton and Y in Formula (G3-1);
wherein each of the others of $R^{21}$ to $R^{27}$ independently represents hydrogen, a substituted or unsubstituted alkyl group having 1 to 6 carbon atoms, or a substituted or unsubstituted aryl group having 6 to 13 carbon atoms; and
wherein $Q^1$ represents an oxygen atom or a sulfur atom.

8. The compound according to claim 7, wherein one of $R^{25}$, $R^{27}$ and $R^{21}$ represents the single bond between the phenylene skeleton and Y.

9. A compound represented by Formula (G4-1):

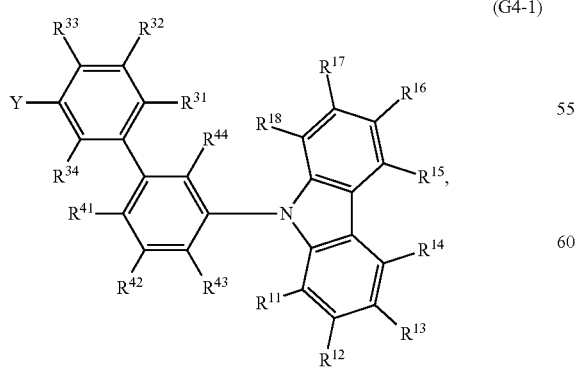

wherein each of $R^{11}$ to $R^{18}$, $R^{31}$ to $R^{34}$, and $R^{41}$ to $R^{44}$ independently represents hydrogen, a substituted or unsubstituted alkyl group having 1 to 6 carbon atoms, or a substituted or unsubstituted aryl group having 6 to 13 carbon atoms; and
wherein Y is represented by Formula (G4-2):

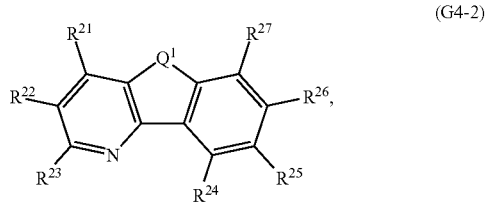

wherein one of $R^{21}$ to $R^{27}$ represents a single bond between a phenylene skeleton and Y in Formula (G4-1);
wherein each of the others of $R^{21}$ to $R^{27}$ independently represents hydrogen, a substituted or unsubstituted alkyl group having 1 to 6 carbon atoms, or a substituted or unsubstituted aryl group having 6 to 13 carbon atoms; and
wherein $Q^1$ represents an oxygen atom or a sulfur atom.

10. The compound according to claim 9, wherein one of $R^{25}$, $R^{27}$ and $R^{21}$ represents the single bond between the phenylene skeleton and Y.

11. The compound according to claim 4,
wherein the compound is represented by Formula (112):

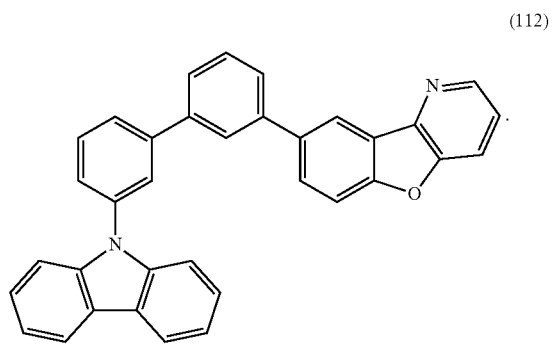 [SMILES: c1cc(-c2cccc(-n3c4ccccc4c4ccccc43)c2)cc(-c2ccc3oc4cccnc4c3c2)c1]

12. The compound according to claim 4,
wherein the compound is represented by Formula (122):

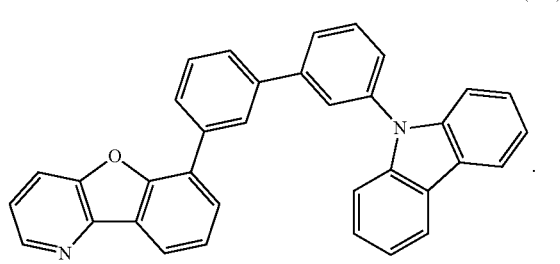

13. The compound according to claim 4, wherein the compound is represented by Formula (134):

(134)

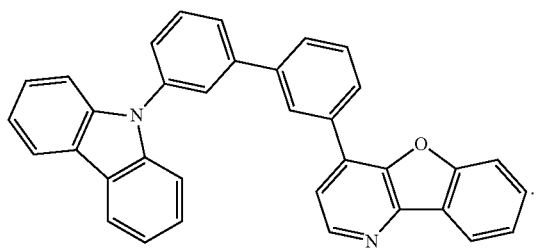

14. A light-emitting element comprising:
a pair of electrodes; and
an EL layer between the pair of electrodes, wherein the EL layer comprises the compound according to claim 4.

15. The light-emitting element according to claim 14, wherein the EL layer further comprises an iridium complex.

16. A light-emitting device comprising:
the light-emitting element according to claim 14; and
a unit configured to control the light-emitting element.

17. A display device comprising:
the light-emitting element according to claim 14; and
a unit configured to control the light-emitting element.

18. A lighting device comprising:
the light-emitting element according to claim 14; and
a unit configured to control the light-emitting element.

19. An electronic device comprising:
the light-emitting element according to claim 14; and
an operation switch.

\* \* \* \* \*